US010398422B2

(12) United States Patent
Serowski et al.

(10) Patent No.: US 10,398,422 B2
(45) Date of Patent: *Sep. 3, 2019

(54) SURGICAL INSTRUMENTS, SYSTEMS AND METHODS OF USE

(71) Applicant: MAQUET CARDIOVASCULAR LLC, Wayne, NJ (US)

(72) Inventors: Andrew Serowski, Milipitas, CA (US); Juan I. Perez, San Jose, CA (US); Kumar Jambunathan, Sunnyvale, CA (US); Kyle Klein, San Jose, CA (US); Kristopher Yee, San Francisco, CA (US)

(73) Assignee: MAQUET CARDIOVASCULAR LLC, Wayne, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/585,068

(22) Filed: May 2, 2017

(65) Prior Publication Data

US 2017/0238917 A1   Aug. 24, 2017

Related U.S. Application Data

(62) Division of application No. 13/160,445, filed on Jun. 14, 2011, now Pat. No. 9,655,605.

(Continued)

(51) Int. Cl.
*A61B 17/02* (2006.01)
*A61B 90/50* (2016.01)
(Continued)

(52) U.S. Cl.
CPC .......... *A61B 17/02* (2013.01); *A61B 17/0206* (2013.01); *A61B 90/50* (2016.02);
(Continued)

(58) Field of Classification Search
CPC . A61B 17/02; A61B 17/0206; A61B 17/0293; A61B 17/0218; A61B 2017/0237–0243
See application file for complete search history.

(56) References Cited

U.S. PATENT DOCUMENTS

| 1,706,500 A | 3/1929 | Smith |
| 2,082,782 A | 6/1937 | Allen |

(Continued)

FOREIGN PATENT DOCUMENTS

| EP | 2579785 B1 | 11/2016 |
| JP | 2003521296 A | 7/2003 |

(Continued)

OTHER PUBLICATIONS

International Search Report related to PCT/2011/040399 (now published as WO2011/159733A1) to Serowski et al. filed on Jun. 14, 2011.

(Continued)

*Primary Examiner* — Eduardo C Robert
*Assistant Examiner* — Michelle C Eckman
(74) *Attorney, Agent, or Firm* — Wesley Scott Ashton

(57) ABSTRACT

A surgical instrument includes a mount body, a joint member, an arm, and a working end. The mount body has a top portion, a distal end, a proximal end and a bottom portion. The joint member is pivotally mounted at a distal end portion of the mount body, to allow positioning of a proximal portion of an arm extending distally from the joint member. The joint member is also configured to at least partially constrain movement of the proximal portion of the arm to a plane. The working end is mounted to a distal end portion of the arm. The surgical instrument can be configured as a heart stabilizer or a heart positioner. The joint member may further be configured as a slotted ball, a disk member, or a combination thereof.

24 Claims, 17 Drawing Sheets

Related U.S. Application Data

(60) Provisional application No. 61/354,516, filed on Jun. 14, 2010.

(51) Int. Cl.
*A61B 90/57* (2016.01)
*A61B 17/30* (2006.01)

(52) U.S. Cl.
CPC ...... *A61B 90/57* (2016.02); *A61B 2017/0237* (2013.01); *A61B 2017/0243* (2013.01); *A61B 2017/306* (2013.01); *A61B 2017/308* (2013.01); *A61B 2090/508* (2016.02); *A61B 2090/571* (2016.02)

(56) References Cited

U.S. PATENT DOCUMENTS

| | | |
|---|---|---|
| 2,296,793 A | 9/1942 | Kirschbaum |
| 2,450,194 A | 9/1948 | Glaser |
| 2,590,527 A | 3/1952 | Fluck |
| 2,693,795 A | 11/1954 | Grieshaber |
| 2,863,444 A | 12/1958 | Winsten |
| 3,096,962 A | 7/1963 | Meijs |
| 3,361,133 A | 1/1968 | Kimberley et al. |
| 3,392,722 A | 7/1968 | Jorgensen |
| 3,466,079 A | 9/1969 | Mammel |
| 3,584,822 A | 6/1971 | Oram |
| 3,683,926 A | 8/1972 | Suzuki |
| 3,720,433 A | 3/1973 | Rosfelder |
| 3,783,373 A | 1/1974 | Jawor |
| 3,783,873 A | 1/1974 | Jacobs |
| 3,807,406 A | 4/1974 | Rafferty et al. |
| 3,858,578 A * | 1/1975 | Milo .................... A61B 17/02 600/229 |
| 3,858,926 A | 1/1975 | Ottenhues |
| 3,882,855 A | 5/1975 | Schulte et al. |
| 3,882,885 A | 5/1975 | McCain |
| 3,912,317 A | 10/1975 | Ohnaka |
| 3,916,909 A | 11/1975 | Kletschka et al. |
| 3,983,863 A | 10/1976 | Janke et al. |
| 4,047,532 A | 9/1977 | Phillips et al. |
| 4,048,987 A | 9/1977 | Hurson |
| 4,049,000 A | 9/1977 | Williams |
| 4,049,002 A | 9/1977 | Kletschka et al. |
| 4,049,484 A | 9/1977 | Priest et al. |
| 4,052,980 A | 10/1977 | Grams et al. |
| 4,094,484 A | 6/1978 | Galione |
| 4,096,853 A | 6/1978 | Weigand |
| 4,096,864 A | 6/1978 | Kletschka et al. |
| 4,108,178 A | 8/1978 | Betush |
| 4,168,708 A | 9/1979 | Lepley, Jr. et al. |
| 4,217,890 A | 8/1980 | Owens |
| 4,226,228 A | 10/1980 | Shin et al. |
| 4,230,119 A | 10/1980 | Blum |
| 4,300,541 A | 11/1981 | Burgin |
| 4,300,564 A | 11/1981 | Furihata |
| 4,306,561 A | 12/1981 | de Medinaceli |
| 4,350,160 A | 9/1982 | Kolesov et al. |
| 4,366,819 A | 1/1983 | Kaster |
| 4,368,736 A | 1/1983 | Kaster |
| 4,421,107 A | 12/1983 | Estes et al. |
| 4,428,368 A | 1/1984 | Torii |
| 4,428,815 A | 1/1984 | Powell et al. |
| 4,434,791 A | 3/1984 | Darnell |
| 4,457,300 A | 7/1984 | Budde |
| 4,461,284 A | 7/1984 | Fackler |
| 4,483,339 A | 11/1984 | Gillis |
| 4,492,229 A | 1/1985 | Grunwald |
| 4,597,382 A | 7/1986 | Perez, Jr. |
| 4,617,916 A | 10/1986 | LeVahn et al. |
| 4,627,421 A | 12/1986 | Symbas et al. |
| 4,637,377 A | 1/1987 | Loop |
| 4,646,747 A | 3/1987 | Lundback |
| 4,673,161 A | 6/1987 | Flynn et al. |
| 4,688,570 A | 8/1987 | Kramer et al. |
| 4,702,230 A | 10/1987 | Pelta |
| 4,708,510 A | 11/1987 | McConnell et al. |
| D293,470 S | 12/1987 | Adler |
| 4,718,418 A | 1/1988 | L'Esperance, Jr. |
| 4,726,356 A | 2/1988 | Santilli et al. |
| 4,726,358 A | 2/1988 | Brady |
| 4,736,749 A | 4/1988 | Lundback |
| 4,747,394 A | 5/1988 | Watanabe |
| 4,747,395 A | 5/1988 | Brief |
| 4,754,746 A | 7/1988 | Cox |
| 4,767,142 A | 8/1988 | Takahashi et al. |
| 4,767,404 A | 8/1988 | Renton |
| 4,787,662 A | 11/1988 | Dewez |
| 4,803,984 A | 2/1989 | Narayanan et al. |
| 4,808,163 A | 2/1989 | Laub |
| 4,827,926 A | 5/1989 | Carol |
| 4,829,985 A | 5/1989 | Couetil |
| 4,841,967 A | 6/1989 | Chang et al. |
| 4,852,552 A | 8/1989 | Chaux |
| 4,854,318 A | 8/1989 | Solem et al. |
| 4,858,552 A | 8/1989 | Glatt et al. |
| 4,863,133 A | 9/1989 | Bonnell |
| 4,865,019 A | 9/1989 | Phillips |
| 4,869,457 A | 9/1989 | Ewerlof |
| 4,884,559 A | 12/1989 | Collins |
| 4,892,526 A | 1/1990 | Reese |
| 4,904,012 A | 2/1990 | Nishiguchi et al. |
| 4,917,427 A | 4/1990 | Scaglia |
| 4,925,443 A | 5/1990 | Heilman et al. |
| 4,931,341 A | 6/1990 | Haffer et al. |
| 4,941,872 A | 7/1990 | Felix et al. |
| 4,949,707 A | 8/1990 | LeVahn et al. |
| 4,949,927 A | 8/1990 | Madocks et al. |
| 4,955,896 A | 9/1990 | Freeman |
| 4,957,477 A | 9/1990 | Lundback |
| 4,962,758 A | 10/1990 | Lasner et al. |
| 4,971,037 A | 11/1990 | Pelta |
| 4,973,300 A | 11/1990 | Wright |
| 4,989,587 A | 2/1991 | Farley |
| 4,991,578 A | 2/1991 | Cohen |
| 4,993,862 A | 2/1991 | Pelta |
| 5,009,660 A | 4/1991 | Clapham |
| 5,011,469 A | 4/1991 | Buckberg et al. |
| 5,019,086 A | 5/1991 | Neward |
| 5,025,779 A | 6/1991 | Bugge |
| 5,034,001 A | 7/1991 | Garrison et al. |
| 5,036,867 A | 8/1991 | Biswas |
| 5,036,868 A | 8/1991 | Berggren et al. |
| 5,037,428 A | 8/1991 | Picha et al. |
| 5,052,373 A | 10/1991 | Michelson |
| 5,053,041 A | 10/1991 | Ansari et al. |
| 5,071,407 A | 12/1991 | Termin et al. |
| 5,080,088 A | 1/1992 | LeVahn |
| 5,087,247 A | 2/1992 | Horn et al. |
| 5,098,369 A | 3/1992 | Heilman et al. |
| 5,098,396 A | 3/1992 | Taylor et al. |
| 5,098,432 A | 3/1992 | Wagenknecht |
| 5,102,853 A | 4/1992 | Chattha et al. |
| 5,107,852 A | 4/1992 | Davidson et al. |
| 5,119,804 A | 6/1992 | Anstadt |
| 5,125,395 A | 6/1992 | Adair |
| 5,131,905 A | 7/1992 | Grooters |
| 5,133,724 A | 7/1992 | Wilson, Jr. et al. |
| 5,139,517 A | 8/1992 | Corral |
| 5,150,706 A | 9/1992 | Cox et al. |
| 5,152,777 A | 10/1992 | Goldberg et al. |
| 5,159,921 A | 11/1992 | Hoover |
| RE34,150 E | 12/1992 | Santilli et al. |
| 5,167,223 A | 12/1992 | Koros et al. |
| 5,171,254 A | 12/1992 | Sher |
| 5,180,392 A | 1/1993 | Skeie et al. |
| 5,192,070 A | 3/1993 | Nagai et al. |
| 5,192,289 A | 3/1993 | Jessen |
| 5,196,003 A | 3/1993 | Bilweis |
| 5,203,769 A | 4/1993 | Clement et al. |
| 5,242,386 A | 9/1993 | Holzer |
| 5,242,399 A | 9/1993 | Lau et al. |
| 5,245,705 A | 9/1993 | Swaney |

(56) References Cited

U.S. PATENT DOCUMENTS

| | | |
|---|---|---|
| 5,256,132 A | 10/1993 | Snyders |
| 5,268,640 A | 12/1993 | Du et al. |
| 5,287,861 A | 2/1994 | Wilk |
| 5,290,082 A | 3/1994 | Palmer et al. |
| 5,293,863 A | 3/1994 | Zhu et al. |
| 5,300,087 A | 4/1994 | Knoepfler |
| 5,318,013 A | 6/1994 | Wilk |
| 5,323,789 A | 6/1994 | Berggren et al. |
| 5,328,471 A | 7/1994 | Slepian |
| 5,336,170 A | 8/1994 | Salerno et al. |
| 5,336,252 A | 8/1994 | Cohen |
| 5,339,801 A | 8/1994 | Poloyko et al. |
| 5,348,259 A | 9/1994 | Blanco et al. |
| 5,363,841 A | 11/1994 | Coker |
| 5,363,882 A | 11/1994 | Chikama |
| 5,368,566 A | 11/1994 | Crocker |
| 5,372,147 A | 12/1994 | Lathrop, Jr. et al. |
| 5,381,788 A | 1/1995 | Matula et al. |
| 5,382,256 A | 1/1995 | del Castillo |
| 5,382,756 A | 1/1995 | Dagan |
| 5,383,840 A | 1/1995 | Heilman et al. |
| 5,385,840 A | 1/1995 | Benson et al. |
| 5,395,333 A | 3/1995 | Brill |
| 5,397,307 A | 3/1995 | Goodin |
| 5,403,280 A | 4/1995 | Wang |
| 5,417,709 A | 5/1995 | Slater |
| 5,423,737 A | 6/1995 | Cartmell et al. |
| 5,425,705 A | 6/1995 | Evard et al. |
| 5,437,651 A | 8/1995 | Todd et al. |
| 5,449,372 A | 9/1995 | Schmaltz et al. |
| 5,452,733 A | 9/1995 | Sterman et al. |
| 5,453,078 A | 9/1995 | Valentine et al. |
| 5,467,763 A | 11/1995 | McMahon et al. |
| 5,480,425 A | 1/1996 | Ogilive |
| 5,484,391 A | 1/1996 | Buckman, Jr. et al. |
| 5,484,412 A | 1/1996 | Pierpont |
| 5,489,280 A | 2/1996 | Russell |
| 5,498,256 A | 3/1996 | Furnish |
| 5,503,617 A | 4/1996 | Jako |
| 5,509,890 A | 4/1996 | Kazama |
| 5,512,037 A | 4/1996 | Russell et al. |
| 5,512,038 A | 4/1996 | O'Neal et al. |
| 5,513,827 A | 5/1996 | Michelson |
| 5,514,076 A | 5/1996 | Ley |
| 5,520,609 A | 5/1996 | Moll et al. |
| 5,520,610 A | 5/1996 | Giglio et al. |
| 5,522,819 A | 6/1996 | Graves et al. |
| 5,522,882 A | 6/1996 | Gaterud et al. |
| 5,529,571 A | 6/1996 | Daniel |
| 5,536,251 A | 7/1996 | Evard et al. |
| 5,547,458 A | 8/1996 | Ortiz et al. |
| 5,554,101 A | 9/1996 | Matula et al. |
| 5,555,897 A | 9/1996 | Lathrop, Jr. et al. |
| 5,558,665 A | 9/1996 | Kieturakis |
| 5,564,682 A | 10/1996 | Tsuji |
| 5,569,274 A | 10/1996 | Rapacki et al. |
| 5,571,215 A | 11/1996 | Sterman et al. |
| 5,573,496 A | 11/1996 | McPherson et al. |
| 5,607,421 A | 3/1997 | Jeevanandam et al. |
| 5,607,446 A | 3/1997 | Beehler et al. |
| 5,613,937 A | 3/1997 | Garrison et al. |
| 5,616,117 A | 4/1997 | Dinkier et al. |
| 5,632,746 A | 5/1997 | Middleman et al. |
| 5,645,560 A | 7/1997 | Crocker et al. |
| 5,651,378 A | 7/1997 | Matheny et al. |
| 5,662,300 A | 9/1997 | Michelson |
| 5,667,480 A | 9/1997 | Knight et al. |
| 5,707,362 A | 1/1998 | Yoon |
| 5,713,951 A | 2/1998 | Garrison et al. |
| 5,722,935 A | 3/1998 | Christian |
| 5,727,569 A | 3/1998 | Benetti et al. |
| 5,728,151 A | 3/1998 | Garrison et al. |
| 5,730,757 A | 3/1998 | Benetti et al. |
| 5,735,290 A | 4/1998 | Sterman et al. |
| 5,749,892 A | 5/1998 | Vierra et al. |
| 5,755,660 A | 5/1998 | Tyagi |
| 5,769,870 A | 6/1998 | Salahieh et al. |
| 5,772,583 A | 6/1998 | Wright et al. |
| 5,782,746 A | 7/1998 | Wright |
| 5,795,291 A | 8/1998 | Koros et al. |
| 5,797,934 A | 8/1998 | Rygaard |
| 5,797,960 A | 8/1998 | Stevens et al. |
| 5,799,661 A | 9/1998 | Boyd et al. |
| 5,803,902 A | 9/1998 | Sienkiewicz et al. |
| 5,807,243 A | 9/1998 | Vierra et al. |
| 5,813,410 A | 9/1998 | Levin |
| 5,818,231 A | 10/1998 | Smith |
| 5,820,373 A | 10/1998 | Okano et al. |
| 5,830,214 A | 11/1998 | Flom et al. |
| 5,846,187 A | 12/1998 | Wells et al. |
| 5,846,193 A | 12/1998 | Wright |
| 5,846,194 A | 12/1998 | Wasson et al. |
| 5,846,219 A | 12/1998 | Vancaillie |
| 5,864,275 A | 1/1999 | Ohashi et al. |
| 5,865,730 A | 2/1999 | Fox et al. |
| 5,865,731 A | 2/1999 | Lenox et al. |
| 5,868,770 A | 2/1999 | Rygaard |
| 5,875,782 A * | 3/1999 | Ferrari ............... A61B 17/0206 128/898 |
| 5,876,332 A | 3/1999 | Looney |
| 5,879,291 A | 3/1999 | Kolata et al. |
| 5,882,299 A | 3/1999 | Rastegar et al. |
| 5,885,271 A | 3/1999 | Hamilton et al. |
| 5,888,247 A | 3/1999 | Benetti |
| 5,891,017 A | 4/1999 | Swindle et al. |
| 5,894,843 A | 4/1999 | Benetti et al. |
| 5,899,425 A * | 5/1999 | Corey, Jr. ............... A61B 17/02 248/276.1 |
| 5,899,627 A | 5/1999 | Dobrovolny |
| 5,906,601 A | 5/1999 | Lydon et al. |
| 5,906,602 A | 5/1999 | Weber et al. |
| 5,906,607 A | 5/1999 | Taylor et al. |
| 5,908,378 A | 6/1999 | Kovacs et al. |
| 5,908,382 A | 6/1999 | Koros et al. |
| 5,913,876 A | 6/1999 | Taylor et al. |
| 5,921,979 A | 7/1999 | Kovac et al. |
| 5,928,139 A | 7/1999 | Koros et al. |
| 5,944,658 A | 8/1999 | Koros et al. |
| 5,944,736 A | 8/1999 | Taylor et al. |
| 5,947,125 A | 9/1999 | Benetti |
| 5,947,896 A * | 9/1999 | Sherts ............... A61B 17/0293 600/229 |
| 5,957,423 A | 9/1999 | Kronner |
| 5,957,832 A | 9/1999 | Taylor et al. |
| 5,957,835 A | 9/1999 | Anderson et al. |
| 5,967,972 A | 10/1999 | Santilli et al. |
| 5,967,973 A * | 10/1999 | Sherts ............... A61B 17/0293 600/205 |
| 5,976,069 A | 11/1999 | Navia et al. |
| 5,976,080 A * | 11/1999 | Farascioni ......... A61B 17/0293 600/201 |
| 5,976,171 A | 11/1999 | Taylor |
| 5,984,843 A | 11/1999 | Morton |
| 5,984,864 A | 11/1999 | Fox et al. |
| 5,984,865 A | 11/1999 | Farley et al. |
| 5,984,867 A | 11/1999 | Deckman et al. |
| 6,007,486 A | 12/1999 | Hunt et al. |
| 6,007,523 A | 12/1999 | Mangosong |
| 6,010,531 A | 1/2000 | Donlon et al. |
| 6,013,027 A | 1/2000 | Khan et al. |
| 6,015,427 A | 1/2000 | Mueller et al. |
| 6,017,304 A | 1/2000 | Vierra et al. |
| 6,019,722 A | 2/2000 | Spence et al. |
| 6,027,476 A | 2/2000 | Sterman et al. |
| 6,029,671 A | 2/2000 | Stevens et al. |
| 6,030,340 A | 2/2000 | Maffei et al. |
| D421,803 S | 3/2000 | Koros et al. |
| 6,032,672 A | 3/2000 | Taylor |
| 6,033,362 A | 3/2000 | Cohn |
| 6,033,641 A | 3/2000 | Hall et al. |
| 6,036,641 A | 3/2000 | Taylor et al. |
| 6,042,539 A | 3/2000 | Harper et al. |
| 6,050,266 A | 4/2000 | Benetti et al. |
| 6,063,021 A | 5/2000 | Hossain et al. |

(56) References Cited

U.S. PATENT DOCUMENTS

| | | | |
|---|---|---|---|
| 6,066,160 A | 5/2000 | Colvin et al. | |
| 6,071,235 A | 6/2000 | Furnish et al. | |
| 6,071,295 A | 6/2000 | Takahashi | |
| 6,083,154 A | 7/2000 | Liu et al. | |
| 6,099,468 A | 8/2000 | Santilli et al. | |
| 6,102,853 A | 8/2000 | Scirica et al. | |
| 6,102,854 A | 8/2000 | Cartier et al. | |
| 6,110,187 A | 8/2000 | Donlon | |
| 6,113,534 A | 9/2000 | Koros et al. | |
| 6,120,436 A | 9/2000 | Anderson et al. | |
| 6,132,370 A | 10/2000 | Furnish et al. | |
| 6,139,492 A | 10/2000 | Vierra et al. | |
| 6,149,583 A | 11/2000 | Vierra et al. | |
| 6,152,874 A | 11/2000 | Looney et al. | |
| 6,159,201 A | 12/2000 | Hamilton et al. | |
| 6,159,231 A | 12/2000 | Looney et al. | |
| 6,168,577 B1 | 1/2001 | Niederjohn et al. | |
| 6,183,486 B1 | 2/2001 | Snow et al. | |
| 6,190,311 B1 | 2/2001 | Glines et al. | |
| 6,193,652 B1 | 2/2001 | Berky et al. | |
| 6,199,556 B1 | 3/2001 | Benetti et al. | |
| 6,200,263 B1 | 3/2001 | Person | |
| 6,210,323 B1 | 4/2001 | Gilhuly et al. | |
| 6,213,940 B1 | 4/2001 | Sherts et al. | |
| 6,224,545 B1 | 5/2001 | Cocchia et al. | |
| 6,231,506 B1 | 5/2001 | Hu et al. | |
| 6,231,585 B1 | 5/2001 | Takahashi et al. | |
| 6,234,961 B1 | 5/2001 | Gray | |
| 6,241,655 B1 | 6/2001 | Riess | |
| 6,251,065 B1 | 6/2001 | Kochamba et al. | |
| 6,254,532 B1 | 7/2001 | Paolitto et al. | |
| 6,264,605 B1 | 7/2001 | Scirica et al. | |
| 6,283,912 B1 | 9/2001 | Hu et al. | |
| 6,306,085 B1 | 10/2001 | Farascioni | |
| 6,315,717 B1 | 11/2001 | Benetti et al. | |
| 6,322,500 B1 | 11/2001 | Sikora et al. | |
| 6,331,157 B2 | 12/2001 | Hancock | |
| 6,331,158 B1 | 12/2001 | Hu et al. | |
| 6,336,898 B1 | 1/2002 | Borst et al. | |
| 6,338,710 B1 | 1/2002 | Takahashi et al. | |
| 6,338,712 B2 | 1/2002 | Spence et al. | |
| 6,338,738 B1 * | 1/2002 | Bellotti | A61B 17/0206 600/201 |
| 6,346,077 B1 | 2/2002 | Taylor et al. | |
| 6,348,036 B1 | 2/2002 | Looney et al. | |
| 6,361,493 B1 | 3/2002 | Spence et al. | |
| 6,364,833 B1 * | 4/2002 | Valerio | A61B 17/0206 600/205 |
| 6,371,910 B1 | 4/2002 | Zwart et al. | |
| 6,375,611 B1 | 4/2002 | Voss et al. | |
| 6,390,976 B1 | 5/2002 | Spence et al. | |
| 6,394,948 B1 | 5/2002 | Borst et al. | |
| 6,394,951 B1 | 5/2002 | Taylor et al. | |
| 6,398,726 B1 | 6/2002 | Ramans et al. | |
| 6,406,424 B1 | 6/2002 | Williamson, IV et al. | |
| 6,425,901 B1 | 7/2002 | Zhu et al. | |
| 6,447,443 B1 | 9/2002 | Keogh et al. | |
| 6,458,079 B1 | 10/2002 | Cohn et al. | |
| 6,464,629 B1 * | 10/2002 | Boone | A61B 17/02 600/37 |
| 6,464,630 B1 | 10/2002 | Borst et al. | |
| 6,468,265 B1 | 10/2002 | Evans et al. | |
| 6,475,142 B1 | 11/2002 | Parsons et al. | |
| 6,478,029 B1 | 11/2002 | Boyd et al. | |
| 6,478,729 B1 | 11/2002 | Rogers et al. | |
| 6,482,151 B1 | 11/2002 | Vierra et al. | |
| 6,494,211 B1 | 12/2002 | Boyd et al. | |
| 6,503,245 B2 | 1/2003 | Palmer et al. | |
| 6,506,149 B2 | 1/2003 | Peng et al. | |
| 6,537,212 B2 | 3/2003 | Sherts et al. | |
| 6,551,242 B1 | 4/2003 | Furnish et al. | |
| 6,565,508 B2 | 5/2003 | Scirica et al. | |
| 6,581,889 B2 | 6/2003 | Carpenter et al. | |
| 6,589,166 B2 | 7/2003 | Knight et al. | |
| 6,592,573 B2 | 7/2003 | Castañeda et al. | |
| 6,602,183 B1 | 8/2003 | Levi et al. | |
| 6,607,478 B2 | 8/2003 | Williams | |
| 6,607,479 B1 | 8/2003 | Kochamba et al. | |
| 6,610,008 B1 | 8/2003 | Spence et al. | |
| 6,610,009 B2 | 8/2003 | Person | |
| 6,626,830 B1 * | 9/2003 | Califiore | A61B 17/0206 600/229 |
| 6,652,454 B2 | 11/2003 | Hu et al. | |
| 6,656,113 B2 | 12/2003 | Green, II et al. | |
| 6,685,632 B1 * | 2/2004 | Hu | A61B 17/0206 600/231 |
| 6,709,389 B2 | 3/2004 | Farascioni | |
| 6,726,622 B2 | 4/2004 | Spence et al. | |
| 6,730,020 B2 | 5/2004 | Peng et al. | |
| 6,733,445 B2 | 5/2004 | Sherts et al. | |
| 6,740,028 B2 | 5/2004 | Boone et al. | |
| 6,743,170 B1 | 6/2004 | Spence et al. | |
| 6,755,780 B2 | 6/2004 | Borst et al. | |
| 6,758,808 B2 | 7/2004 | Paul et al. | |
| 6,764,445 B2 | 7/2004 | Ramans et al. | |
| 6,790,177 B2 | 9/2004 | Phillips et al. | |
| 6,849,044 B1 | 2/2005 | Voss et al. | |
| 6,866,628 B2 * | 3/2005 | Goodman | A61B 17/02 600/228 |
| 6,875,171 B2 | 4/2005 | Paolitto et al. | |
| 6,890,292 B2 | 5/2005 | Kochamba et al. | |
| 6,893,391 B2 | 5/2005 | Taylor | |
| 6,899,670 B2 | 5/2005 | Peng et al. | |
| 6,900,592 B2 | 5/2005 | Kunhardt et al. | |
| 6,902,523 B2 | 6/2005 | Kochamba et al. | |
| 6,936,001 B1 | 8/2005 | Snow | |
| 6,936,002 B2 | 8/2005 | Kochamba et al. | |
| 6,939,297 B2 | 9/2005 | Gannoe et al. | |
| 6,969,349 B1 | 11/2005 | Spence et al. | |
| 7,018,328 B2 | 3/2006 | Mager et al. | |
| 7,048,683 B2 | 5/2006 | Borst et al. | |
| 7,056,287 B2 | 6/2006 | Taylor et al. | |
| 7,137,949 B2 | 11/2006 | Scirica et al. | |
| 7,182,731 B2 | 2/2007 | Nguyen et al. | |
| 7,189,201 B2 | 3/2007 | Borst et al. | |
| 7,191,683 B2 * | 3/2007 | Phillips | A61B 17/02 74/577 M |
| 7,195,591 B2 | 3/2007 | Spence et al. | |
| 7,201,716 B2 | 4/2007 | Boone et al. | |
| 7,220,228 B2 | 5/2007 | Hu et al. | |
| 7,226,409 B2 | 6/2007 | Peng et al. | |
| 7,238,155 B2 | 7/2007 | Hu et al. | |
| 7,250,028 B2 | 7/2007 | Julian et al. | |
| 7,311,664 B2 | 12/2007 | Goodman et al. | |
| 7,377,895 B2 | 5/2008 | Spence et al. | |
| 7,399,272 B2 | 7/2008 | Kim et al. | |
| 7,404,792 B2 | 7/2008 | Spence et al. | |
| 7,476,196 B2 | 1/2009 | Spence et al. | |
| 7,476,199 B2 | 1/2009 | Spence et al. | |
| 7,585,277 B2 | 9/2009 | Taylor et al. | |
| 7,736,307 B2 | 6/2010 | Hu et al. | |
| 7,753,844 B2 | 7/2010 | Sharratt et al. | |
| 7,758,500 B2 | 7/2010 | Boyd et al. | |
| 7,766,817 B2 | 8/2010 | Peng et al. | |
| 8,092,369 B2 | 1/2012 | Peng et al. | |
| 8,231,528 B1 | 7/2012 | Friedrich et al. | |
| 8,469,032 B2 * | 6/2013 | Farnum | A61G 13/1215 128/845 |
| 9,655,605 B2 | 5/2017 | Serowski et al. | |
| 2001/0009971 A1 | 7/2001 | Sherts et al. | |
| 2001/0025905 A1 * | 10/2001 | Carpenter | A61B 17/02 248/160 |
| 2001/0037123 A1 * | 11/2001 | Hancock | A61B 17/0206 606/167 |
| 2001/0044572 A1 | 11/2001 | Benetti et al. | |
| 2002/0058856 A1 * | 5/2002 | Peng | A61B 17/02 600/37 |
| 2002/0058957 A1 | 5/2002 | Farascioni | |
| 2002/0077532 A1 * | 6/2002 | Gannoe | A61B 17/02 600/232 |
| 2002/0091300 A1 | 7/2002 | Peng et al. | |
| 2002/0095139 A1 * | 7/2002 | Keogh | A61B 17/0206 606/1 |

(56) References Cited

U.S. PATENT DOCUMENTS

| | | | |
|---|---|---|---|
| 2002/0099268 A1* | 7/2002 | Paul | A61B 17/0206 600/201 |
| 2002/0099270 A1 | 7/2002 | Taylor et al. | |
| 2002/0111537 A1 | 8/2002 | Taylor et al. | |
| 2002/0115911 A1* | 8/2002 | Knight | A61B 17/02 600/228 |
| 2002/0161295 A1 | 10/2002 | Edwards et al. | |
| 2003/0060685 A1* | 3/2003 | Houser | A61B 17/0218 600/206 |
| 2003/0083555 A1 | 5/2003 | Hunt et al. | |
| 2003/0195393 A1 | 10/2003 | Goodman et al. | |
| 2003/0195482 A1* | 10/2003 | Schultz | A61M 1/0047 604/317 |
| 2003/0216619 A1 | 11/2003 | Scirica et al. | |
| 2003/0229271 A1* | 12/2003 | Briscoe | A61B 17/02 600/229 |
| 2004/0002625 A1* | 1/2004 | Dietz | A61B 17/0206 600/37 |
| 2004/0015047 A1 | 1/2004 | Mager et al. | |
| 2004/0030223 A1 | 2/2004 | Calafiore et al. | |
| 2004/0092799 A1 | 5/2004 | Hu et al. | |
| 2004/0143138 A1 | 7/2004 | Kunz et al. | |
| 2004/0171917 A1 | 9/2004 | Paul et al. | |
| 2004/0267097 A1 | 12/2004 | Xiao et al. | |
| 2005/0049463 A1* | 3/2005 | Arai | A61B 17/02 600/210 |
| 2005/0215851 A1* | 9/2005 | Kim | A61B 17/02 600/37 |
| 2006/0200005 A1 | 9/2006 | Bjork et al. | |
| 2006/0270909 A1* | 11/2006 | Davis | A61B 17/0218 600/210 |
| 2006/0270910 A1* | 11/2006 | Davis | A61B 17/0218 600/210 |
| 2007/0055108 A1 | 3/2007 | Taylor et al. | |
| 2007/0142712 A1 | 6/2007 | Phillips et al. | |
| 2007/0255109 A1 | 11/2007 | Stein et al. | |
| 2007/0260124 A1 | 11/2007 | Dobrovolny | |
| 2008/0071145 A1 | 3/2008 | Bjork et al. | |
| 2008/0108878 A1 | 5/2008 | Goodman et al. | |
| 2008/0139879 A1* | 6/2008 | Olson | A61B 17/02 600/37 |
| 2009/0254187 A1 | 10/2009 | Bjork | |
| 2010/0076266 A1* | 3/2010 | Boulais | A61B 1/00059 600/142 |
| 2010/0187065 A1* | 7/2010 | Pidgeon | A45F 5/021 190/115 |
| 2010/0210915 A1 | 8/2010 | Caldwell et al. | |
| 2010/0210916 A1 | 8/2010 | Hu et al. | |
| 2010/0240952 A1* | 9/2010 | Okazaki | A61B 1/0008 600/109 |
| 2010/0312069 A1* | 12/2010 | Sutherland | A61B 90/35 600/245 |
| 2010/0317925 A1 | 12/2010 | Banchieri et al. | |
| 2011/0028792 A1 | 2/2011 | Ibrahim et al. | |
| 2011/0028797 A1 | 2/2011 | Yee et al. | |
| 2011/0137130 A1 | 6/2011 | Thalgott et al. | |
| 2011/0270039 A1 | 11/2011 | Li | |
| 2012/0010629 A1* | 1/2012 | Mire | A61B 17/02 606/130 |
| 2012/0029271 A1* | 2/2012 | Meyer | A61B 17/0206 600/37 |
| 2012/0078061 A1* | 3/2012 | Calafiore | A61B 17/0206 600/229 |
| 2013/0221251 A1* | 8/2013 | Sandstrom | A61B 17/0218 251/11 |
| 2014/0121560 A1* | 5/2014 | Parks | A61B 10/0045 600/562 |

FOREIGN PATENT DOCUMENTS

| | | |
|---|---|---|
| JP | 2003529403 A | 10/2003 |
| JP | 2006-516910 A | 7/2006 |
| JP | 2007-508102 A | 4/2007 |
| WO | 1997/026828 A1 | 7/1997 |
| WO | 1998/049947 A1 | 11/1998 |
| WO | 1999/008585 A2 | 2/1999 |
| WO | 1999/009892 A1 | 3/1999 |
| WO | 1999/016367 A1 | 4/1999 |
| WO | 2001017437 A2 | 3/2001 |
| WO | 2001054562 A2 | 8/2001 |
| WO | 2003001969 A2 | 1/2003 |
| WO | 2011159733 A1 | 12/2011 |

OTHER PUBLICATIONS

Decision of Rejection issued in corresponding Japanese Patent Application No. 2013-515460 dated Sep. 6, 2016 (4 pages).
Decision of Rejection issued in corresponding Japanese Patent Application No. 2013-515460, dated Oct. 6, 2015, and an English Translation of same (12 pages).
International Preliminary Report on Patentability issued in International Application No. PCT/US2011/040399 dated Dec. 14, 2012.
Extended European Search Report issued in corresponding European Patent Application No. 16198830.8, dated Jun. 6, 2017.
Japanese Office Action (with English Translation) dated Feb. 5, 2019 for corresponding Japanese Patent Application No. 2017-211642, 6 pages.
Japanese Office Action (with English Translation) dated Aug. 28, 2018 for corresponding Japanese Patent Application No. 2017-211642, 7 pages.

* cited by examiner

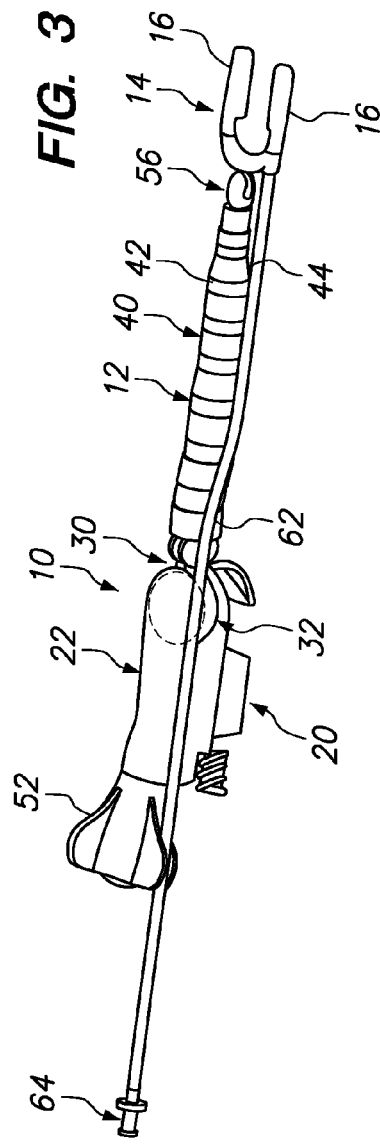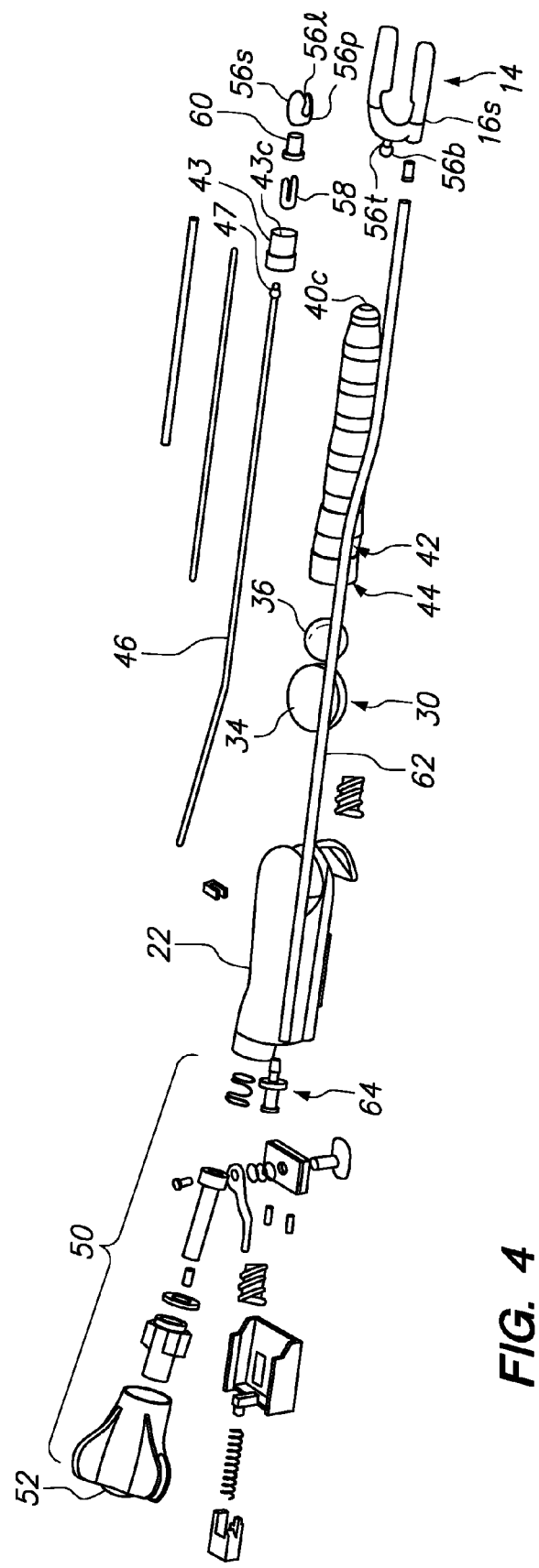

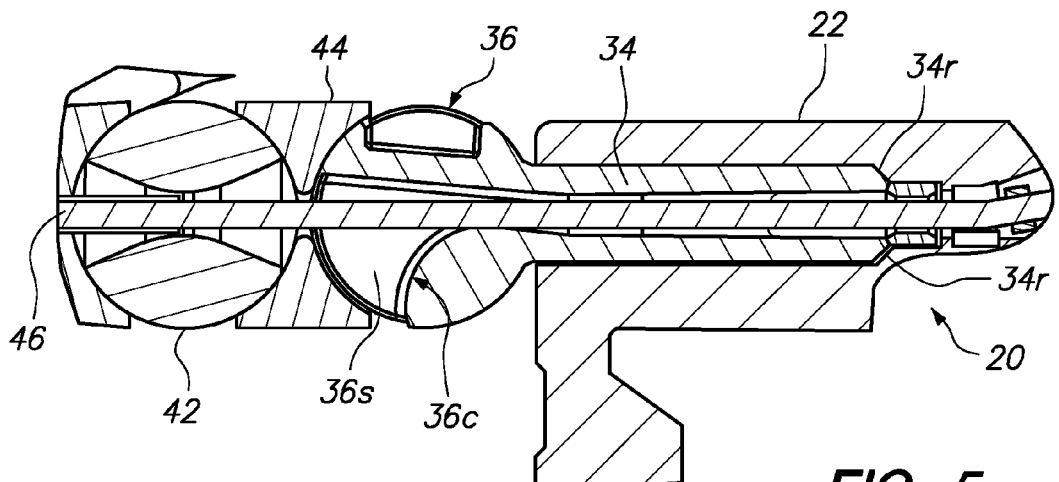
FIG. 5
FIG. 6
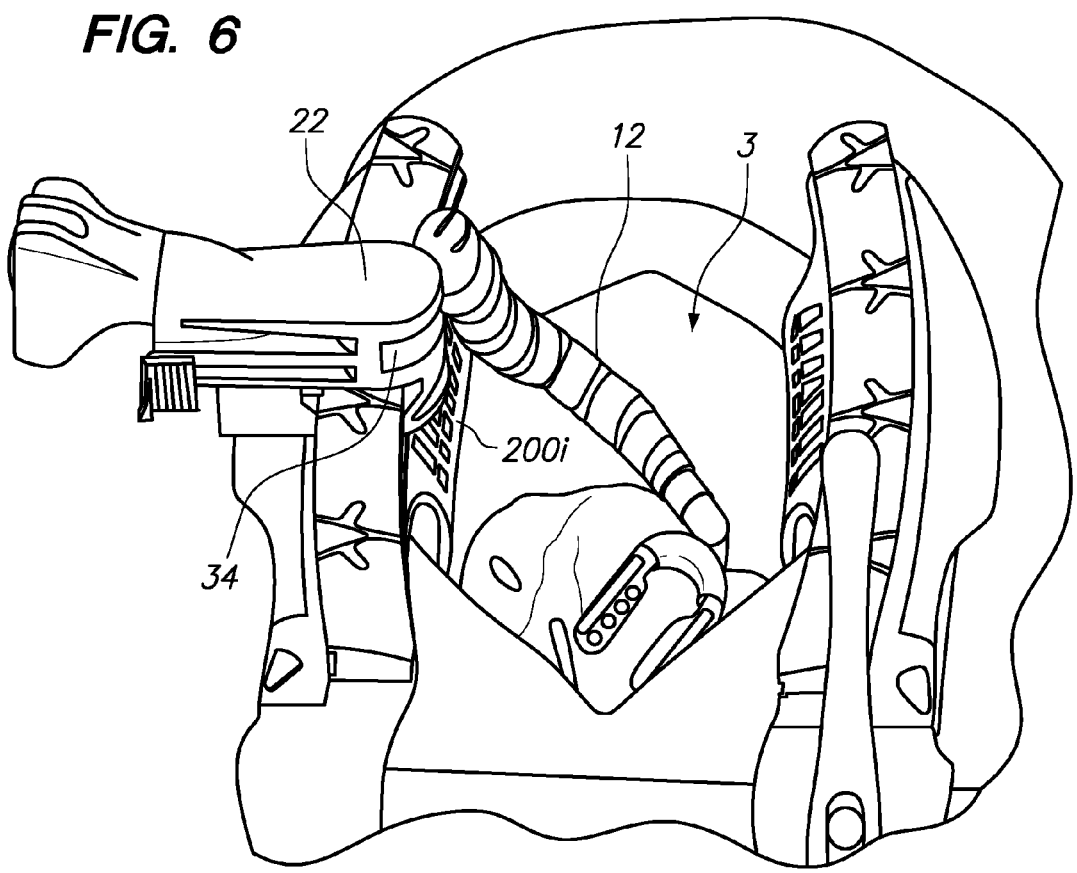

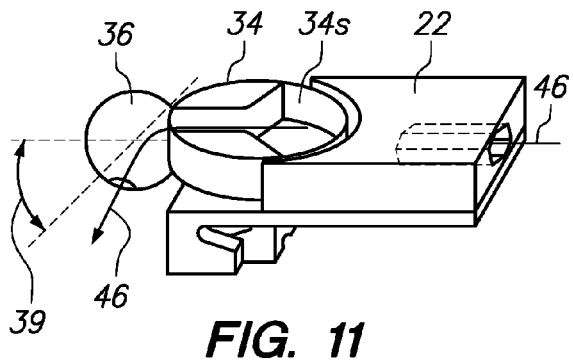
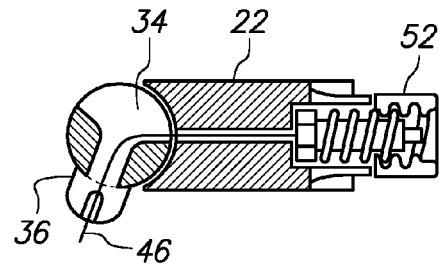
FIG. 11  FIG. 12
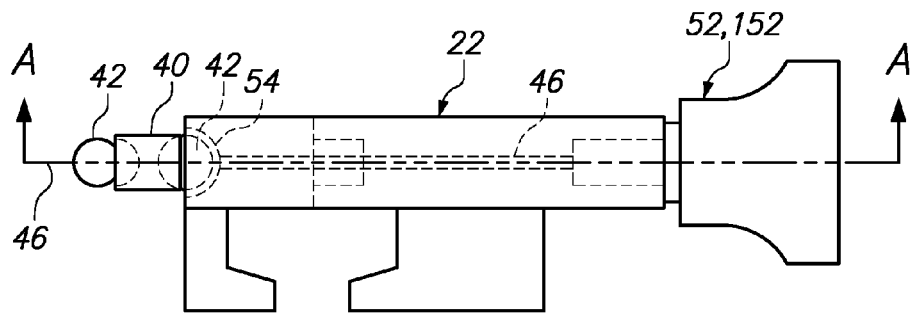
FIG. 13A
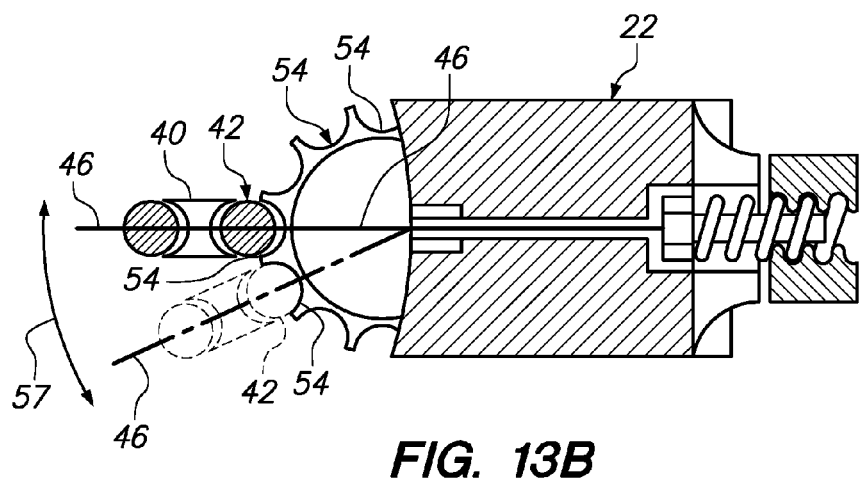
FIG. 13B

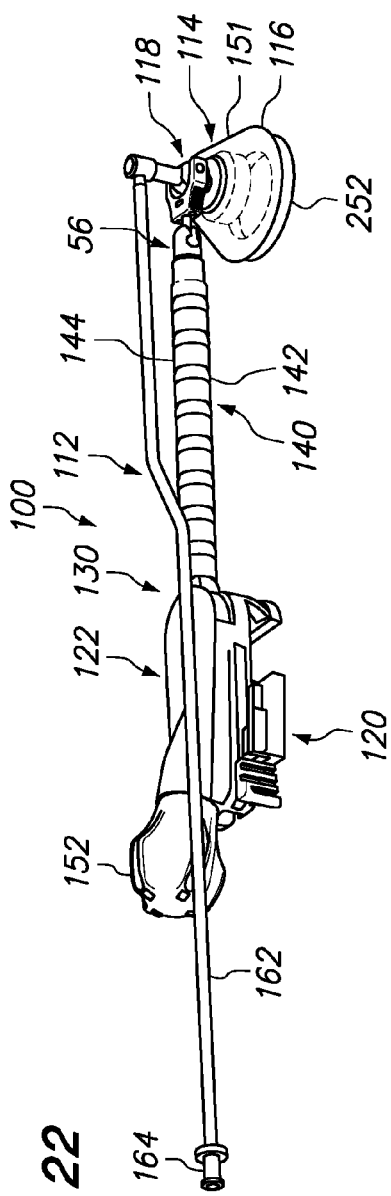
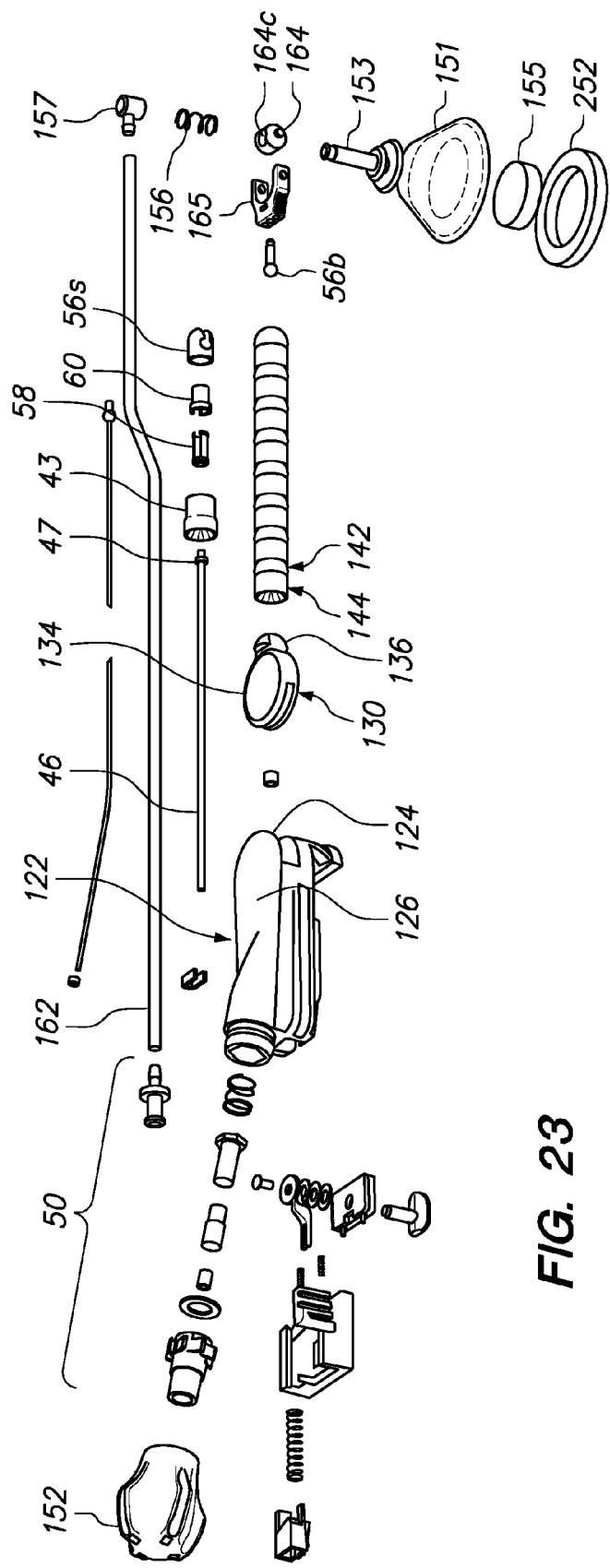

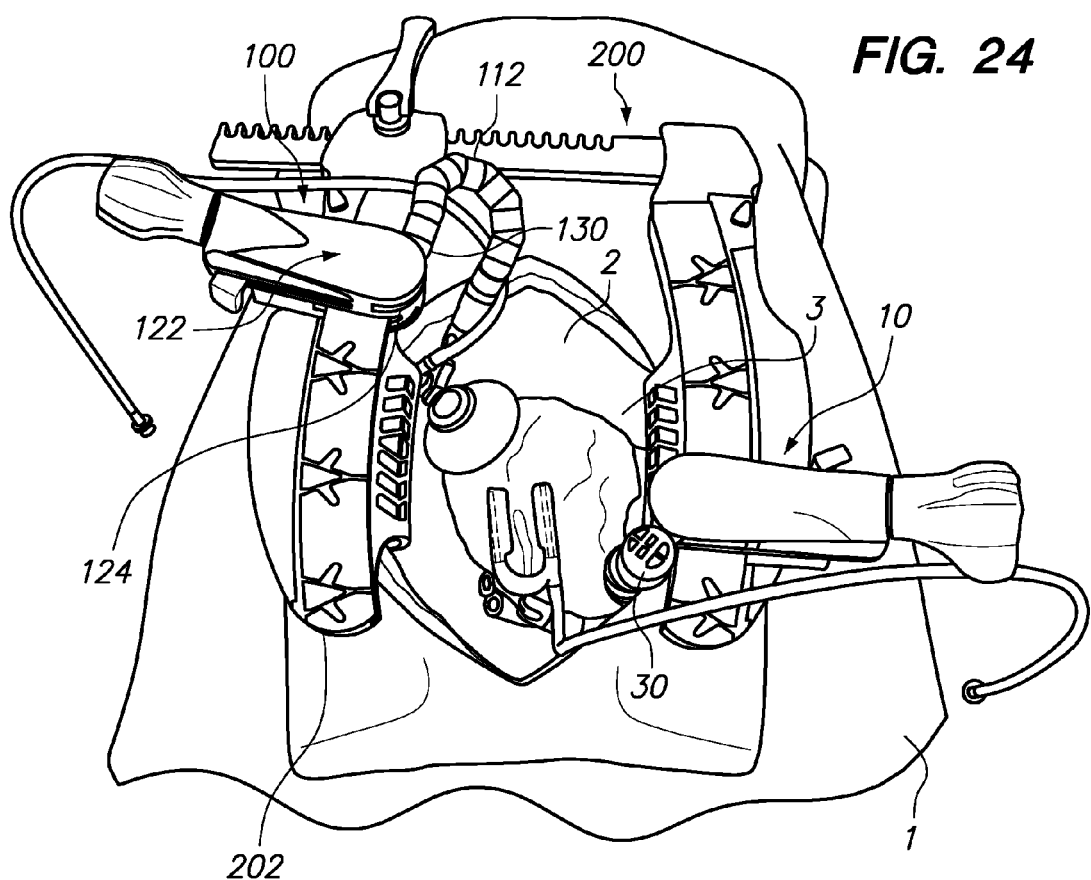
FIG. 24
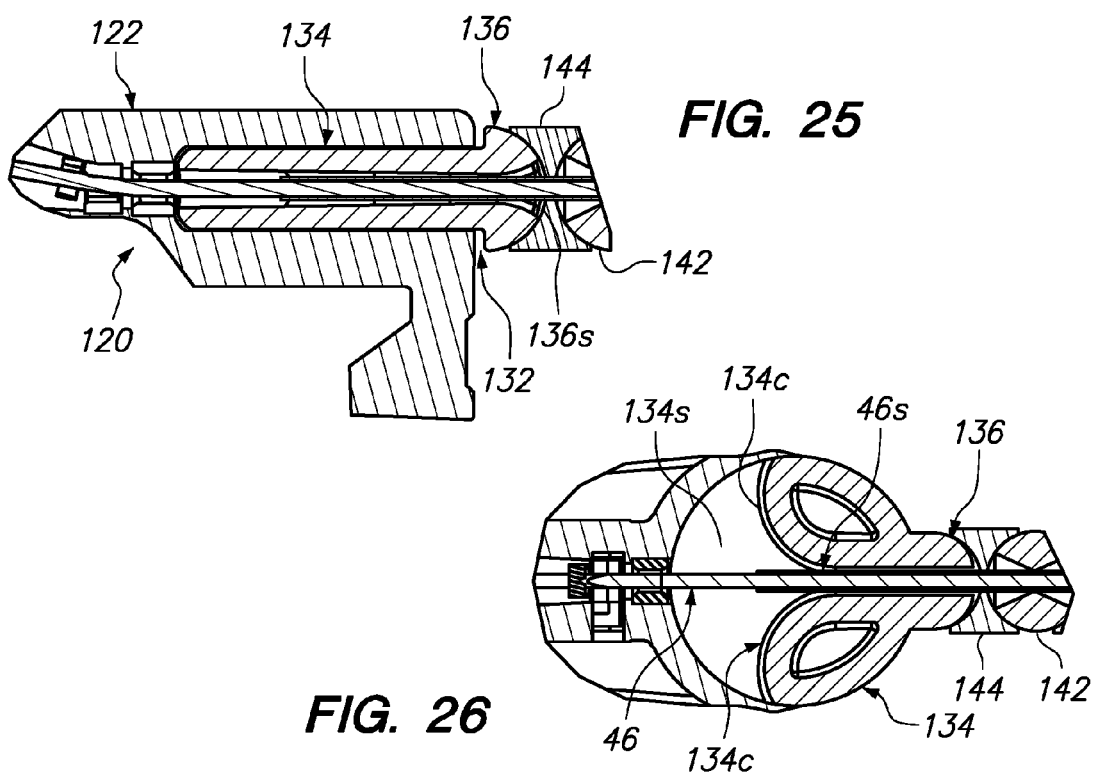
FIG. 25
FIG. 26

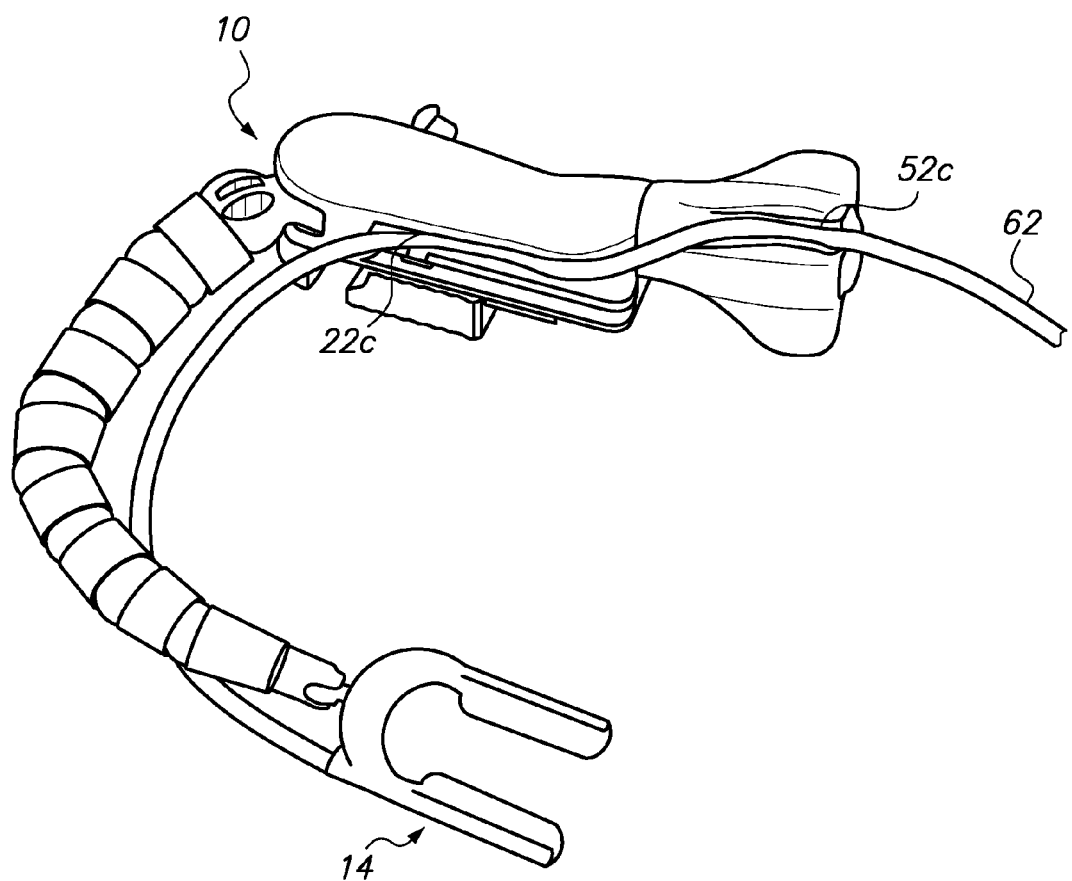
FIG. 29C
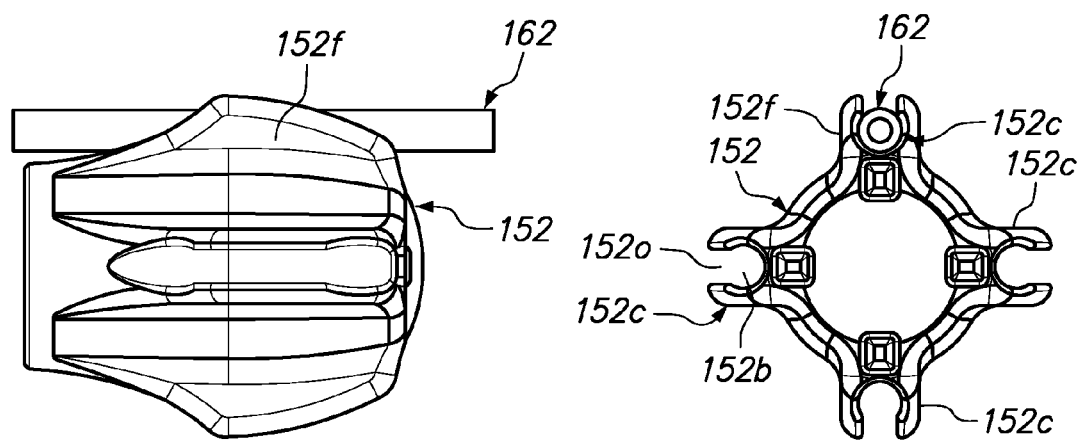
FIG. 30A  FIG. 30B

SURGICAL INSTRUMENTS, SYSTEMS AND METHODS OF USE

CROSS-REFERENCE TO RELATED APPLICATIONS

This application is a divisional application of U.S. Nonprovisional patent application Ser. No. 13/160,445 filed on Jun. 14, 2011, which claims priority to U.S. Provisional Patent Application Ser. No. 61/354,516, entitled "Surgical Instruments, Systems and Methods of Use" which was filed on Jun. 14, 2010. The content of the applications identified above are each incorporated herein by reference in their entirety.

FIELD OF THE INVENTION

The present invention relates generally to surgical instruments, and more particularly to surgical instruments useful for engaging surfaces of an organ, including organ stabilizer instruments and organ positioner instruments and their related components.

BACKGROUND OF THE INVENTION

Diseases of the cardiovascular system affect millions of people each year and are a leading cause of death throughout the world. The cost to society from such diseases is enormous both in terms of the number of lives lost as well as in terms of the costs associated with treating patients through traditional surgical techniques. A particularly prevalent form of cardiovascular disease is a reduction in the blood supply leading to the heart caused by atherosclerosis or other condition that creates a restriction in blood flow at a critical point in the vasculature supplying blood to the heart.

One option for treatment of such a blockage or restriction in the blood flow supplying the heart is a procedure known as a coronary artery bypass graft (CABG) surgery, more commonly known as a "heart bypass" operation. In the CABG procedure, the surgeon "bypasses" the obstruction to restore adequate blood flow to the heart either by attaching an available source vessel to the obstructed target coronary artery or by removing a portion of a vein or artery from another part of the body, to use as a graft, and installing the graft between a point on a source vessel and a point on a target artery.

To restore an adequate supply of blood to the heart, the CABG procedure requires that a fluid connection be established between two vessels. This procedure is known as an "anastomosis." Typically, a source vessel, such as a source artery with an unobstructed blood flow, i.e., the left or right internal mammary artery (IMA), or a bypass-graft having one end sewn to an unobstructed blood source such as the aorta, is sewn to a target occluded coronary artery, such as the left anterior descending (LAD) artery or other vessel that provides blood flow to the muscles of the heart.

Although the CABG procedure has become relatively common, the procedure itself is lengthy and traumatic and can damage the heart, the cardiovascular system, the brain, and the blood cells, as well as activate plasma cascade systems. In a conventional CABG procedure, the surgeon makes an incision down the center of the chest, cuts through the sternum, performs several other procedures necessary to attach the patient to a heart-lung bypass machine, cuts off the blood flow to the heart and then stops the heart from beating in order to complete the bypass. The most lengthy and traumatic surgical procedures are necessary, in part, to connect the patient to a cardiopulmonary bypass (CPB) machine to continue the circulation of oxygenated blood to the rest of the body while the bypass is completed.

In recent years, a growing number of surgeons have begun performing CABG procedures using surgical techniques especially developed so that the CABG procedure could be performed while the heart is still beating. In such procedures, there is no need for any form of cardiopulmonary bypass, and no need to stop the heart. As a result, these beating heart procedures are much less invasive and carry lower risk of post-operative neurological complications. In certain situations, the entire beating-heart CABG procedure can be performed through a small number, typically one or two, of comparatively small incisions in the chest, further reducing the risk of post-operative wound complications.

When CABG procedures are performed on a beating heart, a surgical stabilizer instrument is typically used to stabilize the heart tissue in the area of the anastomosis. Various surgical stabilizer instruments are available today. Typically the surgical stabilizer instrument will have some form of attachment mechanism that permits it to be fixed to the sternal retractor, so that it is maintained fixed relative to the tissue to be stabilized. One drawback of currently available stabilizer instruments is that they tend to extend too far across the open chest cavity and may obstruct movements of the surgeon's hands in some instances. Additionally, the arm and attachment mechanism also extend above the surface of the retractor and may also form an obstruction.

There is a continuing need for surgical stabilizer instruments having a lower profile and that can be extended into the chest cavity in a configuration that causes less obstruction to the operating surgeon.

When an anastomosis is to be performed on a surgical target area that is not readily accessible by the surgeon (e.g., one or more arteries of interest are located on the lateral or posterior aspects of the heart, making access to such arteries difficult), the heart is typically repositioned either by hand, by the surgeon or a surgeon's assistant, or, more commonly, by attachment of an organ positioner instrument to the heart, for repositioning and maintaining the heart in a displaced position via the organ positioner instrument.

Various organ positioner instruments are available today. Typically the organ positioner will have some form of attachment mechanism that permits it to be fixed to the sternal retractor, so that it is can be supported by the sternal retractor while it is maintaining the organ in the displaced position.

One drawback of currently available organ positioner instruments, is that they tend to extend too far across the open chest cavity and may obstruct movements of the surgeon's hands in some instances, and may prevent viewing of some areas in the surgical field.

There is a continuing need for organ positioner instruments that can be extended into the chest cavity in a configuration that causes less obstruction to the operating surgeon.

The present invention meets these needs as well as providing additional improved features that will become apparent upon reading the detailed description below.

SUMMARY OF THE INVENTION

A surgical instrument according to an example embodiment of the present invention comprises: a mount body having a top portion, a distal end, a proximal end and a bottom portion; a joint member pivotally mounted at a distal end portion of the mount body to allow positioning of a proximal portion of an arm extending distally from the joint member, the joint member configured to at least partially constrain movement of the proximal portion of the arm to a plane; and a working end mounted to a distal end portion of the arm.

According to an example embodiment, the joint member comprises a first joint member and a second joint member, wherein the first joint member confines movement of the proximal portion of the arm to yawing, and the second joint member confines movement of the proximal portion of the arm to pitching.

According to an example embodiment, the joint member pivotally mounted at the distal end portion of the mount body is a disk member.

According to an example embodiment, the joint member further comprises a slotted ball.

According to an example embodiment, the joint member is a disk member, and the slotted ball is connected to said disk member.

According to an example embodiment, further comprising an actuator rotatably mounted to the mount body towards the proximal end of the mount body, and a cable extending from the actuator through the mount body, joint member, slotted ball and arm, the actuator and the cable being configured to change a state of the arm from a flexible state to a rigid state by movement of the actuator in a first direction, and from the rigid state to the flexible state by movement of the actuator is a second direction opposite the first direction.

According to an example embodiment, movement of the actuator involves rotation, the first direction is a first rotational direction, and the second direction is a counter-rotational direction.

According to an example embodiment, the slotted ball member forms a joint with a proximal end of the arm.

According to an example embodiment, upper and lower surfaces of the disk member extend substantially parallel with the top portion of the mount body, and wherein the slotted ball is capable of pivoting to an angularly downward position from a plane parallel to the upper and lower surfaces of the disk member.

According to an example embodiment, the instrument comprising a vacuum tube in fluid communication with the working end, and the working end is configured to reversibly attach to the exterior surface of a human's heart.

According to an example embodiment, the instrument comprises an actuator rotatably mounted to the mount body at the proximal end of the mount body, the actuator being configured to change a state of the arm from a flexible state to a rigid state by rotation of the actuator in a first rotational direction, and from the rigid state to the flexible state by rotation of the actuator in a counter-rotational direction.

According to an example embodiment, the instrument comprises a suction tube in fluid communication with the working end, and a clip configured to receive and temporarily hold the suction tube to maintain the suction tube in a low profile with the instrument, wherein the clip is formed with or connected to the mount body, the actuator, or both the mount body and the actuator.

According to an example embodiment, the actuator comprises a plurality of fins with one of the clips formed in one or more of the fins.

According to an example embodiment, the instrument is an organ stabilizer and the working end comprises at least one contact member configured to be exerted against a tissue surface to stabilize the tissue surface.

According to an example embodiment, the instrument is an organ positioner and the working end comprises a suction member defining a vacuum space therein, wherein the suction member is configured to receive the apex of a human heart.

According to an example embodiment, the instrument is further configured to exert sufficient suction force on the heart to move the heart when the suction member is placed against the heart, a negative pressure of 250 millimeters of Mercury is applied within the vacuum space to engage the suction member with the heart, and the suction member is moved.

According to an example embodiment, the bottom portion comprises a mounting mechanism configured to reversibly clamp the instrument to a fixed object.

According to an example embodiment, the mounting mechanism is fixed to a surface of a sternal retractor, the sternal retractor comprising a sternal retractor blade mounted to or integral with the sternal retractor, wherein the arm is capable of being oriented downwardly to make contact with an inner surface of a sternal retractor blade without requiring the movement of the actuator with respect to the mounting body.

According to an example embodiment, the mounting mechanism comprises a fixed jaw and a movable jaw; and wherein a mounting mechanism actuator is pivotally mounted within the bottom portion and at least partially above the movable jaw, the mounting mechanism actuator being configured to move the movable jaw from an unlocked position to a locked position and vice versa.

According to an example embodiment, the mounting mechanism actuator is configured to move the movable jaw toward the locked position when the mounting mechanism actuator is pulled in a proximal direction.

According to an example embodiment, the mounting mechanism comprises a fixed jaw that is unitarily formed with the main body, and a movable jaw movably engaged to the main body.

According to an example embodiment, the instrument comprises a cam mounted above a bottom surface of the movable jaw and below the mounting mechanism actuator, the cam connected to the mounting mechanism actuator to be actuated to lock or unlock the movable jaw.

According to an example embodiment, the mounting mechanism comprises a mounting mechanism actuator, the mounting mechanism actuator including rocker switches with cams configured to clamp to the fixed object.

According to an example embodiment, the instrument is a stabilizer and the working end comprises a pair of contact members and a blower/mister device incorporated into at least one of the contact members.

According to an example embodiment, the instrument is a stabilizer configured for a blower/mister device to be attached thereto.

According to an example embodiment, the instrument is a stabilizer and the working end comprises a pair of contact members and a support to link the contact members to the arm, wherein the support is pivotally linked to the contact members.

According to an example embodiment, the contact members each comprise a clip at a proximal end portion thereof, the clips configured to form a snap fit with the support members.

According to an example embodiment, the instrument is a stabilizer and the working end comprises a pair of contact members, the contact members each having a relatively thicker cross-sectional dimension at an outside edge thereof and a relatively thinner cross-sectional dimension at an inside edge thereof.

According to an example embodiment, the arm comprises an intermediate link that is adjustable by a user to adjust a portion of the arm distal of the intermediate link and the working member to assume a flexible configuration in a first configuration, and to assume a rigid configuration in a second configuration, while allowing a portion of the arm proximal of the intermediate link to remain flexible during both the first configuration and the second configuration.

According to an example embodiment, the arm comprises an intermediate link that is adjustable by a user to adjust a portion of the arm proximal of the intermediate link to assume a flexible configuration in a first configuration, and to assume a rigid configuration in a second configuration, while allowing a portion of the arm distal of the intermediate link and the working end to remain flexible during both the first configuration and the second configuration.

According to an example embodiment, the instrument comprises a motor configured to operate the actuator, and a second actuator, located distally of the actuator and the motor, electrically connected to the motor, and configured to actuate the motor to drive the actuator to increase or decrease rigidity in the arm and a connection between the arm and the working end.

According to an example embodiment, the top portion is smooth and comprises a flat portion with no obstructions thereon, and wherein the top surface provides a rest for a surgeon's hand, that can be used to help stabilize the surgeon's hand.

According to an example embodiment, ridges or teeth provided around at least a portion of a perimeter of the disk member.

According to an example embodiment, the instrument a cable extending through the disk member, at least a portion of the arm, and at least a portion of the mount body, wherein the disk member comprises a slot formed therein, the slot being curved to facilitate bending and tightening of the cable thereagainst when the disk member has been pivoted, thereby helping to eliminate or reduce variations in at least one of cable length and cable tension at different angular positions of the disk member relative to the mount body.

According to an example embodiment, the disk member comprises a slot formed therein, the slot being curved to facilitate bending and tightening of the cable thereagainst when the disk member has been pivoted, thereby helping to eliminate or reduce variations in at least one of cable length and cable tension at different angular positions of the disk member relative to the mount body.

According to an example embodiment, the instrument comprises an actuator rotatably mounted to the mount body at the proximal end of the mount body and a cable extending from the actuator through the mount body, disk member, slotted ball and arm, the actuator and the cable being configured to change a state of the arm from a flexible state to a rigid state by rotation of the actuator in a first rotational direction, and from the rigid state to the flexible state by rotation of the actuator in a counter-rotational direction.

According to an example embodiment, the instrument comprises a canister in fluid communication with the vacuum tube, the canister having an opening for connecting the canister in fluid communication with a vacuum source, the canister configured to trap fluid therein.

According to an example embodiment, the instrument comprises a filter in fluid communication with the opening of the canister, the filter configured to be connected to the vacuum source and to filter particulates from effluent from the canister.

According to an example embodiment, the canister has at least one substantially flat side.

According to an example embodiment, the instrument comprises a strap connected to the canister and adapted to hang the canister in an upright orientation wherein the opening for connecting the canister with a vacuum source is higher than a connection forming the fluid communication of the canister with the vacuum tube.

According to an example embodiment, a surface of the canister is matted to inhibit glare reflection therefrom.

A surgical instrument according to an example embodiment of the present invention comprises: a mount body, an arm, and a tool; the mount body configured to be used with a retractor, a bottom surface of the mount body facing the retractor when mounted, a front edge of the mount body running at an angle to the bottom surface; the arm pivotally connected on a proximal end thereof via the end joint to the front edge of the mount body; the tool connected to a distal end of the arm; the arm configured to be movable between a plurality of positions relative to the mount body and to be temporarily lockable in these positions.

According to an example embodiment, the joint configured such that a proximal portion of the arm extending from or adjacent to the mount body is pivotable to the mount body and temporarily lockable in a position substantially perpendicular to the mount body.

According to an example embodiment, the joint configured such that a proximal portion of the arm extending from and adjacent the mount body is movable from a left distal region of the mount body to a right distal region of the mount body and vice versa.

A surgical instrument according to an example embodiment of the present invention comprises: a mount body, an arm, a tool and a tube; the mount body configured to mount to a retractor or a surgical table; the arm pivotally connected on a proximal end to the mount body; the tool connected to a distal end of the arm; the arm configured to be movable between a plurality of positions relative to the mount body and to be temporarily lockable in these positions; a distal end of the tube connected at or adjacent a distal end of the arm; and the mount body configured to removably retain the tube.

According to an example embodiment, the mount body includes a recess sized to receive and removably retain the tube.

According to an example embodiment, the mount body includes a clip sized to receive and removably retain the tube.

According to an example embodiment, the mount body further comprising an actuator rotatably mounted to the surgical instrument, the actuator being configured to change a state of the arm form a flexible state to a rigid state by rotation of the actuator in a first rotational direction, and from the rigid state to the flexible state by rotation of the actuator in a counter-rotational direction; and the actuator configured to removably retain the tube.

An example method of operating a surgical instrument according to the present invention comprises the steps of attaching a mount body of the instrument to a fixed object so that the mount body is not movable relative to the fixed object; adjusting an orientation of an arm that extends from a distal end of the mount body; and rotating an actuator rotatably mounted to a proximal end of the mount body, thereby fixing the orientation of the arm with respect to the mount body in a rigid configuration.

According to an example embodiment, a tensioning cable extends through at least portions of the proximal half of arm and the mount body and connects with the actuator, and the rotation of the actuator increases tension in the cable.

According to an example embodiment, the fixed object is a sternal retractor and the arm contacts an inner surface of the sternal retractor in the rigid configuration.

According to an example embodiment, the instrument is a surgical stabilizer.

According to an example embodiment, the instrument is a surgical stabilizer for beating heart surgery, or an organ positioner for beating heart surgery.

A surgical instrument according to an example embodiment of the present invention comprises: a mount body, an arm, a joint, and a tool; the mount body configured to mount to a retractor, a bottom surface of the mount body facing the retractor when mounted, a front edge of the mount body running at an angle to the bottom surface; the arm pivotally connected on a proximal end of the arm via the joint to or along the front edge of the mount body; the tool connected to a distal end of the arm; the arm configured to be movable between a plurality of positions relative to the mount body and to be temporarily lockable in these positions; and the joint configured such that a proximal portion of the arm extending from and adjacent the mount body is pivotable to and temporarily lockable in a position substantially perpendicular to the mount body along portions of the front edge.

According to an example embodiment, the surgical instrument further comprises a universal connector configured to connect the mount body to any one of a plurality of retractors of different size.

According to an example embodiment, the joint includes a disk member.

According to an example embodiment, the joint includes a slotted ball.

A surgical instrument according to an example embodiment of the present invention comprises: an actuator rotatably mounted to the mount body at the proximal end of the mount body and a cable extending from the actuator through the mount body, disk member, slotted ball and arm, and the actuator and the cable are configured to change a state of the arm from a flexible state to a rigid state by rotation of the actuator in a first rotational direction, and from the rigid state to the flexible state by rotation of the actuator in a counter-rotational direction.

According to an example embodiment, a tube is provided in fluid communication with the tool.

According to an example embodiment, a tube is provided in fluid communication with the tool, and the actuator includes a clip configured to receive and temporarily hold the tube to maintain the tube in a low profile arrangement with the instrument.

According to an example embodiment, the mount body includes a recess sized to receive and removably retain the tube.

According to an example embodiment, the instrument is a stabilizer and the tool comprises at least one contact member configured to be exerted against a tissue surface to stabilize the tissue surface.

According to an example embodiment, the instrument is a positioner and the tool comprises a suction member defining a vacuum space therein, wherein the suction member is configured to exert sufficient suction force on an organ to move the organ when the suction member is placed against the organ, a negative pressure is applied within the vacuum space to engage the suction member with the organ, and the suction member is moved.

According to an example embodiment, the instrument includes a cable extending through the disk member, at least a portion of the arm and at least a portion of the mount body, wherein the disk member comprises a slot formed therein, the slot being curved to facilitate bending and tightening of the cable thereagainst when the disk member has been pivoted, thereby helping to eliminate or reduce variations in at least one of cable length and cable tension at different angular positions of the disk member relative to the mount body.

According to an example embodiment, an actuator is rotatably mounted to the mount body at the proximal end of the mount body and a cable extends from the actuator through the mount body, disk member, slotted ball and arm.

According to an example embodiment, the actuator and the cable are configured to change a state of the arm from a flexible state to a rigid state by rotation of the actuator in a first rotational direction, and from the rigid state to the flexible state by rotation of the actuator in a counter-rotational direction.

According to an example embodiment, a canister is provided in fluid communication with the tube, the canister having an opening for connecting the canister in fluid communication with a vacuum source, the canister configured to trap fluid therein.

According to an example embodiment, a filter is in fluid communication with the opening of the canister, and the filter is configured to be connected to the vacuum source and to filter particulates from effluent from the canister.

According to an example embodiment, a strap is connected to the canister and adapted to hang the canister in an upright orientation wherein the opening for connecting the canister with a vacuum source is higher than a connection forming the fluid communication of the canister with the vacuum tube.

According to an example embodiment, a surgical instrument is provided that includes a mount body, an arm, a tool, and a tube; the mount body configured to mount to a retractor or a surgical table; the arm pivotally connected on a proximal end to the mount body; the tool connected to a distal end of the arm; the arm configured to be movable between a plurality of positions relative to the mount body and to be temporarily lockable in these positions; a distal end of the tube connected at or adjacent a distal end of the arm; and the mount body configured to removably retain the tube.

A surgical instrument according to an example embodiment of the present invention comprises: a mount body having a top portion, a distal end, a proximal end and a bottom portion; a plurality of mount body jaws formed by or connected to the bottom portion; a joint member engaged to an arm, the arm extending distally from the joint member and terminating with a working end mounted to a distal end portion of the arm, the joint member pivotally mounted at a distal end portion of the mount body; wherein the arm through positioning of the joint member is capable of being positioned towards the left or right distal regions of the mount body without interfering with a space located above the mount body jaws and immediately dorsal to the top portion of the mount body.

According to an example embodiment, the joint member is capable of being positioning with constrained movement of at least a portion of the joint member with respect to a plane horizontally aligned with respect to the top portion of the mount body.

According to an example embodiment, the working end is configured for attachment to the surface of a heart, the working end further including a stabilizer member to engage one or both sides of a coronary artery, or a positioner member capable of receiving the apex of the heart.

A surgical instrument according to an example embodiment of the present invention comprises: a flexible arm comprising a distal end, a proximal end, and a plurality of joint members located therebetween whereby at least a portion of adjoining joint members can form articulating joints; a working end configured to engage a surface of a human's heart, wherein the working end is connected to the distal end of the flexible arm; and a mount body joint forming a mount body angle between the proximal end of the flexible arm and a mount body, a minimum mount body angle being at most than 120 degrees, wherein a reference angle is defined as 180 degrees between any two unstressed articulating joint members.

According to an example embodiment, the minimum mount body angle is greater than 105 degrees.

According to an example embodiment, the mount body joint is comprised of a horizontal joint and a vertical joint, wherein the horizontal joint is configured for controlled planar translation or pivoting along a first plane that is substantially horizontal, and the vertical joint is configured for generally planar translation or pivoting along a second plane that is substantially perpendicular to the first plane.

A surgical instrument according to an example embodiment of the present invention comprises: a flexible arm comprising a distal end, a proximal end, and a plurality of joint members located therebetween whereby at least a portion of adjoining joint members can form articulating joints, the articulating joints capable of establishing a plurality of arm joint angles each having a minimum achievable angle value, the angle being defined as 180 degrees between any two unstressed articulating joints; a working end configured to engage a surface of a human's heart, wherein the working end is connected to the distal end of the flexible arm; and a mount body joint forming a mount body angle between the proximal end of the flexible arm and a mount body, a minimum mount body angle being a substantially smaller angle than a smallest of the minimum achievable angle values.

A surgical instrument according to an example embodiment of the present invention comprises: a mount body having a top portion, a distal end, a proximal end and a bottom portion and connected to a joint member; a mount body jaw formed by or connected to the bottom portion; the joint member engaged to a proximal portion of an arm that extends distally from the joint member and terminates with a working end, the joint member being pivotally mounted at a distal end portion of the mount body; wherein the joint member prohibits a proximal portion of the arm from extending above the top portion of the mount body.

A surgical instrument according to an example embodiment of the present invention comprises: a mount body having a top surface, a distal end, a proximal end and a bottom portion; a joint member including a disk member pivotally mounted in a distal end portion of the mount body; an arm extending distally from the disk member; and a working end mounted to a distal end portion of the arm.

According to an example embodiment, the joint member forms a joint with a proximal end of the arm.

According to an example embodiment, the joint member includes a slotted ball.

According to an example embodiment, the slotted ball is fixed to the disk member.

According to an example embodiment, the instrument includes an actuator rotatably mounted to the mount body at the proximal end of the mount body and a cable extending from the actuator through the mount body, disk member, slotted ball and arm, and the actuator and the cable are configured to change a state of the arm from a flexible state to a rigid state by rotation of the actuator in a first rotational direction, and from the rigid state to the flexible state by rotation of the actuator in a counter-rotational direction.

According to an example embodiment, the slotted ball forms a joint with a proximal end of the arm.

According to an example embodiment, upper and lower surfaces of the disk member extend substantially parallel with the top surface of the mount body, and the ball extends angularly downward from a plane parallel to the upper and lower surfaces.

According to an example embodiment, a vacuum tube is provided in fluid communication with the working end.

According to an example embodiment, an actuator is rotatably mounted to the mount body at the proximal end of the mount body. The actuator is configured to change a state of the arm from a flexible state to a rigid state by rotation of the actuator in a first rotational direction, and from the rigid state to the flexible state by rotation of the actuator in a counter-rotational direction.

According to an example embodiment, a suction tube is provided in fluid communication with the working end, and the actuator includes a clip configured to receive and temporarily hold the suction tube to maintain the suction tube in a low profile with the instrument.

According to an example embodiment, the actuator comprises a plurality of fins with one of the clips formed in each of the fins.

According to an example embodiment, the instrument is a stabilizer and the working end comprises at least one contact member configured to be exerted against a tissue surface to stabilize the tissue surface.

According to an example embodiment, the instrument is a positioner and the working end comprises a suction member defining a vacuum space therein, wherein the suction member is configured to exert sufficient suction force on an organ to move the organ when the suction member is placed against the organ, a negative pressure is applied within the vacuum space to engage the suction member with the organ, and the suction member is moved.

According to an example embodiment, the bottom portion comprises a mounting mechanism configured to clamp the instrument to a fixed object.

According to an example embodiment, the mounting mechanism is fixed to a blade of a sternal retractor and the arm is oriented downwardly and in contact with an inner surface of the sternal retractor blade.

According to an example embodiment, the mounting mechanism comprises a fixed jaw and a movable jaw; and a mounting mechanism actuator is pivotally mounted within the bottom portion above the movable jaw. The mounting mechanism actuator is configured to move the movable jaw from an unlocked position to a locked position and vice versa.

According to an example embodiment, the mounting mechanism actuator is configured to move the movable jaw toward the locked position when the mounting mechanism actuator is pulled in a proximal direction.

According to an example embodiment, a cam is mounted above a bottom surface of the movable jaw and below the mounting mechanism actuator. The cam is connected to the mounting mechanism actuator to be actuated to lock or unlock the movable jaw.

According to an example embodiment, the mounting mechanism comprises a mounting mechanism actuator, and the mounting mechanism actuator includes rocker switches with cams configured to clamp to the fixed object on opposite side of the fixed object.

According to an example embodiment, the instrument is a stabilizer and the working end comprises a pair of contact members and a blower/mister device incorporated into at least one of the contact members.

According to an example embodiment, the instrument is a stabilizer and the working end comprises a pair of contact members and the stabilizer is configured for a blower/mister device to be attached thereto.

According to an example embodiment, the instrument is a stabilizer and the working end comprises a pair of contact members and supports linking the contact members to the arm, wherein the supports are pivotally linked to the contact members.

According to an example embodiment, the contact members each comprise a clip at a proximal end portion thereof, and the clips are configured to form a snap fit with the support members.

According to an example embodiment, the instrument is a stabilizer and the working end comprises a pair of contact members. The contact members each have a relatively thicker cross-sectional dimension at an outside edge thereof and a relatively thinnest cross-sectional dimension at an inside edge thereof.

According to an example embodiment, the arm comprises an intermediate link that is adjustable by user to adjust a portion of the arm distal of the intermediate link and the working member to assume a flexible configuration in a first configuration, and to assume a rigid configuration in a second configuration, while allowing a portion of the arm proximal of the intermediate link to remain flexible during both the first configuration and the second configuration.

According to an example embodiment, the arm comprises an intermediate link that is adjustable by a user to adjust a portion of the arm proximal of the intermediate link to assume a flexible configuration in a first configuration, and to assume a rigid configuration in a second configuration, while allowing a portion of the arm distal of the intermediate link and the working end to remain flexible during both the first configuration and the second configuration.

According to an example embodiment, a motor is configured to operate the actuator, and a second actuator is provided. The second actuator is located distally of the actuator and the motor, and is electrically connected to the motor, and configured to actuate the motor to drive the actuator to increase or decrease rigidity in the arm and a connection between the arm and the working end.

According to an example embodiment, the top surface of the mount body is smooth and flat with no obstructions thereon, and the top surface provides a rest for a surgeon's hand, that can be used to help stabilize the surgeon's hand.

According to an example embodiment, ridges or ratchet teeth are provided around a least a portion of a perimeter of the disk member.

According to an example embodiment, the instrument includes a cable extending through the disk member, at least a portion of the arm and at least a portion of the mount body, wherein the disk member comprises a slot formed therein, the slot being curved to facilitate bending and tightening of the cable thereagainst when the disk member has been pivoted, thereby helping to eliminate or reduce variations in at least one of cable length and cable tension at different angular positions of the disk member relative to the mount body.

According to an example embodiment, the disk member comprises a slot formed therein, the slot being curved to facilitate bending and tightening of the cable thereagainst when the disk member has been pivoted, thereby helping to eliminate or reduce variations in at least one of cable length and cable tension at different angular positions of the disk member relative to the mount body.

According to an example embodiment, an actuator is rotatably mounted to the mount body at the proximal end of the mount body and a cable extends from the actuator through the mount body, disk member, ball and arm. The actuator and the cable are configured to change a state of the arm from a flexible state to a rigid state by rotation of the actuator in a first rotational direction, and from the rigid state to the flexible state by rotation of the actuator in a counter-rotational direction.

According to an example embodiment, the suction/vacuum tube comprises a color-coded connector at a proximal end thereof, the connector configured to be connected to a source of vacuum or another vacuum line in fluid communication with a source of vacuum.

According to an example embodiment, a canister is provided in fluid communication with the suction/vacuum tube, the canister having an opening for connecting the canister in fluid communication with a vacuum source, the canister configured to trap fluid therein.

According to an example embodiment, a filter is in fluid communication with the opening of the canister, and the filter is configured to be connected to the vacuum source and to filter particulates from effluent from the canister.

According to an example embodiment, the canister has at least one substantially flat side.

According to an example embodiment, a strap is connected to the canister and adapted to hang the canister in an upright orientation wherein the opening for connecting the canister with a vacuum source is higher than a connection forming the fluid communication of the canister with the vacuum tube.

According to an example embodiment, a surface of the canister is matted to inhibit glare reflection therefrom.

In another aspect of the present invention, a method of operating a surgical instrument is provided, including: attaching a mount body of the instrument to a fixed object so that the mount body is not movable relative to the fixed object; adjusting an orientation of an arm that extends from a distal end of the mount body; and rotating an actuator rotatably mounted to a proximal end of the mount body, thereby fixing the orientation of the arm in a rigid configuration.

According to an example embodiment, a tensioning cable extends through the arm and the mount body and connects with the actuator, and the rotation of the actuator increases tension in the cable.

According to an example embodiment, the fixed object is a sternal retractor and the arm contacts an inner surface of the sternal retractor in the rigid configuration.

According to an example embodiment, the instrument is a surgical stabilizer.

According to an example embodiment, the instrument is an organ positioner.

In another aspect of the present invention, a surgical system is provided that includes: a surgical retractor having at least one rail adapted to mount surgical instruments thereto; a positioner comprising: a first body having a top surface, a first distal end, a first proximal end and a first bottom portion, wherein the first bottom portion comprises a first mounting mechanism configured to clamp the positioner to the at least one rail, wherein the first mounting mechanism comprises a first fixed jaw and a first movable jaw; and wherein a first mounting mechanism actuator is pivotally mounted within the first bottom portion above the first movable jaw, the first mounting mechanism actuator being configured to move the first movable jaw from an unlocked position to a locked position and vice versa, wherein the first mounting mechanism actuator is configured to move the first movable jaw toward the locked position when the first mounting mechanism actuator is pulled in a proximal direction, wherein a first cam is mounted above a bottom surface of the first movable jaw and below the first mounting mechanism actuator, the first cam connected to the first mounting mechanism actuator to be actuated to lock or unlock the movable jaw, wherein the first top surface is smooth and substantially flat with no obstructions thereon, and wherein the first top surface provides a rest for a surgeon's hand, that can be used to help stabilize the surgeon's hand; a first joint member including a first disk member pivotally mounted in a distal end portion of the first mount body and a first slotted ball fixed to the first disk member; a first arm extending distally from the first joint, wherein the first joint member forms a joint with a proximal end of the first arm; a suction member defining a vacuum space therein, wherein the suction member is configured to exert sufficient suction force on an organ to move the organ when the suction member is placed against the organ, a negative pressure is applied within the vacuum space to engage the suction member with the organ, and the suction member is moved; a first actuator rotatably mounted to the first mount body at the proximal end of the first mount body and a first cable extending from the first actuator through the first mount body, first disk member, first slotted ball and first arm, the first actuator and the first cable being configured to change a state of the first arm from a flexible state to a rigid state by rotation of the first actuator in a first rotational direction, and from the rigid state to the flexible state by rotation of the first actuator in a counter-rotational direction, wherein the first disk member comprises a first slot formed therein, the first slot being curved to facilitate bending and tightening of the cable thereagainst when the first disk member has been pivoted, thereby helping to eliminate or reduce variations in at least one of first cable length and first cable tension at different angular positions of the first disk member relative to the first mount body; and a first vacuum tube in fluid communication with the suction member, wherein the first actuator comprises a clip configured to receive and temporarily hold the first suction tube to maintain the first suction tube in a low profile with the positioner; wherein the first actuator comprises a plurality of first fins with one of the clips formed in each of the fins, and wherein the first vacuum tube comprises a first color-coded connector at a proximal end thereof, the first color-coded connector configured to be connected to a source of vacuum or another vacuum line in fluid communication with a source of vacuum; a first canister in fluid communication with the first vacuum tube via the first color-coded connector, the first canister having a first opening for connecting the first canister in fluid communication with the first vacuum source, the first canister configured to trap fluid therein, wherein the first canister has at least one substantially flat side, and wherein a surface of the first canister is matted to inhibit glare reflection therefrom; a first strap connected to the first canister and adapted to hang the first canister in an upright orientation wherein the first opening for connecting the first canister with the first vacuum source is higher than a first connection forming the fluid communication of the first canister with the first vacuum tube; a first filter in fluid communication with the first opening of the first canister, the first filter configured to be connected to the first vacuum source and to filter particulates from effluent from the first canister; a stabilizer comprising: a second body having a top surface, a second distal end, a second proximal end and a second bottom portion, wherein the second bottom portion comprises a second mounting mechanism configured to clamp the stabilizer to the at least one rail, wherein the second mounting mechanism comprises a second fixed jaw and a second movable jaw; and wherein a second mounting mechanism actuator is pivotally mounted within the second bottom portion above the second movable jaw, the second mounting mechanism actuator being configured to move the second movable jaw from an unlocked position to a locked position and vice versa, wherein the second mounting mechanism actuator is configured to move the second movable jaw toward the locked position when the second mounting mechanism actuator is pulled in a proximal direction, wherein a second cam is mounted above a bottom surface of the second movable jaw and below the second mounting mechanism actuator, the second cam connected to the second mounting mechanism actuator to be actuated to lock or unlock the movable jaw, wherein the second top surface is smooth and substantially flat with no obstructions thereon, and wherein the second top surface provides a rest for a surgeon's hand, that can be used to help stabilize the surgeon's hand; a second joint member including a second disk member pivotally mounted in a distal end portion of the second mount body and a second slotted ball fixed to the second disk member; a second arm extending distally from the second joint, wherein the second joint member forms a joint with a proximal end of the second arm; a pair of contact members configured to be exerted against a tissue surface of the organ to stabilize the tissue surface and at least one of the contact members configured to attach a blower/mister device thereto or having a blower/mister device incorporated therein; a second actuator rotatably mounted to the second mount body at the proximal end of the second mount body and a second cable extending from the second actuator through the second mount body, second disk member, second slotted ball and second arm, the second actuator and the second cable being configured to change a state of the second arm from a flexible state to a rigid state by rotation of the second actuator in a second rotational direction, and from the rigid state to the flexible state by rotation of the second actuator in a counter-rotational direction, wherein the second disk member comprises a second slot formed therein, the second slot being curved to facilitate bending and tightening of the cable thereagainst when the second disk member has been pivoted, thereby helping to eliminate or reduce variations in at least one of second cable length and second cable tension at different angular positions of the second disk member relative to the second mount body; and a second vacuum tube in fluid communication with the suction member, wherein the second actuator comprises a clip configured to receive and temporarily hold the second suction tube to maintain the second suction tube in a low profile with the stabilizer; wherein the second actuator comprises a plurality of second fins with one of the clips formed in each of the fins, and wherein the second vacuum tube comprises a second color-coded connector at a proximal end thereof, the second color-coded connector configured to be connected to a source of vacuum or another vacuum line in fluid communication with a source of vacuum; a second canister in fluid communication with the second vacuum tube via the second color-coded connector, the second canister having a second opening for connecting the second canister in fluid communication with the second vacuum source, the second canister configured to trap fluid therein, wherein the second canister has at least one substantially flat side, and wherein a surface of the second canister is matted to inhibit glare reflection therefrom; a second strap connected to the second canister and adapted to hang the second canister in an upright orientation wherein the second opening for connecting the second canister with the second vacuum source is higher than a second connection forming the fluid communication of the second canister with the second vacuum tube; and a second filter in fluid communication with the second opening of the second canister, the second filter configured to be connected to the second vacuum source and to filter particulates from effluent from the second canister.

In another aspect of the present invention, a surgical instrument is provided that includes a mount body, an arm, a joint, and a tool; the mount body configured to mount to a retractor, a bottom surface of the mount body facing the retractor when mounted, a front edge of the mount body running at an angle to the bottom surface; the arm pivotally connected on a proximal end via the joint to the front edge of the mount body; the tool connected to a distal end of the arm; the arm configured to be movable between a plurality of positions relative to the mount body and to be temporarily lockable in these positions; and the joint configured such that a proximal portion of the arm extending from and adjacent the mount body is pivotable to and temporarily lockable in a position substantially perpendicular to the mount body.

According to an example embodiment, the surgical instrument further comprises a universal connector configured to connect the mount body to any one of a plurality of retractors of different size.

According to an example embodiment, the joint includes a disk member.

According to an example embodiment, the joint includes a slotted ball.

According to an example embodiment, the instrument includes an actuator rotatably mounted to the mount body at the proximal end of the mount body and a cable extending from the actuator through the mount body, disk member, slotted ball and arm, and the actuator and the cable are configured to change a state of the arm from a flexible state to a rigid state by rotation of the actuator in a first rotational direction, and from the rigid state to the flexible state by rotation of the actuator in a counter-rotational direction.

According to an example embodiment, a tube is provided in fluid communication with the tool.

According to an example embodiment, a tube is provided in fluid communication with the tool, and the actuator includes a clip configured to receive and temporarily hold the tube to maintain the tube in a low profile with the instrument.

According to an example embodiment, the mount body includes a recess sized to receive and removably retain the tube.

According to an example embodiment, the instrument is a stabilizer and the tool comprises at least one contact member configured to be exerted against a tissue surface to stabilize the tissue surface.

According to an example embodiment, the instrument is a positioner and the tool comprises a suction member defining a vacuum space therein, wherein the suction member is configured to exert sufficient suction force on an organ to move the organ when the suction member is placed against the organ, a negative pressure is applied within the vacuum space to engage the suction member with the organ, and the suction member is moved.

According to an example embodiment, the instrument includes a cable extending through the disk member, at least a portion of the arm and at least a portion of the mount body, wherein the disk member comprises a slot formed therein, the slot being curved to facilitate bending and tightening of the cable thereagainst when the disk member has been pivoted, thereby helping to eliminate or reduce variations in at least one of cable length and cable tension at different angular positions of the disk member relative to the mount body.

According to an example embodiment, an actuator is rotatably mounted to the mount body at the proximal end of the mount body and a cable extends from the actuator through the mount body, disk member, ball and arm. The actuator and the cable are configured to change a state of the arm from a flexible state to a rigid state by rotation of the actuator in a first rotational direction, and from the rigid state to the flexible state by rotation of the actuator in a counter-rotational direction.

According to an example embodiment, a canister is provided in fluid communication with the tube, the canister having an opening for connecting the canister in fluid communication with a vacuum source, the canister configured to trap fluid therein.

According to an example embodiment, a filter is in fluid communication with the opening of the canister, and the filter is configured to be connected to the vacuum source and to filter particulates from effluent from the canister.

According to an example embodiment, a strap is connected to the canister and adapted to hang the canister in an upright orientation wherein the opening for connecting the canister with a vacuum source is higher than a connection forming the fluid communication of the canister with the vacuum tube.

In another aspect of the present invention, a surgical instrument is provided that includes a mount body, an arm, a tool, and a tube; the mount body configured to mount to a retractor or a surgical table; the arm pivotally connected on a proximal end to the mount body; the tool connected to a distal end of the arm; the arm configured to be movable between a plurality of positions relative to the mount body and to be temporarily lockable in these positions; a distal end of the tube connected at or adjacent a distal end of the arm; and the mount body configured to removably retain the tube.

According to an example embodiment, the mount body includes a recess sized to receive and removably retain the tube.

According to an example embodiment, the mount body includes a clip sized to receive and removably retain the tube.

According to an example embodiment, the mount body further includes an actuator rotatably mounted to the surgical instrument, the actuator being configured to change a state of the arm from a flexible state to a rigid state by rotation of the actuator in a first rotational direction, and from the rigid state to the flexible state by rotation of the actuator in a counter-rotational direction; and the actuator configured to removably retain the tube.

According to an example embodiment, the arm is pivotally connected to the mount body via a joint.

According to an example embodiment, the joint includes a disk member.

According to an example embodiment, the joint includes a slotted ball.

According to an example embodiment, the tube is provided in fluid communication with the tool.

According to an example embodiment, that actuator includes a clip configured to receive and temporarily hold the tube to maintain the tube in a low profile with the instrument.

According to an example embodiment, the instrument is a stabilizer and the tool comprises at least one contact member configured to be exerted against a tissue surface to stabilize the tissue surface.

According to an example embodiment, the instrument is a positioner and the tool comprises a suction member defining a vacuum space therein, wherein the suction member is configured to exert sufficient suction force on an organ to move the organ when the suction member is placed against the organ, a negative pressure is applied within the vacuum space to engage the suction member with the organ, and the suction member is moved.

According to an example embodiment, the instrument includes a cable extending through the disk member, at least a portion of the arm and at least a portion of the mount body, wherein the disk member comprises a slot formed therein, the slot being curved to facilitate bending and tightening of the cable thereagainst when the disk member has been pivoted, thereby helping to eliminate or reduce variations in at least one of cable length and cable tension at different angular positions of the disk member relative to the mount body.

According to an example embodiment, an actuator is rotatably mounted to the mount body at the proximal end of the mount body and a cable extends from the actuator through the mount body, disk member, ball and arm. The actuator and the cable are configured to change a state of the arm from a flexible state to a rigid state by rotation of the actuator in a first rotational direction, and from the rigid state to the flexible state by rotation of the actuator in a counter-rotational direction.

According to an example embodiment, a canister is provided in fluid communication with the tube, the canister having an opening for connecting the canister in fluid communication with a vacuum source, the canister configured to trap fluid therein.

According to an example embodiment, a filter is in fluid communication with the opening of the canister, and the filter is configured to be connected to the vacuum source and to filter particulates from effluent from the canister.

According to an example embodiment, a strap is connected to the canister and adapted to hang the canister in an upright orientation wherein the opening for connecting the canister with a vacuum source is higher than a connection forming the fluid communication of the canister with the tube.

These and other features of the invention will become apparent to those persons skilled in the art upon reading the details of the instruments and methods as more fully described below.

BRIEF DESCRIPTION OF THE DRAWINGS

FIG. 3 is a perspective view of a surgical stabilizer instrument according to an embodiment of the present invention.

FIG. 4 is an exploded view of the stabilizer instrument of FIG. 3.

FIG. 5 is a longitudinal sectional view illustrating a joint member that includes a swivel joint that is formed by a disk member pivotally mounted to a mounting mechanism according to an embodiment of the present invention.

FIG. 6 illustrates pivoting action provided by the swivel joint illustrated in FIG. 5.

FIG. 11 shows a configuration in which actuator (not shown) is actuated to drive the mount body against the disk to thereby lock the angular position of disk relative to body, according to an embodiment of the present invention.

FIG. 12 is a sectional view of the embodiment of FIG. 11, but which additionally shows the actuator.

FIG. 13A illustrates a side view of an arrangement wherein scalloped detents are provided in which a ball can nest, according to an embodiment of the present invention.

FIG. 13B illustrates a top sectional view taken along line A-A of FIG. 13A.

FIG. 22 shows a surgical instrument configured as an organ positioner instrument according to an embodiment of the present invention.

FIG. 23 is an exploded view of the instrument of FIG. 22.

FIG. 24 shows two surgical instruments, a first configured as a positioner instrument and a second configured as a stabilizer instrument, both mounted to rails of a sternal retractor according to an embodiment of the present invention.

FIG. 25 is a partial, longitudinal sectional view of the device of FIG. 22.

FIG. 26 is a top view of a slot in a partial, longitudinal sectional view taken in a plane at right angles to the plane along which the partial sectional view of FIG. 25 is taken.

FIG. 29C illustrates a surgical instrument configured as a stabilizer instrument with a mount body configured to removably retain a tube, according to an embodiment of the present invention.

FIGS. 30A-30B show a side view and an end view, respectively, of an actuator according to another embodiment of the present invention.

DETAILED DESCRIPTION OF THE INVENTION

Figure 1:
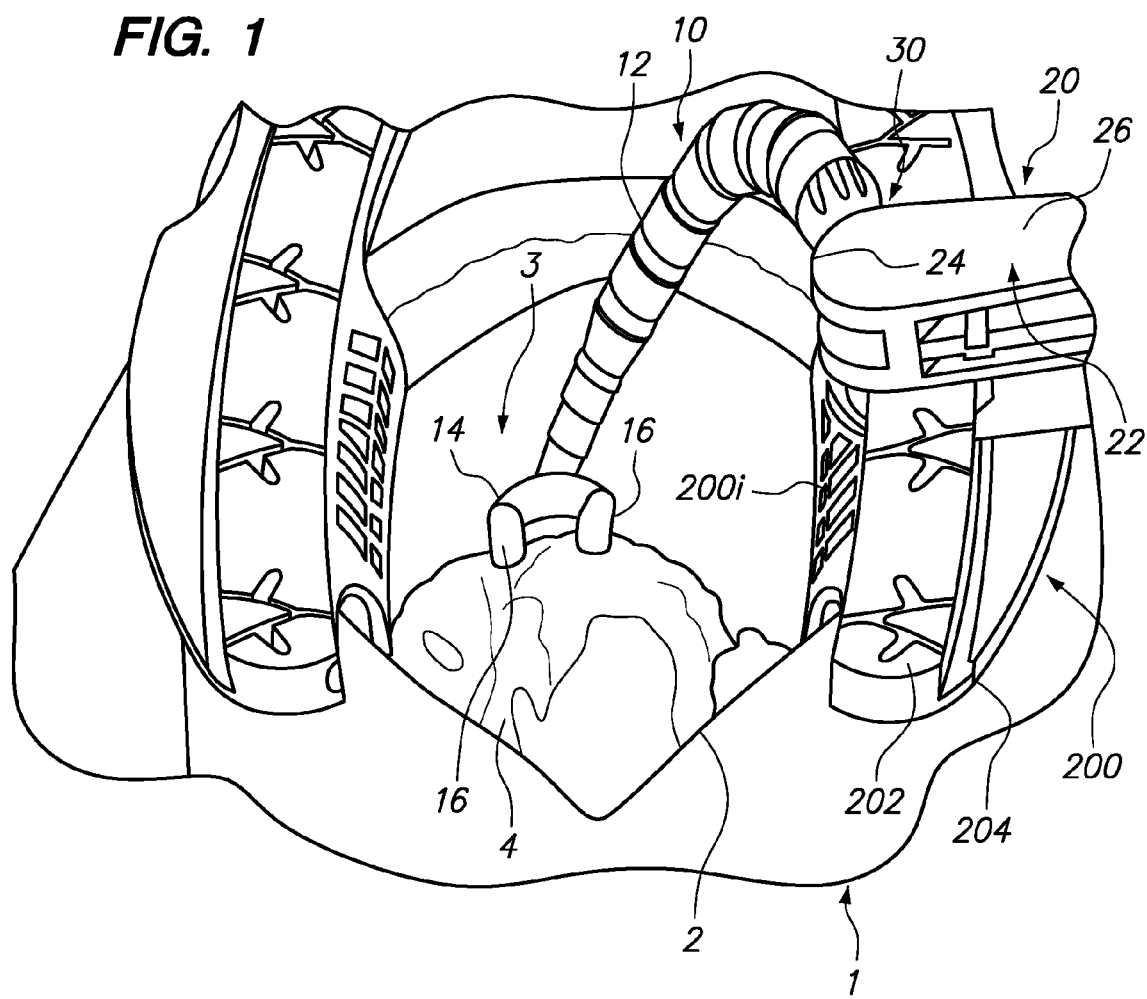
FIG. 1 illustrates a surgical instrument configured as a surgical stabilizer instrument according to an embodiment of the present invention.

Before the present instruments and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the terms "lock" or "locked" shall mean to constrain or make immovable, or movable with difficulty.

It must be noted that as used herein and in the appended claims, the singular forms "a", "an", and "the" include plural referents unless the context clearly dictates otherwise. Thus, for example, reference to "a contact member" includes a plurality of such contact members and reference to "the device" includes reference to one or more devices and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Although the instruments described herein are described for use on the heart, it is noted that these instruments are not limited to use on the heart, but can be used for surgical procedures on other organs or tissues, such as to position and/or stabilize other organs or tissues.

FIG. 1 shows a surgical instrument configured as a stabilizer instrument 10 according to an embodiment of the present invention. Stabilizer instrument 10 includes a mounting mechanism 20 configured to mount the stabilizer instrument 10 to a relatively fixed object, such as a sternal retractor, operating table, etc. In FIG. 1, stabilizer instrument 10 is mounted to a rail 202 of a sternal retractor 200. The sternal retractor is shown being used in an open-chest procedure in which an opening 2 has been spread to expose the heart 4 of the patient 1.

Stabilizer instrument 10 further includes an arm 12 pivotally connected to and extending distally from a distal end 24 of mount body 22. The top surface 26 of mount body 22 has a low profile and preferably is smooth so as not to catch sutures, surgical gloves or any other object susceptible to being caught on a non-smooth surface. Additionally, this smooth surface can be used by the surgeon to rest a hand or finger against, to assist in steadying the hand during suturing, for example. Because arm 10 extends from the distal end 24 of mount body 22 and not from the top surface 26 as in many prior art instruments, it provides a lower profile, relative to the height of the patient's 1 chest 2 and the sternal retractor 200. This makes the instrument less of an obstruction (relative to prior art stabilizer instruments where the arm is attached to the top of the attachment mechanism) to the surgeon or anyone else trying to access the surgical working space 3.

Stabilizer instrument 10 further includes a working end 14 mounted to a distal end portion of arm 12. The working end 14 of stabilizer instrument 10 includes at least one contact member 16. A pair of contact members 16 are provided in the embodiment shown in FIG. 1. Contact members 16 are configured and dimensioned to contact the surface of tissue at a surgical target area to stabilize the tissue and to facilitate the performance of a surgical procedure. For example, in FIG. 1, the contact members are shaped, configured and dimensioned to contact the surface of the heart 4 on opposite sides of a coronary artery on which an anastomosis is to be performed.

Contact members 16 may be configured to engage tissue by mechanical means (which optionally may include friction enhancing contact surfaces), by application of suction, or combinations thereof. There are many different embodiments of contact members that may be employed in a surgical stabilizer instrument according to embodiments of the present invention. Further examples of such contact members and details of the same can be found in U.S. Pat. Nos. 5,727,569; 5,875,782; 5,894,842; 5,906,607; 5,957,835; 5,976,069; 6,032,672; 6,036,641; 6,050,266; 6,120,436; 6,213,941; 6,231,506; 6,283,912; 6,290,644; 6,315,717; 6,331,158; 6,346,077; 6,375,611; 6,394,951; 6,406,424; 6,511,416; 6,626,830; 6,652,454; 6,656,113; 6,673,013; 6,685,632; 6,701,930; 6,743,169; 6,758,808; 6,849,044; 6,852,075; 6,893,391; 7,056,287; 7,220,228; 7,238,155; 7,326,177; 7,335,158; 7,485,090; 7,497,824; and 7,503,891, each of which is hereby incorporated herein, in its entirety, by reference thereto.

Figure 2:
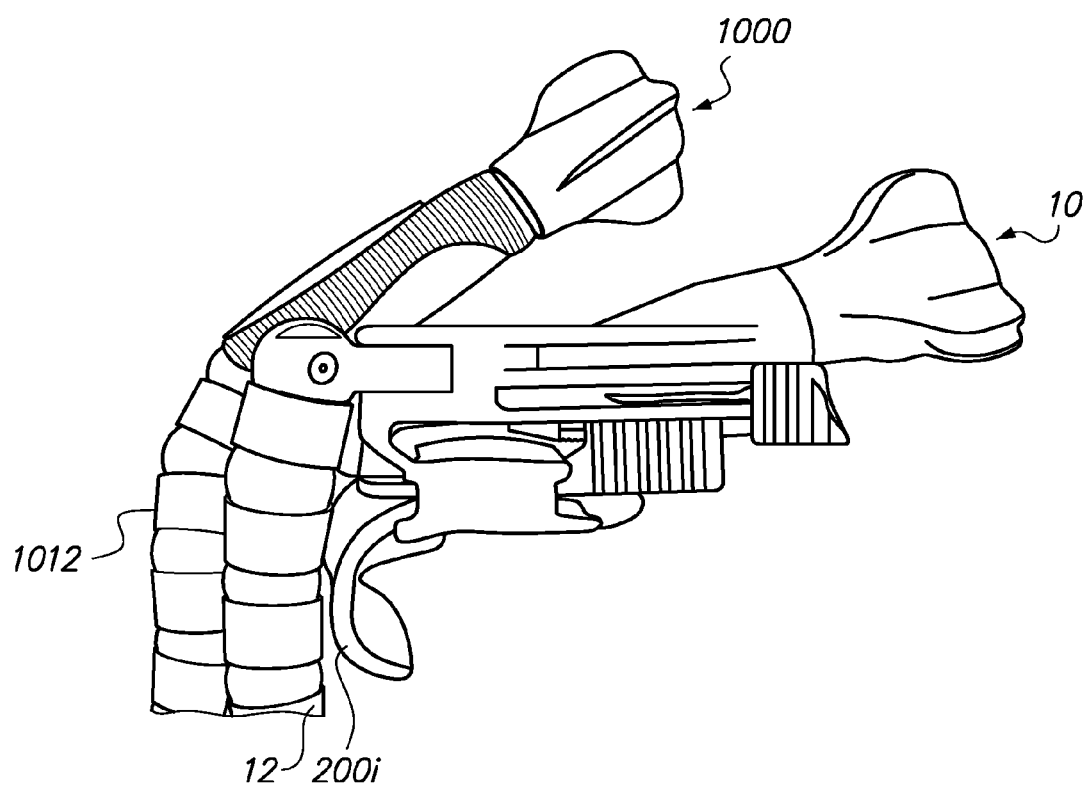
FIG. 2 illustrates the ability of a joint member, according to the present invention, to provide an arm with the ability to be positioned very close to the inner surface of a sternal retractor, relative to the ability of a prior art stabilizer arm.

Mount body 22 is configured and dimensioned so that the distal end 24 thereof is substantially laterally flush with an inner surface 200i of the sternal retractor 200, particularly with an inner surface of the arm/blade 204 of the sternal retractor. Alternatively, the distal end 24 may extend slightly beyond the inner surface 200i or end slightly proximally of the inner surface 200i. In any case, when the stabilizer instrument is fixed to rail 202 as shown in FIG. 1, the distal end 24 of the mount body 20 does not extend substantially into the surgical working space 3, and thus forms much less of an obstruction than currently available surgical stabilizers. Further, the joint member 30 that joins arm 12 provides the arm 12 with the ability to be positioned very close to the inner surface 200i, relative to the ability of a prior art stabilizer arm 1012 of prior art stabilizer 1000, as shown in FIG. 2. This also reduces the amount of obstruction created by the stabilizer 10 and particularly the stabilizer arm 12. Joint member 30 even permits arm 12 to be oriented in contact with the inner surface 200i. Still further, the joint member 20 is configured such that a portion of the arm 12 extending from and immediately adjacent the joint member 30 is pivotable to and temporarily lockable in a position substantially perpendicular to the mount body 22, as illustrated in FIG. 2. Specifically, as shown in FIG. 2, the most proximal link 44 of arm 12 can be positioned substantially perpendicular (i.e., at an angle of about 80 degrees to about 90 degrees) to the mount body 22.

Joint member 30 is pivotally mounted to mount body 22 at the distal end portion thereof, so that arm 12, which is joined to the distal end of joint member 30, extends from the distal end 24 of mount body 22. FIG. 3 is a perspective view of a surgical stabilizer instrument 10 according to an embodiment of the present invention. Working end 14 is mounted to the distal end of arm 12 via a joint 56 (ball and socket joint in the embodiment shown in FIG. 3) as described in more detail in previous patents incorporated by reference above.

Arm 12 comprises a plurality of articulating links 40 that allow the arm 12 to be flexible in a first configuration, but which can be compressed to render the arm 12 substantially rigid in a second configuration. In the embodiment shown in FIG. 3, links 40 include alternating ball joints 42 and biconcave disks 44. Balls 42 are made of a plastic have a hardness that is less than the hardness of the material (typically, plastic) that the disks 44 are made of. This allows the disks 44 to become embedded into the balls 42 during compression of the components applied by applying tension to the tensioning member running therethrough, thus increasing the rigidity of the arm by the grip imposed by the embedding disks. Further details and examples of suitable arms are described in U.S. Pat. No. 6,506,149, which is hereby incorporated herein, in its entirety, by reference thereto. Alternatively, links 40 may include (but alternatives are not limited to these examples) a series of ball joints, a series of joints having one convex side and one concave side, or any of the other embodiments described in U.S. Pat. No. 6,506,149, or any of the embodiments described in U.S. Pat. No. 6,758,808, for example.

Each link 40 includes a central channel 40c therethrough which may be tapered at both ends to allow a cable 46 (see the exploded view of FIG. 4) to pass through it smoothly and easily (and to improve rigidity in the arm's rigid state). Cable 46 extends through links 40, joint member 30, mount body 22 and connects proximally to an actuation mechanism 50 and connects distally to a mechanism configured to lock or unlock joint 56. The distal-most articulating member 43 at the distal end of arm 12 includes a cavity 43c which opens at the distal end of the articulating member 43 and is adapted to at least partially receive coupling members 58, 47 and 60. A socket member 56s caps the distal end of the stabilizer arm 12 and is mated to the distal most articulating member 43 via coupling members 58, 47 and 60, in concert with the tensioning cable 46 which runs through the stabilizer.

Socket member 56s includes an opening 56p, which is dimensioned to freely receive the ball portion 56b to which working end 14 is fixed. Socket member 56s further includes a slot 56l dimensioned to receive stem 56t, allowing it to slide freely in the slot 56l while at the same time preventing ball portion 56b from passing therethrough. A proximal opening is provided in the socket member 56s and dimensioned to receive at least a portion of coupling members 58, 47 and 60.

Coupling member 60 may be a socket cap which is received within the proximal opening. Socket cap 60 includes a base or cap portion (shown and described in greater detail in U.S. Pat. No. 6,758,808) to abut ball portion 56b and maintain it in its position in the socket member 56s. In the example shown, the cap portion has a substantially planar bottom surface with a circular opening dimensioned to ride against the sphericity of the ball portion 56b. Of course, other configurations of the bottom surface are contemplated which would accomplish the same function, e.g., the ability to apply force against the ball portion 56b and maintain the ball portion within the socket member 56s, while also allowing the ball portion to rotate. Still further, upon increased application of force, the cap portion has the ability to lock the ball portion 56s and prevent it from rotating.

The outer surface of the socket cap 60 is substantially cylindrical and adapted to slidably and rotatably fit within the cavity of the coupling member 56s introduced by the proximal opening thereof. This allows rotation of the working end 14 about the longitudinal axis of the maneuverable arm 12 when the stabilizer 10 is in a non-rigid state. The proximal portion of the socket cap 60 includes driving surfaces adapted to abut against the distal most articulating member 43 and transmit force against the ball portion 56b when the cable is tensioned. Upon complete release of tension in the stabilizer 10 cable 46, the socket member 56s may be pulled in a direction away from the distal most articulating member 43 by a sufficient distance to allow ball portion 56b to be extracted through opening 56p, for example to change the setup by replacing the existing working end 14 with a different one. Thus, a change may be made between working ends 14 to choose a different design or configuration, or even to change to one which operates on a different principle. For example a change from a mechanical contact member, which operates by applying physical pressure against the beating heart tissue, may be replaced with a negative pressure contact member, which engages the heart by vacuum. In this regard, any of the contact members described herein could be exchanged for operation in the stabilizer 10 described. Additionally, other known contact members could be used or adapted to be used by those of ordinary skill in the art.

The socket cap 60 further includes recessed or open portions dimensioned to receive the arms of coupling member 58. The recessed portions are continuous over the length of the socket cap 60 and are also defined along the perimeter of the cap portion. In this way, the arms of coupling member 58 interfit with the socket cap and are continuous with the outer perimeter thereof to form a cylindrical surface for rotating against the socket member 56s. The interior surface of socket member 56s is undercut near the proximal end to form an annular groove that extends around the interior circumference of the proximal end portion and underlies a lip formed thereby. Upon assembly, tines which extend outwardly from the arms of coupling member 58 at the distal ends of the arms, engage the groove and are prevented from being withdrawn from the socket member 56s by the lip. Because the lip and groove extend around the entire inner circumference of the socket member 56s, coupling member 58 is free to rotate with socket cap 60 in an unlocked configuration of the stabilizer 10. The outside ends of the tines are preferably chamfered or beveled to ease the insertion of the coupling member 58 into the socket member 56s.

A cable fitting is provided as a part of the coupling assembly, and includes an enlarged ball-shaped or other shape stop portion/coupling member 47 which has an abutment surface adapted to abut against coupling member 58 to apply a force thereto when the cable is drawn up thereagainst.

The proximal end of cable 46 is connected to actuation mechanism that is configured to increase or decrease tension in cable 46 by drawing the proximal end portion of cable 46 proximally or moving it distally relative to mount body 22, respectively. Increase and decrease of tension is actuated by actuator 52, such as the knob shown in FIGS. 3-4. Further details about the operation of mechanism 50 and alternative embodiments of such mechanism can be found, for example, in U.S. Pat. No. 6,758,808 and other patents incorporated by reference above. The present invention is not intended to be limited to the mechanism 50 shown in FIG. 4, as other mechanisms that provide the same function can be substituted.

In the embodiment shown in FIGS. 3-4, working end 14 includes openings 16s through the contact surfaces of contact members 16 that are configured to apply suction (negative pressure) to the surface of the tissue to be stabilized, to cause the contact surfaces to engage the tissue. Openings 16s are in fluid communication with vacuum tube 62, which is configured, at its proximal end, to be connected in fluid communication with a source of negative pressure. A connector 64 provided at the proximal end of vacuum tube 62 may be color coded (e.g., color coded blue, or some other distinct color), so that users can readily visually distinguish this vacuum tube from other vacuum tubes that may be being used during the procedure (such as a vacuum tube for a positioner, discussed in more detail below). This can be important when the different vacuum tubes require different vacuum characteristics, such as the magnitude of negative pressure, for example, as it helps prevent mistaken attachment of a vacuum tube to the wrong vacuum source. Color coding the luer or tubing is an inexpensive way of distinguishing the tube.

The joint member 30 includes a swivel joint 32 that is formed by a disk member 34 pivotally mounted to mounting mechanism 20 as illustrated in FIG. 3 and in the partial, longitudinal sectional view of FIG. 5. The pivoting action provided by swivel joint 32 allows the stabilizer arm 12 to be pivoted out of the way so that the arm does not excessively protrude into the surgical working space 3. As illustrated in FIG. 6, the arm can be pivoted towards the right or left of the distal end 24 of mount body 22, by pivoting disk member 34 relative to mount body 22, so that the arm 12 approximates or even contacts the inner surface of the retractor 200i and the arm can thus be adjusted to follow along the contour of the perimeter of the surgical working space 3. The pivoting can be achieved along a single plane coexistent with the disk member 34. Additionally, the pivoting can occur without movement of the actuating mechanism 50 with respect to the mount body 22.

Figure 7:
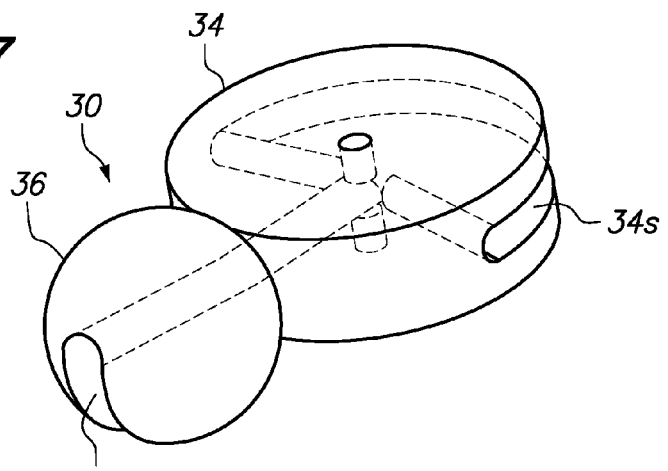
FIG. 7 illustrates a disk member that is slotted through a proximal portion thereof, according to an embodiment of the present invention.

Disk member 34 is slotted with slot 34s through a proximal portion thereof, forming top and bottom proximal disk surfaces 34p wherein the slot 34s typically sweeps through at least about 120 degrees of the periphery of the disk member 34, more typically at least about 150 degrees as shown in FIG. 7, and extends into the center of the disk member 34. Slot 34s allows the cable 46 to be tensioned while maintaining (i.e., without changing or affecting) the rotational position of disk member 34 relative to the mount body 22. The pivot point at the center of the disk member 34 allows the disk member 34 to maintain its angular position during tensioning of the cable 46.

Figure 8:
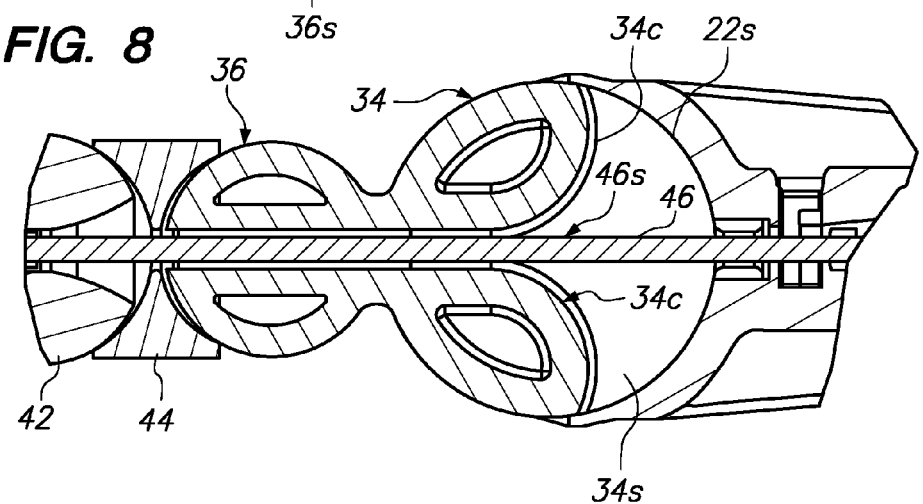
FIG. 8 is a top view of a slot in a partial, longitudinal sectional view taken in a plane at right angles to the plane along which the partial sectional view of FIG. 5 is taken.

As shown in the embodiment of FIG. 8, which provides a top view of slot 34s in a partial, longitudinal sectional view taken in a plane at right angles to the plane along which the partial sectional view of FIG. 5 is taken, the disk member 34 rotates in a circular slot without a pin. Pivoting is caused by sliding along mating circular surfaces of the disk member 34 and the circular slot. The disk member 34 is held in place by friction and an interference fit with the circular slot 22s formed within the distal end 24 of mount body 22. The radius of the disk member 34 is slightly larger than the radius of curvature of slot 22s. When the cable 46 is tensioned, the disk member 34 is pulled into a seat formed by the circular slot 22s. Chamfers 34r formed by removing corners at the top and bottom circular edges of the disk member 34 (see FIG. 5) may be provided to facilitate seating the disk member 34. When the cable 46 is not tensioned, the disk member 34 is retained in the distal end of the mount body by arm 12, distal end of mount body 24 and cable 46. The curvature 34c at the distal ends of the slot facilitates bending and tightening of the cable thereagainst when disk member 34 has been pivoted, and helps to eliminate or reduce variations in cable length/tension at different angular positions of the disk member 34. Preferably the disk member is metal such as stainless steel, and the ball 36 is plastic and press fitted onto disk member 34. Ball member 36, like the other balls in the arm, is softer than the disc member 44 that it interfaces with, so that disc member 44 bites into ball 36 to help provide further rigidify to the arm 12 when the arm 12 is in a locked configuration.

Additionally, joint member 30 includes a ball 36 extending from a distal end of disk member 34 as shown in FIG. 7. Ball 36 is dimensioned to cooperate with a concave proximal surface of link 44, thereby allowing ball and socket type, three-dimensional articulation of the link (and therefore the arm 12 and working end 14) relative to ball 36. Ball 36 may also be slotted 36s to further facilitate or optionally control the downward angulation of arm 12 relative to mount body 22, thereby facilitating positioning the arm downwardly and following the contour of the retractor and perimeter of the surgical opening as illustrated in FIG. 6. Slot 36s may be provided with a curvature 36c on the proximal end thereof, as illustrated in FIG. 5. Curvature 36c at the proximal end of the slot 36s facilitates bending and tightening of the cable thereagainst when arm 12 has been pivoted downwardly relative to ball 36/disk member 34, and helps to eliminate or reduce variations in cable length/tension at different angular positions of the arm 12. Further, a lubricious sleeve 46s (such as one made of polytetrafluoroethylene) or lubricious coating nay be provided over cable 46 to help facilitate sliding and reduce friction, as illustrated in FIG. 8.

Figure 9:
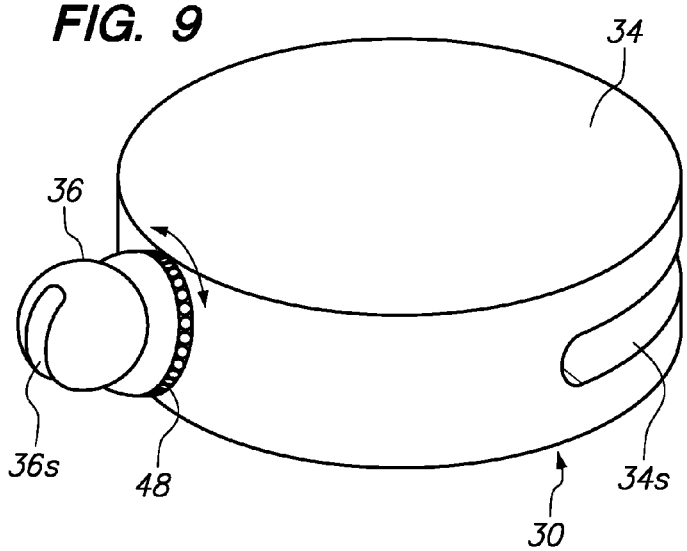
FIG. 9 illustrates an alternative embodiment of a joint member according to the present invention, in which a ball is rotationally mounted to a disk member.

FIG. 9 illustrates an alternative embodiment of joint member 30 in which ball 36 is rotationally mounted to disk member 34. Optionally, detents or ratchet teeth 48 may be provided to allow a ratchet-like adjustment of the rotational position of ball 36, relative to disk member 34.

Figure 10:
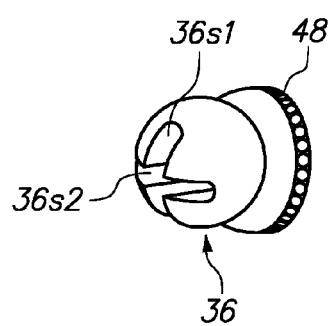
FIG. 10 shows an alternative embodiment to the ball shown in FIG. 9, according to the present invention.

FIG. 10 illustrates another alternative embodiment of ball 36 wherein ball 36 is provided with two intersecting slots 36s1, 36s2 formed perpendicularly to one another. Further alternatively, three or more intersecting slots 36s may be provided. Like the previous embodiments, ball 36 may be fixed to disk member 34 or may be rotationally mounted to disk member 34. Optionally, detents or ratchet teeth 48 may be provided to allow a ratchet-like adjustment of the rotational position of ball 36, relative to disk member 34.

FIG. 11 shows an embodiment in which actuator (not shown) is actuated to drive disk 34 against mount body 22 to thereby lock the angular position of disk 34 relative to body 22. Additionally, ball 36 is angled downwardly relative to the plane of orientation of disk 34, i.e., see angle 39. It is noted that any of the other balls 36 described above as well as below can alternatively be positioned at a downwardly angled orientation relative to the plane of disk 34.

FIG. 12 is a sectional view of the embodiment of FIG. 11, but which additionally shows an actuator 52. As the actuator 52 is tightened (by turning against the screw mechanism within) against the body 22 it drives the disk 34 against body 22 and at the same time, pulls the balls 36, 42 and links/disc members 44 together, tightening the arm 12 and joint between disk 34 and housing 22.

FIGS. 13A-13B illustrate a side view and a top sectional view taken along line A-A of FIG. 13A, wherein mount body 22 is provided at its distal end portion with a plurality of horizontally and radially distributed scallops or detents 54 each configured and dimensioned to receive a proximal most ball 42 of arm 12 or 1012. Upon applying tension through cable 46, this draws the proximal-most ball 42 into locking engagement with the receptacle/scallop/detent 54 in which it is positioned. Further application of tension locks the arm 12, 1012 as already described. Upon removing tension from cable 46 and sufficiently lengthening/loosening the cable 46, the proximal most ball 42 can be manually dislodged from it current position in one of the scallops 54 and moved to a desired location received by another of the scallops 54, as indicated in phantom lines in FIG. 13B. Thus, proximal most ball 42 can be positioned (and then locked) in any of the scallops, thereby providing the ability to angle the arm 12, 1012 in the horizontal plane relative to the longitudinal axis of the mount body 22, as illustrated by angle 57 in FIG. 13B.

Figure 14:
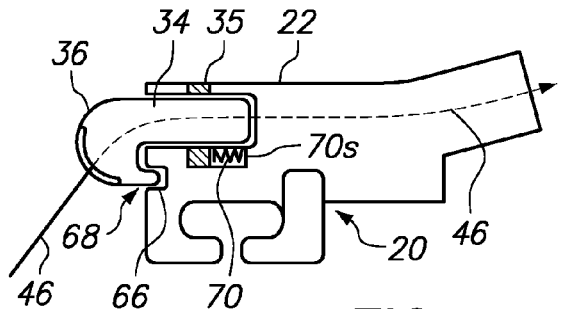
FIG. 14 illustrates a joint member and mounting mechanism in which a notch or slot is provided in mount body and a ball (or alternatively disk member) is provided with a feature (lip, tang or finger) that slides in a notch or groove as the disk member pivots relative to the mount body, according to an embodiment of the present invention.

FIG. 14 illustrates an embodiment of joint member 30 and mounting mechanism 20 in which a notch or slot 66 is provided in mount body and ball 36 (or alternatively disk member 24) is provided with a feature (lip, tang or finger) 68 that slides in notch or groove 66 as disk member 34 pivots relative to mount body 22. Upon locking down the joint member 30, arm 12 and working member 14 by drawing on cable 46 using actuator 52, feature 68 abuts against the upper surface of slot 66, which prevents the disk member 34 from lifting. Pin 35 is shown in FIG. 14 and is the feature about which disk member pivots. A spring 70 is provided in slot 70s. Spring 70 has sufficient spring force to separate the proximal end of disk member 34 from contact with the mount body 22 when tension is released in cable 46.

Figure 15:
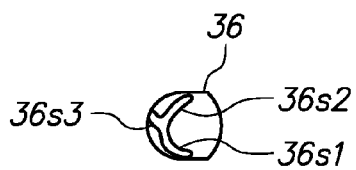
FIG. 15 illustrates a ball having a tri-slot configuration according to an embodiment of the present invention.

FIG. 15 illustrates an embodiment of ball 36 having a tri-slot configuration in which slots 36a1, 36s2 and 36s3 join to form a Y-shape.

Figure 16A:
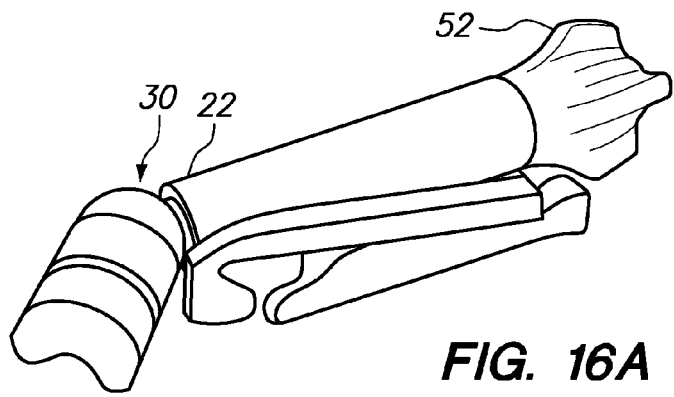
FIGS. 16A-16C illustrate a joint member in which a ball is provided with a slot and is rotationally mounted to the distal end of a mount body, according to an embodiment of the present invention.
Figure 16B:
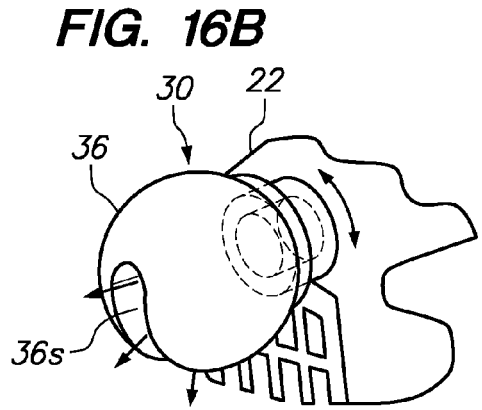

FIGS. 16A-16B illustrate an embodiment of a joint member 30 in which a ball 36 is provided with a slot 36s and is rotationally mounted to the distal end of mount body 22. In this way, joint member 30 provides similar functionality to the joint members 30 previously described that include disk member 34 and ball 36. The functionality is similar in that ball 36 can be rotated (see curved arrows in FIG. 16B), which then allows horizontal rotation or pivoting of the arm 12 when slot 36s is horizontally oriented as in FIG. 16C.

Figure 17:
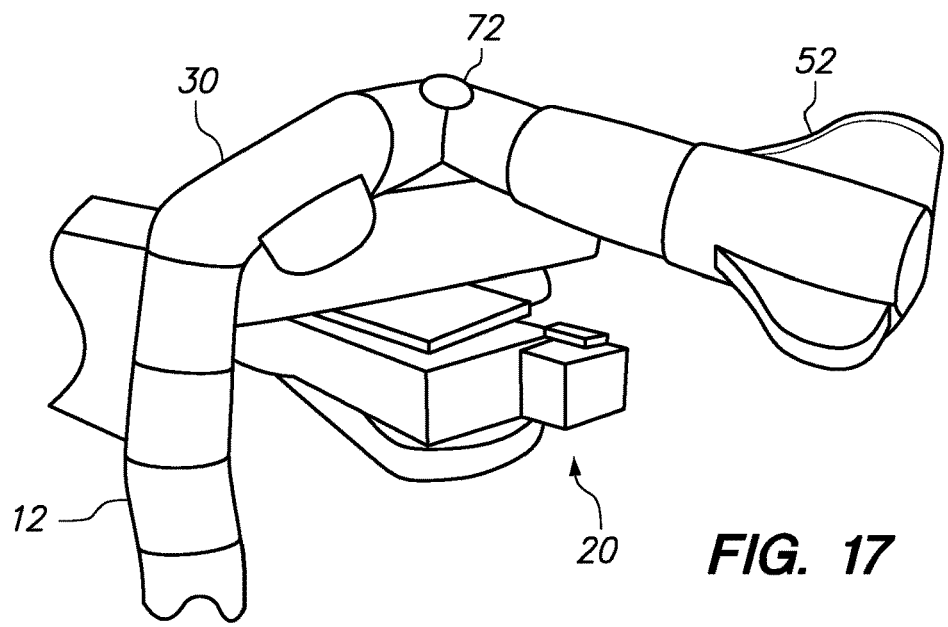
FIG. 17 shows a device in which both the arm and the actuator are angularly movable relative to the mounting mechanism according to an embodiment of the present invention.

FIG. 17 shows an embodiment in which both the arm 12 and the actuator 52 are angularly movable relative to the mounting mechanisms 20. In this regard, a joint 72 is provided to allow at least downward angulation of the actuator knob 52 relative to the mounting mechanism 20. Any of the joint members 30 described herein may be provided to allow angulation of the arm 12 relative to the mounting mechanism. By allowing angular movement of the actuator, this allows the user to move the actuator 52 to cause less of an obstruction to the surgeon or other personnel trying to access the surgical space 3. It is also less likely to catch sutures or other equipment when moved downwardly as shown in FIG. 17.

Figure 18:
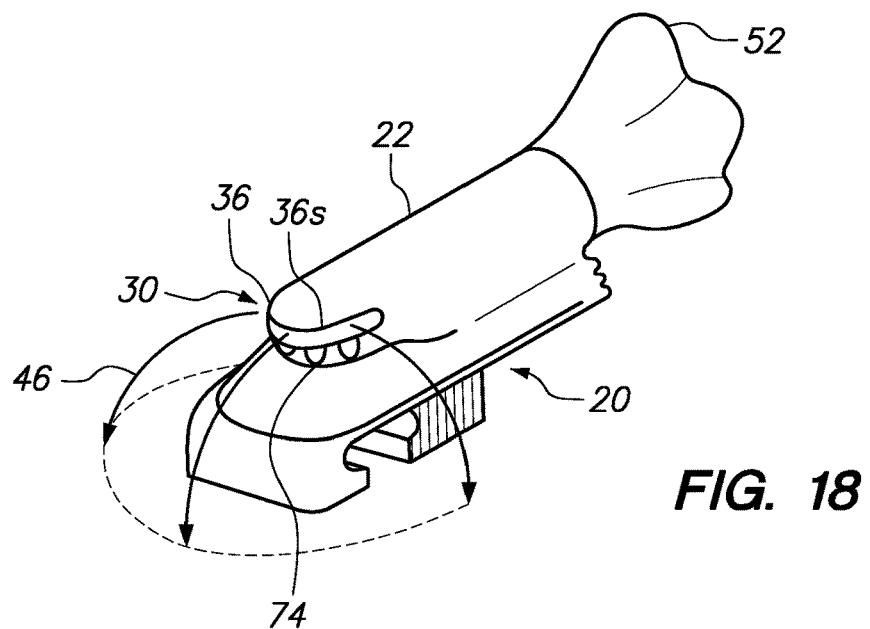
FIG. 18 illustrates an arrangement in which a slotted ball has been integrated into a mount body according to an embodiment of the present invention.

FIG. 18 illustrates an embodiment in which slotted ball 36 has been integrated into mount body 22. This reduces part count required for manufacturing, but may not be as efficient at maintaining the relative pivotal position of the arm 12 relative to the mount body 22 when the cable 46 is tightened. Optionally scallops 74 may be provided in the slotted portion 36s of ball 36 to reduce the tendency of the cable 46 to straighten the arm 12 relative to the body 22 as tension is applied.

Figure 16C:
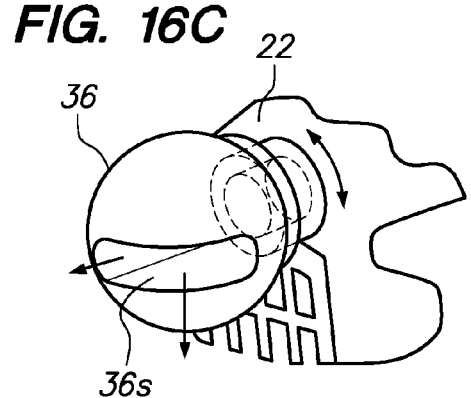
Figure 19:
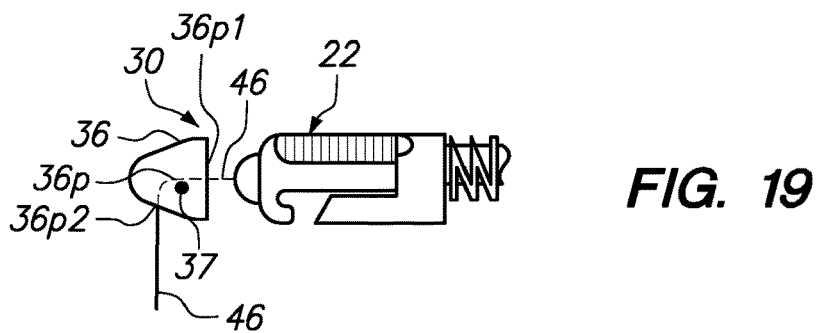
FIG. 19 illustrates a joint member similar to the embodiment of FIGS. 16A-16C, but where the ball is provided with an opening such as a through bore that defines a pathway through the ball according to an embodiment of the present invention.

FIG. 19 illustrates an embodiment of a joint member 30 similar to the embodiment of FIGS. 16A-16C, but where ball 36 is provided with an opening 36p such as a through bore that defines a pathway through ball 36 that guides cable 46 from an orientation substantially aligned with the longitudinal axis of body 22 at end 36p1, to an orientation forming an angle with respect to the longitudinal axis of the body 22 at end 36p2. In the example shown, the angle is about ninety degrees. However this angle may vary and may be selected from a range of about seventy-five degrees to about one hundred thirty five degrees, more typically from a range of about eighty degrees to about one hundred and ten degrees. A cross pin 37, such as a stainless steel pin may be provided to help support the guide path of 36p and to help reduce wear. Pin 37 provides the location over which the cable bends. The pin 37 is provided as a metal component to withstand the high drag (frictional) forces when the cable 46 is pulled at high tensions over the bend 36p. Pin 37 is cross-pinned through component 36, such as by press fitting and/or using adhesives or other fixative. Ball 36 is further provided with slot 36s and is rotationally mounted to the distal end of mount body 22. In this way, joint member 30 provides similar functionality to the joint members 30 previously described that include disk member 34 and ball 36. The functionality is similar in that ball 36 can be rotated, which then allows change in the angular position of arm 12 relative to the horizontal plane. Also, a rigid insert molded curved tube can be provided around the cable to prevent or reduce wear of the components as the tube provides less frictional resistance than the cable as it slides against the other components.

Figure 20A:
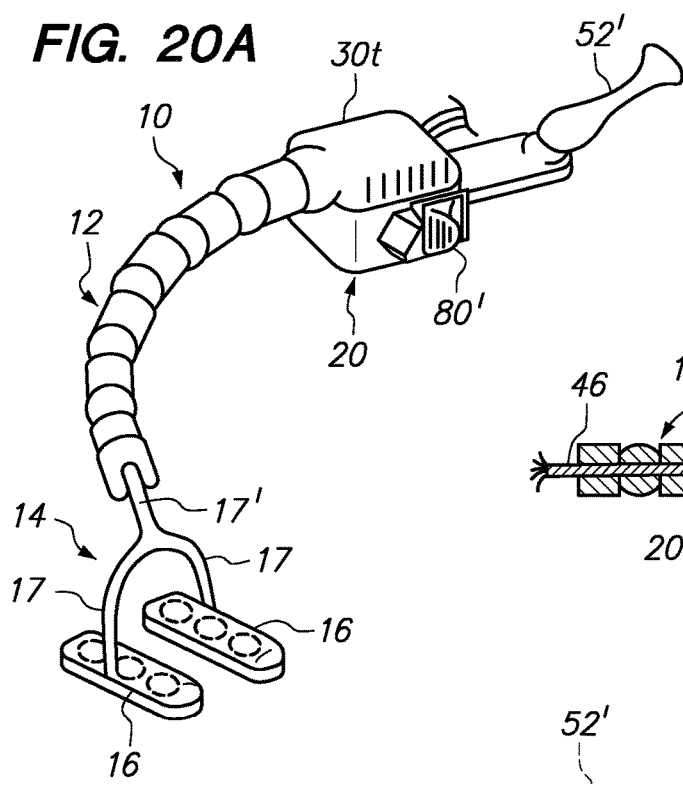
FIG. 20A illustrates a surgical instrument configured as a stabilizer instrument in which pivoting of the arm and working end relative to a fixed portion of the mounting mechanism is provided by a turret rotationally mounted on top of the mounting mechanism according to an embodiment of the present invention.

FIG. 20A illustrates an embodiment of a stabilizer instrument in which pivoting of the arm 12 and working end relative to a fixed portion of mounting mechanism 20 is provided by a turret 30t rotationally mounted on top of the mounting mechanism 20. Actuator 52' in this embodiment comprise a lever that is configured with a cam mechanism for quick tensioning (and also quick release of tension) of cable 46. The contact members 16 of working portion 14 are supported intermediate of their lengths by shafts 17 used to support the contact members 16 and connect them to arm 12 via shaft 17' and a ball joint mechanism like described previously. The intermediate connection of the shafts 17 to the contact members 16 places stabilization points closer to the target surgical site to be stabilized.

Figure 20B:
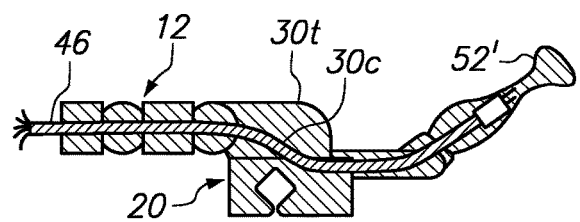
FIG. 20B is a partial longitudinal sectional view of the device of FIG. 20A.
Figure 20C:
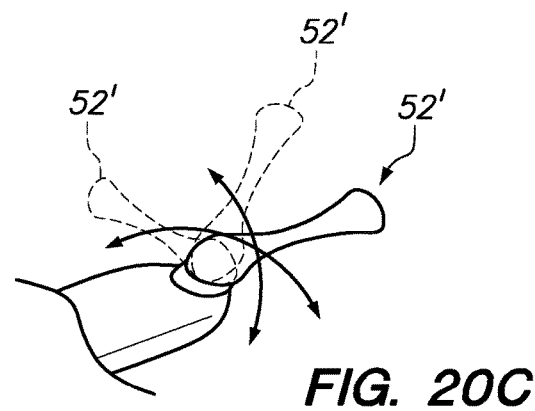
FIG. 20C illustrates that the actuator lever can be actuated at many different angles to tighten the cable.

FIG. 20B is a partial longitudinal sectional view of the device 10 of FIG. 20A showing the path of cable 46 through the mounting mechanism 20 and turret 30t. Because the cable extends up through the center 30c of the turret 30t, this allows the turret to maintain its rotational position relative to mount mechanism 20 during tightening. FIG. 20C illustrates that actuator lever 52' can be actuated at many different angles to tighten the cable 46.

Figure 21:
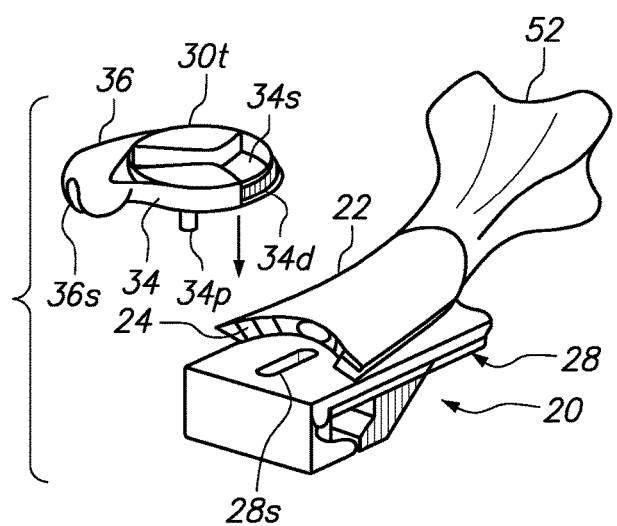
FIG. 21 illustrates a joint member that uses a turret, but where the turret is formed with a disk member and ball according to an embodiment of the present invention.

FIG. 21 illustrates a joint member that uses a turret 30t, but where the turret 30t is formed with a disk member 34 and ball 36. Disk member 34 is slotted 34s and ball 36 is slotted 36s. Turret 30t interfaces the distal end of mount body 22, and is provided with detents 34d for discrete incremental rotations of the turret 30t relative to mount body 22 and which help to maintain the current angular position of turret 30t relative to mount body 22. A pivot element 34p such as a peg or the like is inserted into slot 28s of fixation mount 28 which allows turret 30t to rotate relative to fixation mount 28 and mount body 22, and also allows cable 46 to draw turret 30t into contact with the distal surface 24 of mount body 22 and compress it thereagainst to prevent rotation of turret 30t relative to mount body 22.

FIG. 22 shows a surgical instrument configured as an organ positioner instrument 100 according to an embodiment of the present invention. Positioner instrument 100 includes a mounting mechanism 120 configured to mount the positioner instrument 100 to a relatively fixed object, such as a sternal retractor, operating table, etc. In FIG. 24, positioner instrument 100 is mounted to a rail 202 of a sternal retractor 200.

Positioner instrument 100 further includes an arm 112 pivotally connected to and extending distally from a distal end 124 of mount body 122. The top surface 126 of mount body 122 is smooth so as not to catch sutures, surgical gloves or any other object susceptible to being caught on a non-smooth surface. Additionally, this smooth surface can be used by the surgeon to rest a hand or finger against, to assist in steadying the hand during suturing or other procedural step, for example. Because arm 112 extends from the distal end 124 of mount body 122 and not from the top surface 126, it provides a lower profile, relative to the height of the patient's 1 chest opening 2 and the sternal retractor 200 than a design where the arm extends from a top of the mount body. This makes the instrument less of an obstruction (relative to prior art stabilizer instruments where the arm is attached to the top of the attachment mechanism) to the surgeon or anyone else trying to access the surgical working space 3.

Positioner instrument 100 further includes a working end 114 mounted to a distal end portion of arm 112. The working end 114 of positioner instrument 100 includes at least one contact member 116. A single contact member 116 is provided in the embodiment shown in FIG. 22, although multiple contact members 116 may be alternatively provided. A compliant joint 118 is provided for mounting contact member 116 to a rigid structure while still allowing a limited range of movements of the contact member 116. Contact member 116 is a suction member that is configured to attach to an organ and engage the organ by application of negative pressure through the suction member, with sufficient strength to move the engaged organ and maintain it in a displaced orientation. In one embodiment, this includes maintaining the apex of the heart in an elevated, suspended, orientation. Suction member 116 of FIGS. 22-23 includes a cup 151, a hollow shaft 153 fixedly attached to cup 151, and fitting 157 (for attaching a suction line 162 to shaft 153). Shaft 153 is oriented with its axis parallel to the central longitudinal axis of cup 151. Conforming seal 252 is mounted to the distal surface of cup 151. Seal 252 forms a seal with the heart (or other organ) when vacuum is applied through cup 151 and seal 252 is placed in contact with the organ. Optionally a filter 155, such as a foam filter, screen or the like, can be fitted within the cup 151 (by friction fit, co-molding and/or adhesive or other mechanical or chemical means, for example) to prevent the organ tissue from being sucked substantially into the internal area of cup 151. The concave inner surface of cup 151 may further optionally be lined with soft and absorbent material (preferably nonwoven rayon or viscose fabric, but alternatively another material such as gauze or a material of a type currently used in neuro-sponges). The absorbent material is preferably capable of absorbing enough blood and/or other bodily fluid to significantly improve traction between the cup and organ, and preferably also functions (together with filter 155, if present) to diffuse the suction exerted by member 151 on the organ.

Conforming seal 252 is preferably made of biocompatible foam having some open cells (to control a slow flow of air through seal 252), and some has closed cells (including those which define a "skin" on the distal surface of seal 252, which is the surface designed to contact the organ). The size and ratio of the open cells to the closed cells governs the rate at which air moves through the seal 252, in order to hold and continue to hold suction (with the skin of the seal 252 engaged against an organ or tissue) with a given amount of vacuum applied in 151. As noted, the skin is especially smooth so that when contacting the surface of the organ/tissue, it forms a seal therewith that is airtight and does not leak to reduce the amount of vacuum applied.

Compliant joint 118 is attached to the distal end of arm 112. This connection may be formed in the same manner as described above with regard to components 43, 47, 58, 60 and 56s above in the stabilizer embodiment of FIGS. 3-4. Alternative connections may be substituted as described in the patents that have been incorporated above. Other alternative connections, as well as alternative suction members that may be substituted can be found in U.S. Pat. Nos. 6,019,722; 6,338,712; 6,361,493; 6,390,976; 6,506,149; 6,610,008; 6,730,020; 6,969,349; 6,705,988; 6,726,622; 6,743,170; 6,899,670; 7,179,224; 7,195,591; 7,226,409; 7,377,895; 7,404,792; 7,476,196; 7,476,199; and 7,479,104, each of which is hereby incorporated herein, in its entirety, by reference thereto.

Arm 112 may be made in the same manner as arm 12 discussed above, although the members 140 and 142 may have smaller cross sectional dimensions than corresponding members 40 and 42. Alternatively, any arm that has a flexible configuration, and which can be actuated to a rigid configuration may be used, including any arms described in any of the patents incorporated by reference herein. Mounting mechanism 120 is provided to fix the positioner 100 to a stationary object, such as a sternal retractor or other fixed object.

Fork 165 is fixed to ball 56b via a post or is integrally made with the ball 56b and post. Ball 56b is free to rotate relative to socket 56s when the cable 46 is relieved of tension and arm 112 is in a flexible state. This freedom to rotate is three-dimensional freedom provided by a ball and socket arrangement. Roller 164 is rotationally mounted between the tines of form 165 and is free to rotate relative thereto. Roller 164 defines a central channel 164c, and shaft 153 of contact member 114 extends through channel 164c as shown in FIG. 22. Preferably, spring 156 is positioned around shaft 153 between fitting 157 and roller 164. Spring 156 is compressed by the force exerted on it by fitting 157 and roller 164.

During beating heart surgery, the positioner 100 of FIG. 22 functions as follows. Working portion 114 is fixedly attached by suction exerted through suction line 162, fitting 157, shaft 153 and cup 151 to the surface of the beating heart, thereby engaging the working portion 114 so that the cup 151 moves as a unit with the beating heart. The weight of the heart causes shaft 153 (and the entire cup 151) and roller 164 to rotate as a unit relative to fork 165. As shaft 153 and roller 164 rotate as described relative to fork 165, fork 165 typically also rotates relative to socket 56s. In some implementations, the device is implemented so that rotation of fork 165 relative to socket 56s occurs only during gross manipulation of the suction member 151 (with the heart coupled by suction to the suction member). In addition, as the shaft 153 and cup 151 oscillate, substantially vertically as a unit with the surface of the beating heart, shaft 153 slides (through central channel 164c of roller 164) relative to roller 164 (as the vertical position of roller 164 is fixed by fork 165.

Spring 156 dampens the oscillating motion of shaft 153 relative to roller 164, in the following manner. As shaft 153 slides vertically downward relative to roller 164, spring 156 is compressed (converting some of the kinetic energy of shaft 153 into potential energy). Then, as shaft 153 slides vertically upward relative to roller 164, spring 156 relaxes (elongates) back to its equilibrium position (assisting in pulling the heart surface upward as some of the potential energy stored in the spring is converted to kinetic energy of shaft 153). Optionally, fork 165 may include a pivoting latch (not shown, see U.S. Pat. No. 6,506,149, FIG. 30 and description thereof) which can be manually rotated between two positions: a first position in which it does not prevent shaft 153 from translating relative to roller 164; and a second (locking) position in which it prevents translation of shaft 153 relative to roller 164.

Mount body 122 is configured and dimensioned so that the distal end 124 thereof is substantially flush with an inner surface 200i of the sternal retractor 200, particularly with an inner surface of the arm/blade 204 of the sternal retractor. Alternatively, the distal end 124 may extend slightly beyond/inward of the inner surface 200i or end slightly before/outward of the inner surface 200i. In any case, when the positioner instrument 100 is fixed to rail 202 as shown in FIG. 24, the distal end 124 of the mount body 20 does not extend substantially into the surgical working space 3, and thus forms much less of an obstruction than currently available surgical stabilizers. Further, the joint member 130 that joins arm 112 provides the arm 112 with the ability to be positioned very close to the inner surface 200i. Thus, both the stabilizer instrument 10 and the positioner instrument 100 as described herein, can be oriented so that the arms 12 and 112, respectively, thereof, follow along the perimeter of the working space, thereby greatly increasing the amount of unobstructed working space 3 available to the surgeon, as shown in FIG. 24. Joint member 130 even permits arm 112 to be oriented in contact with the inner surface 200i. In particular, the mount body angles of positioning are possible due to the pivoting of joint member 130 (or of ball 36 with slot 36s). These angles created by pivoting joint member 130 are substantially smaller than the angles created by alternating ball joints 142."

Joint member 130 is pivotally mounted to mount body 122 at the distal end portion thereof, so that arm 112, which is joined to the distal end of joint member 130, extends from the distal end 124 of mount body 122. Arm 112 comprises a plurality of articulating links 140 that allow the arm 112 to be flexible in a first configuration, but which can be compressed to render the arm 112 substantially rigid in a second configuration. In the embodiment shown in FIGS. 22-23, links 140 include alternating ball joints 142 and biconcave disks 144, as described in more detail in U.S. Pat. No.

6,506,149. Alternatively, links 140 may include (but alternatives are not limited to these examples) a series of ball joints, a series of joints having one convex side and one concave side, or any of the other embodiments described in U.S. Pat. No. 6,506,149, or any of the embodiments described in U.S. Pat. No. 6,758,808, for example.

Each link 140 includes a central channel therethrough which may be tapered at both ends to allow a cable 46 (see the exploded view of FIG. 23) to pass through it smoothly and easily (and to improve rigidity in the arm's rigid state). Cable 46 extends through links 140, joint member 130, mount body 122 and connects proximally to an actuation mechanism 50 and connects distally to a mechanism configured to lock or unlock joint 56. The distal-most articulating member 43 at the distal end of arm 112 includes a cavity which opens to the distal end of the articulating member 43 and is adapted to at least partially receive coupling members 58, 47 and 60. A socket member 56s caps the distal end of the positioner arm 112 and is mated to the distal most articulating member 43 via coupling members 58, 47 and 60, in concert with the tensioning cable 46 which runs through the positioner.

The proximal end of cable 46 is connected to an actuation mechanism that is configured to increase or decrease tension in cable 46 by drawing the proximal end portion of cable 46 proximally or moving it distally relative to mount body 122, respectively. Increase and decrease of tension is actuated by actuator 152, such as the knob shown in FIGS. 22-23. Further details about the operation of mechanism 50 and alternative embodiments of such mechanism can be found, for example, in U.S. Pat. No. 6,758,808 and other patents incorporated by reference above. The present invention is not intended to be limited to the mechanism 50 shown in FIG. 23, as other mechanisms that provide the same function can be substituted.

In the embodiment shown in FIGS. 22-23, working end 114 includes a suction cup 151 that is configured to apply suction (negative pressure) to the surface of the tissue to be positioned or manipulated, to cause the cup 151 to engage the tissue. Suction cup 151 is in fluid communication with vacuum tube 162, which is configured, at its proximal end, to be connected in fluid communication with a source of negative pressure. A connector 164 provided at the proximal end of vacuum tube 162 may be color coded (e.g., color coded yellow, or some other distinct color), so that users can readily visually distinguish this vacuum tube 162 from vacuum tube 62 or other vacuum tubes that may be being used during the procedure. This is important to distinguish, since the magnitude of negative pressure used for the positioner 100 may differ significantly from the magnitude of negative pressure applied through the stabilizer 10.

The joint member 130 includes a swivel or pivot joint 132 that is formed by a disk member 134 pivotally mounted to mounting mechanism 120 as illustrated in FIG. 22 and in the partial, longitudinal sectional view of FIG. 25. The pivoting action provided by swivel joint 132 allows the stabilizer arm 112 to be pivoted out of the way so that the arm does not protrude into the surgical working space 3. As illustrated in FIG. 25, the arm 112 can be pivoted, by pivoting disk member 134 relative to mount body 122, so that the arm 112 approximates or even contacts the inner surface of the retractor 200i and the arm 112 can thus be adjusted to follow along the contour of the perimeter of the surgical working space 3.

Disk member 134 is slotted 134s through a proximal portion thereof, wherein the slot 134s typically sweeps through at least about 120 degrees of the periphery of the disk member 134, more typically at least about 150 degrees as shown in FIG. 26, and extends into the center of the disk member 134. Slot 134s allows the cable 46 to be tensioned while maintaining the swivel position of disk member 134 relative to the mount body 122.

FIG. 26 provides a top view of slot 134s in a partial, longitudinal sectional view taken in a plane at right angles to the plane along which the partial sectional view of FIG. 25 is taken. The curvature 34c at the distal ends of the slot facilitates bending and tightening of the cable 46 thereagainst when disk member 134 has been pivoted, and helps to eliminate or reduce variations in cable length/tension at different angular positions of the disk member 134.

Additionally, joint member 130 includes a ball 136 extending from a distal end of disk member 134 as shown in FIGS. 25-26. Ball 136 is dimensioned to cooperate with a concave proximal surface of link 144, thereby allowing ball and socket type, three-dimensional articulation of the link (and therefore the arm 112 and working end 114) relative to ball 136. Ball 136 may also be slotted 136s to further facilitate the downward angulation of arm 112 relative to mount body 122, thereby facilitating positioning the arm downwardly and following the contour of the retractor and perimeter of the surgical opening as illustrated in FIG. 24. Slot 136s may be provided with a curvature on the proximal end thereof. The curvature at the proximal end of the slot 136s facilitates bending and tightening of the cable thereagainst when arm 112 has been pivoted downwardly relative to ball 136/disk member 134, and helps to eliminate or reduce variations in cable length/tension at different angular positions of the arm 112. Further, a lubricious sleeve 46s (such as one made of polytetrafluoroethylene) or lubricious coating may be provided over cable 46 to help facilitate sliding and reduce friction.

Other variations of ball 136 may be provided, including, but not limited to the variations of ball 36 described above Likewise, alternative embodiments of disk member 134 may be provided like the alternative embodiments of disk member 34 described above.

Figure 27:
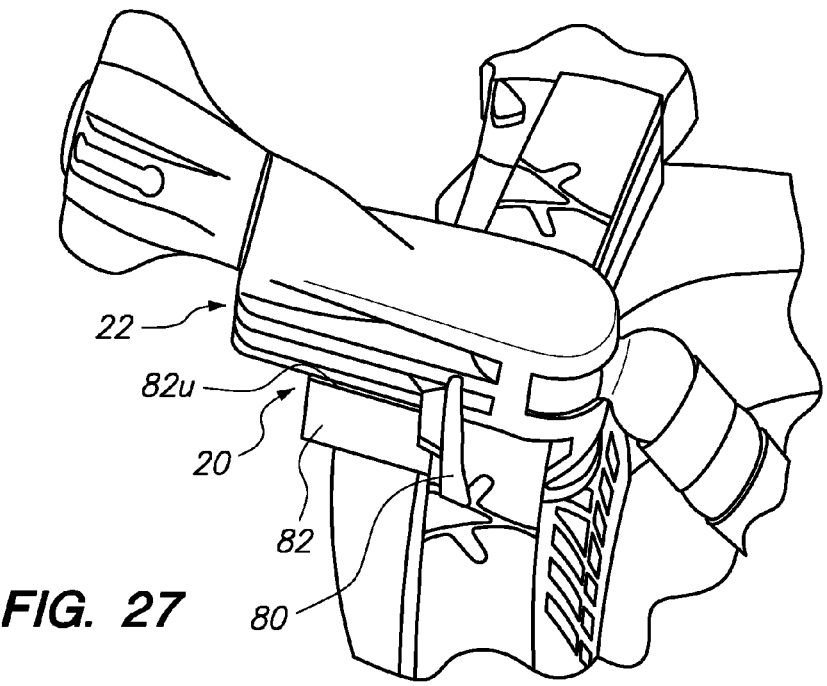
FIG. 27 is partial view illustrating details of a mounting mechanism according to an embodiment of the present invention.

FIG. 27 is partial view illustrating details of a mounting mechanism 20 according to an embodiment of the present invention. Although these details are described with regard to mounting mechanism 20 for a stabilizer instrument 10 (shown for example in FIGS. 3-4), it is noted that the details apply equally to a mounting mechanism 120 for a positioner instrument according to an embodiment of the present invention (shown for example in FIGS. 22-23), as the same mechanism can be used.

Unlike conventional locking mechanisms that use a lever and a cam to advance a movable jaw of a clamping mechanism relative to a fixed jaw in order to fix the mechanism to a fixed object, wherein the lever is co-planar with the bottom surface of the movable jaw or the bottom surface of the lever is below the top surface of the movable jaw, mounting mechanism actuator (e.g., lever or the like) 80 of the embodiment of the present invention shown in FIG. 27 is slidably mounted in mount body 22 (or 122) so that the entirety of the mounting mechanism actuator 80 is positioned above the upper surface 82u of movable jaw 82 and the working mechanism is embedded in the housing and jaw. This arrangement elevates the actuator 80 above the skin of the patient when the mounting mechanism 20 is being fixed to a sternal retractor for example, thereby greatly reducing the chances of pinching the skin of the patient in the actuator mechanism as the actuator 80 is actuated, whether to fix the mechanism to the retractor or remove it therefrom. Also, the camming mechanism is concealed within the movable jaw 82, so that it does not risk catching or grabbing the patient's tissue during use. Also, the mechanism is designed to allow for a lower profile for mounting, relative to current devices, and therefore the stabilizer or positioner is less obstructive to the surgical field and adjacent areas used by the surgeon. Some components of the mounting mechanism 20 are formed of metal to further reduce the profile of the mounting mechanism. For example, the lever 80a portion of the actuator, cam 81 (FIG. 28C) and, optionally, the lever grip portion 80b of the actuator are made of metal to provide a more compact configuration of the mounting mechanism compared to prior art designs that make one or more of these components from polymer.

Additionally, unlike conventional mounting mechanisms wherein the actuator lever is rotated distally to fix the mechanism to a retractor, the actuator 80 of the present invention is drawn proximally (i.e., towards the user) to fix or lock the mounting mechanism 20 (or 120) to a retractor. Ergonomically, this makes it easier for the user to lock an instrument 100 or 10 to a sternal retractor, as the proximal rotation is easier to perform and can generally be done with one hand, where it often takes both hands to fix a mechanism that requires distal rotation of the lever to fix the mechanism, since it is easy to hold the body 22 and pull, using one hand, but difficult to hold the body and push, using the same hand. Also, in the conventional mechanisms, the lever extends outwardly from the mounting mechanism and extends alongside the rail of the retractor when the mechanism is fixed thereto, thereby preventing another instrument from being mounted close to that mechanism. In the present invention, however, actuator 80 is drawn back proximally in the locked position and streamlined with the mounting mechanism 20,120, see FIG. 28A. This allows placement of another instrument much closer to the mounting mechanism 20, 120 on the rail of the retractor, relative to what is permitted by currently available mechanisms.

Figures 28A, 28B:
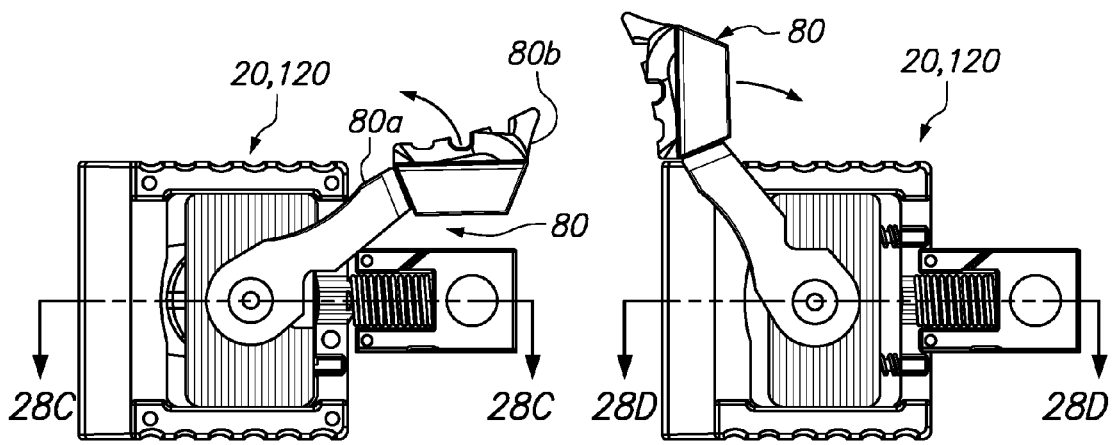
FIG. 28A shows an actuator drawn back proximally in the locked position and streamlined with the mounting mechanism according to an embodiment of the present invention.
FIG. 28B illustrates the actuator of FIG. 28A in the unlocked configuration according to an embodiment of the present invention.
Figure 28C:
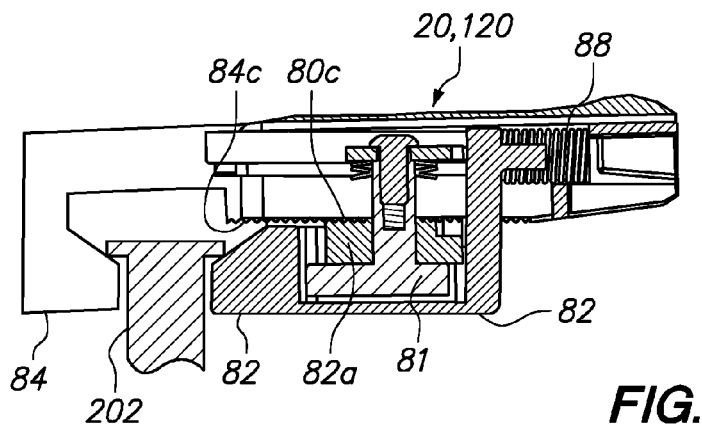
FIG. 28C is a cross-sectional view of FIG. 28A taken along line 28C-28C.

FIG. 28B illustrates the actuator 80 in the unlocked configuration, which allows initial placement of the mounting mechanism on the fixed object, such as a sternal retractor, or removal of the mounting mechanism from the fixed object. FIG. 28C is a cross-sectional view of FIG. 28A taken along line 28C-28C, and showing mounting mechanism 20,120 in the locked configuration. Movable jaw 82 is biased toward fixed jaw 84 by biasing member 88, such as a coil spring, or other biasing member. Accordingly, when mounting mechanism 20, 120 is placed over the rail 202, the rail 202 is contacted on opposite sides by jaws 84, 82, as biased to this position by biasing member 88. By drawing actuator 80 proximally, a cam 81 linked to actuator 80 is rotated and draws an internal jaw component 82a in movable jaw 82 upwardly to engage internal jaw component teeth 82c against upper teeth 84c, thereby locking the movable jaw 82 relative to the fixed jaw 84 and locking the mounting mechanism 20, 120 in a position clamped against the rail 202. Thus mechanism 20,120 holds the instrument 10, 1000 securely to the rail 202, assisting in the prevention of movement of the arm or surgical instrument.

Figure 28D:
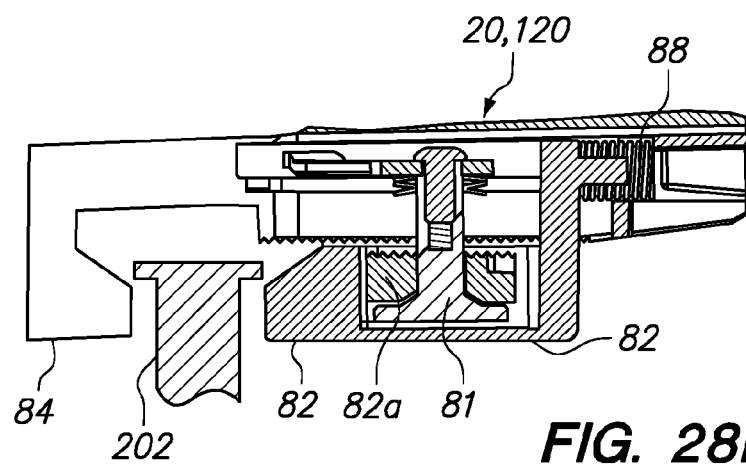
FIG. 28D is a cross-sectional view of FIG. 28B taken along line 28D-28D.

FIG. 28D is a cross-sectional view of FIG. 28B taken along line 28D-28D, and showing mounting mechanism 20,120 in the unlocked configuration and with movable jaw retraced so that the mounting mechanism 20, 120 can be removed from the rail 202 (or to facilitate placing the mounting mechanism 20, 120 over the rail before clamping and locking it). By pushing actuator 80 distally, the cam 81 counter-rotates, thereby removing teeth 82c from contact with teeth 84c and allowing movable jaw 82 to move away from fixed jaw 84, as well as rail 202, and providing enough clearance between both jaws 82, 84 relative to rail 202 to allow the mounting mechanism 20, 120 to be lifted off of the rail 202. The pushing motion of the actuator 80 requires less effort by the user to unlock and remove the instrument from the surgical site. Further details about the operation of the cam relative to the movable jaw can be found in U.S. Pat. No. 6,685,632. A spring 88 is provided that biases movable jaw 82 towards fixed jaw 84. To first place the jaws 82, 84 over the rail 202, the user draws back on jaw 82 while holding the fixed portion of the mechanism 20, 120 (jaw 84 or other fixed portion) to spread the jaws apart. Once the jaws have cleared the top rail flanges, the jaw 82 can be released, and spring 88 moves jaw 82 towards jaws 84 to bring the jaws into lateral contact with the rail 202.

Figures 29A, 29B:
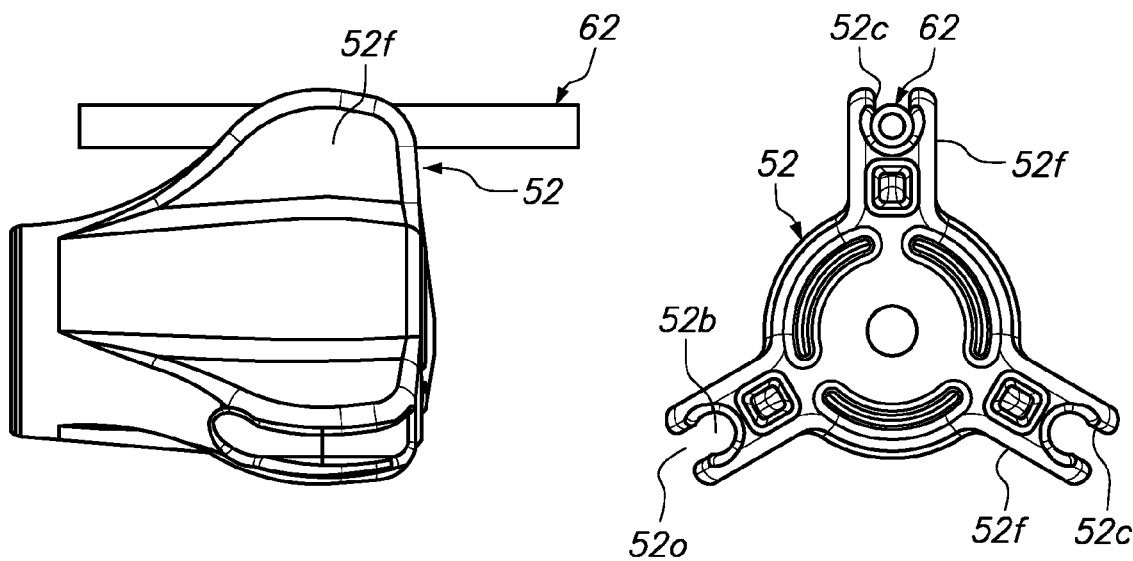
FIGS. 29A-29B show a side view and an end view, respectively, of an actuator according to an embodiment of the present invention.

FIGS. 29A-29B show a side view and an end view, respectively, of an actuator 52. Actuator 52 is provided with a clip 52c provided in at least one of the fins 52f thereof. In the embodiment shown, a clip 52c is formed in each of the fins 52f. Alternatively, only one or two of the fins 52f could be provided with clips 52c. Each clip 52c is configured to receive and temporarily or reversibly hold suction tube 62 to help maintain the suction tube in a low profile as it follows along the profile of the instrument 10/arm 12, e.g., see FIG. 3. The opening 52o of the clip 52c has a distance across that is slightly less than the outside diameter of the tube 62. Accordingly, the tube 62 has to be pinched or deformed in order to insert it through the opening 52o of the clip 52c.

Alternatively, or in addition to temporarily holding tube 62 in clip 52c, tube may be temporarily held in recess 22c provided in mount body 22, as shown in FIG. 29C. Recess 22c is configured to receive and temporarily hold suction tube 62 to help maintain the suction tube in a low profile as it follows along the profile of the instrument 10/arm 12, e.g., see FIG. 29C. The opening of the recess 22c has a distance across that is slightly less than the outside diameter of the tube 62. Accordingly, the tube 62 has to be pinched or deformed in order to insert it through the opening of the recess 22c so that it is retained in recess 22c once inserted there, until a force is applied to pull it back out of the recess 22c.

Preferably, tube 62 is a soft, flexible, reinforced tube. However, the interior 52b of the main body of the clip 52c has an inside diameter only slightly smaller than the outside diameter of the tube 62, so as grip the tube 62 while keeping constriction relatively insubstantial. Accordingly, the tube 62 is held in position in space 52b by the soft grip and opening 52o of clip 52c prevents the tubing 62 from escaping the clip during use of the instrument, as operator intervention is required to remove the tube again so that it can be repositioned in the opening 52o.

FIGS. 30A-30B show a side view and an end view, respectively, of actuator 152. Actuator 152 is provided with a clip 152c provided in at least one of the fins 152f thereof. In the embodiment shown, a clip 152c is formed in each of the fins 152f. Alternatively, a fewer number or only one of the fins 152f could be provided with clip 152c. Each clip 152c is configured to receive and temporarily hold suction tube 162 to help maintain the suction tube 162 in a low profile as it follows along the profile of the instrument 100/arm 112, e.g., see FIG. 22. The opening 152o of the clip 152c has a distance across that is slightly less than the outside diameter of the tube 162. Accordingly, the tube 162 has to be pinched or deformed in order to insert it through the opening 152o of the clip 152c. However, the interior 152b of the main body of the clip 152c has an inside diameter slightly smaller than the outside diameter of the tube 162, so as grip the tube 162, while not overly constricting the tube 162. Accordingly, the tube 162 is held in position in space 152b by the soft grip and opening 152o of clip 152c prevents the tubing 162 from escaping the clip during use of the instrument, as operator intervention is required to remove the tube so that it can be repositioned in the opening 152o.

Alternatively, or in addition to temporarily holding tube 62 in clip 152c, tube may be temporarily held in a recess provided in mount body 122. The recess in mount body 122 can be configured in the same way as recess 22c shown in FIG. 29C and described above, and is configured to receive and temporarily hold suction tube 62 to help maintain the suction tube in a low profile as it follows along the profile of the instrument 100/arm 112. It is further noted that mount body 122 may be constructed to be the same as mount body 22.

Figure 31A:
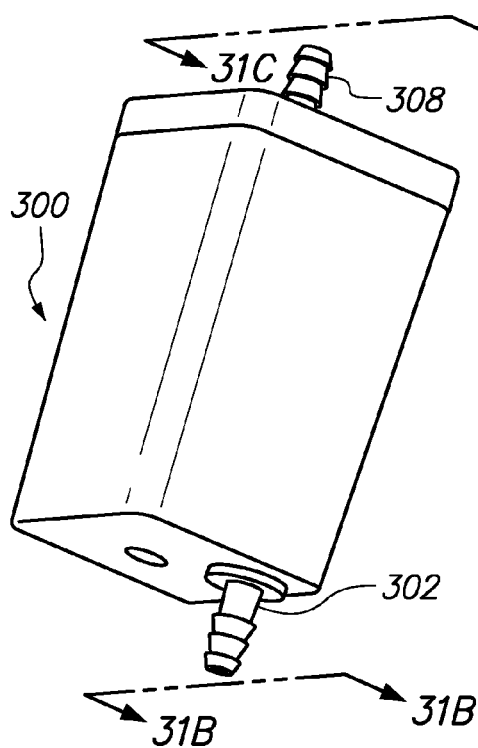
FIG. 31A is a perspective view of a canister according to an embodiment of the present invention.
Figure 31B:
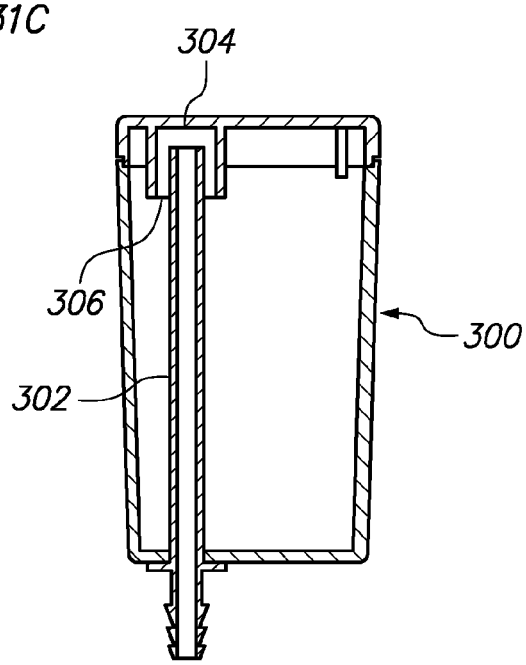
FIG. 31B is a longitudinal sectional view of the canister of FIG. 31A taken along line 31B-31B.
Figure 31C:
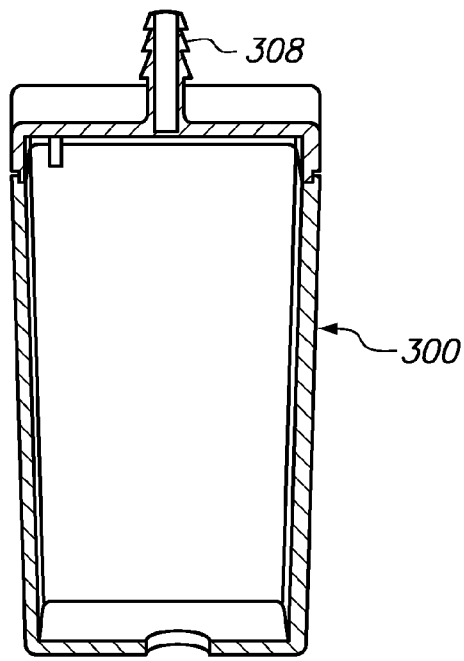
FIG. 31C is a longitudinal sectional view of the canister of FIG. 31A taken along line 31C-31C.

FIG. 31A is a perspective view of a canister 300 that is configured to be placed in line, in fluid communication with vacuum line 62 or 162, in between device 10 or 100 and the vacuum source. As vacuum is applied from vacuum source 402 or 404 (see FIG. 32), the suction applied to the tissues of the patient 1 not only performs the desired engagement with the working ends 14,114 with the target tissues, but also tends to draw fluids and particulates up through the vacuum tubes 62, 162. These fluids and particulates are drawn in through tubing 302 (see FIG. 31B). A closed-ended cap 304 is provided over the proximal end of tube 302. The inside diameter of cap 304 is significantly larger than the outside diameter of tube 302 so as to form an annular gap 306 therebetween. As the fluids and particulates exit the proximal end of tube 302, they impact the closed end of cap 304 or simply (in the case of heavier materials) flow over the sides of the tube 302 like a fountain. In either case, a majority of the liquids contained in the fluids, as well as larger, heavier particulates, precipitate out of the fluid flow and are contained by the canister 300 and held at the bottom end portion of the canister 300 by gravity, since the canister is oriented vertically during use (e.g., see FIG. 32). Also, cap 304 prevents spillage and splatter of particulates and fluids onto the side walls of the canister 300, thereby preventing dirtying of the walls that would otherwise obstruct the view of the contents and level of the contents. The lighter fluids, such as gases, and potentially some smaller particulates continue in the flow, out through tubing 308, see FIG. 31C.

Figure 32:
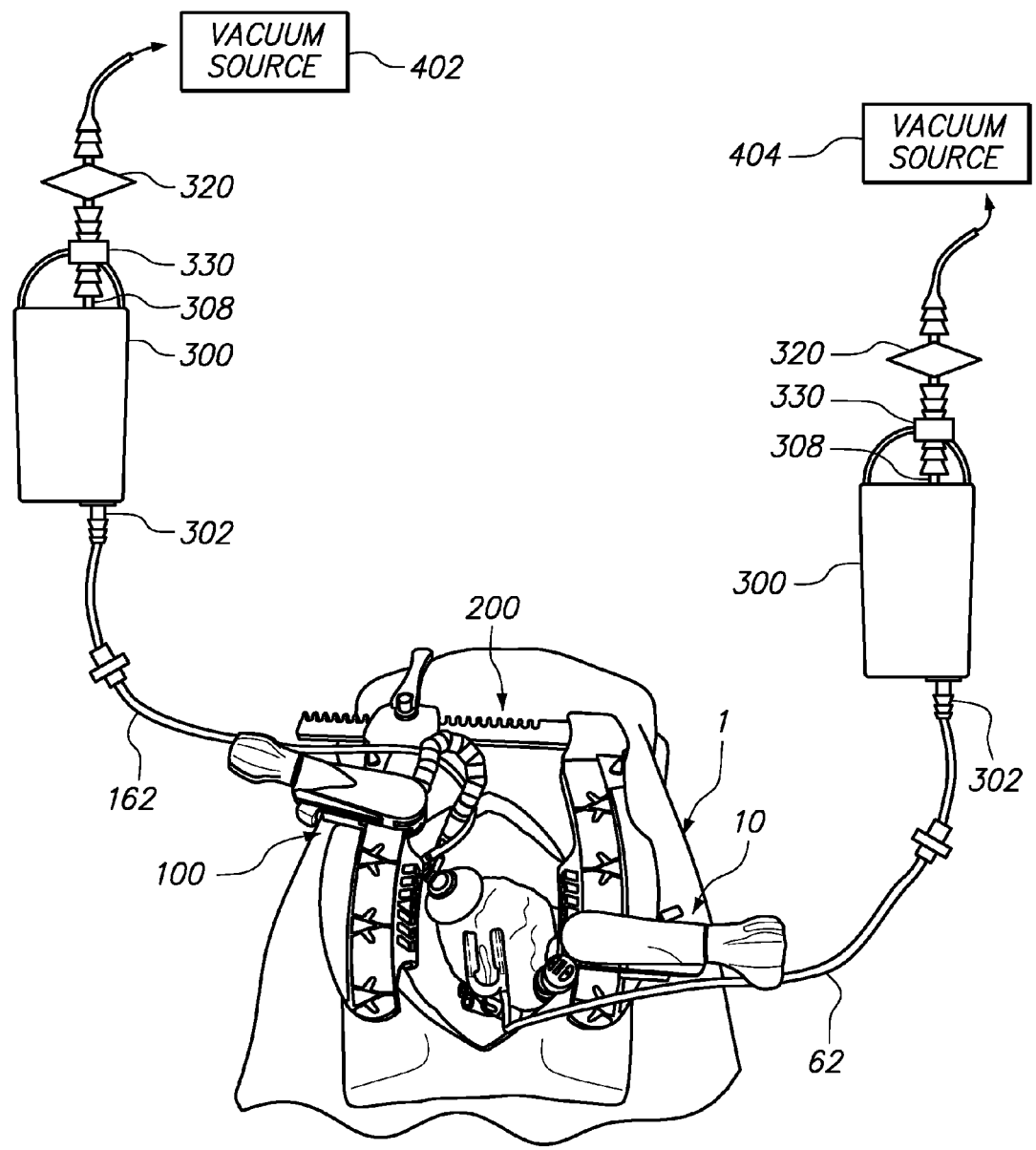
FIG. 32 illustrates use of a stabilizer instrument and a positioner instrument, each with a canister according to an embodiment of the present invention.

A filter 320 is provided in line, in fluid communication with canister 300, between canister 300 and vacuum source 402 or 404, see FIG. 32. Thus, unlike some conventional canisters, filter 320 is not provided inside the canister 300, but is upstream thereof. This prevents filter 320 from being saturated by liquids accumulated in the canister, and also makes it possible to change the filter 320 without having to change the canister 300, or to change or empty the canister 300 without having to change the filter 320. Filter 320 is configured to trap particulates that were not contained by the canister 300.

Canister 300 is preferably provided with at least one substantially flat side that facilitates mounting of the canister 300 along a wall, for example. In the embodiment shown in FIGS. 31A-31D, canister 300 has four substantially flat sides and is substantially square in cross-section. However, other cross-sectional shapes, including, but not limited to triangular, semi-circular or semi-oval may be substituted. The external surface of the canister is also preferably provided with a matted finish so as to minimize glare that might be otherwise reflected from the intense operating room lighting. This not only prevents glare as a distraction, but also facilitates viewing the contents of the canister 300, so that it can be monitored to ensure that it does not fill up before changing it.

Figure 31D:
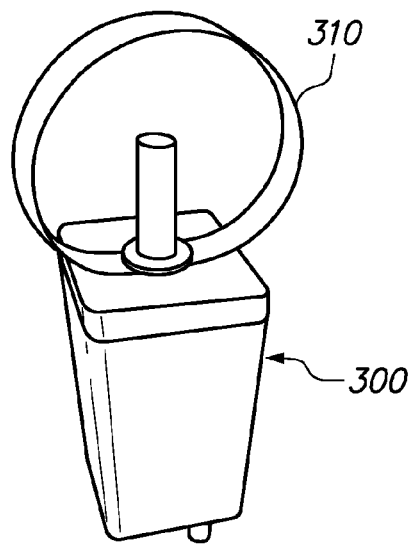
FIG. 31D illustrates a strap provided with a canister according to an embodiment of the present invention.

FIG. 31D illustrates a strap 310 that may also be provided with canister 300. Strap 310 is attached to canister 300 and is configured to hang the canister from any stationary projection 330 (see FIG. 32) in the operating room so as to maintain the canister 300 hanging in the desired vertical orientation (see FIG. 32), so that outlet 308 is higher than inlet 302 and canister 300 is oriented substantially vertically.

Figure 33A:
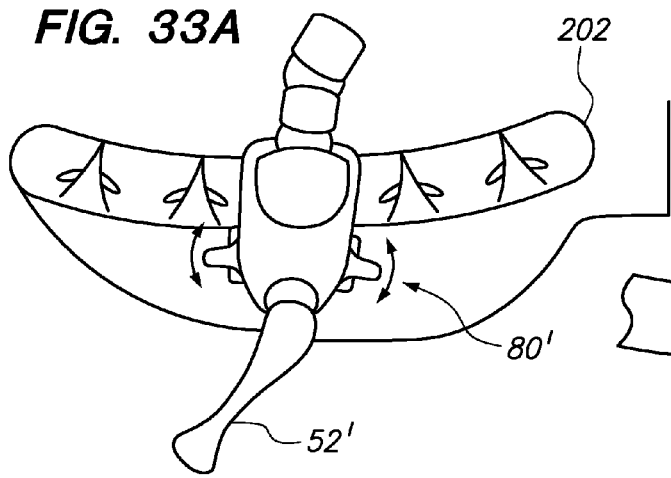
FIGS. 33A-33B show an alternative mounting mechanism actuator according to an embodiment of the present invention.
Figure 33B:
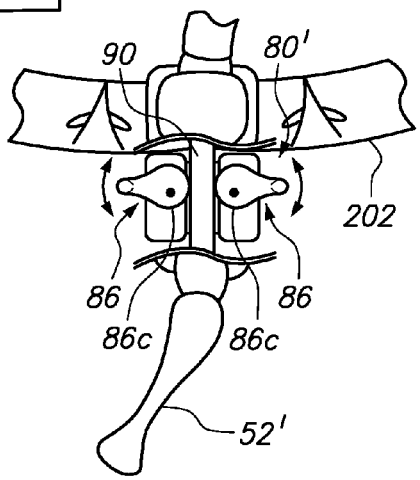

Turning now to FIGS. 33A-33B, an alternative mounting mechanism actuator 80' is described. Actuator 80' is shown being used with the instrument 10 of FIG. 20A. However, any of the other instruments 10, 100 described herein could be modified to use this alternative mounting mechanism actuator 80'. Rocker switches 86 with cams 86c interface with rail 202 and apply compressive forces thereagainst, when rotated (see curved arrows in FIG. 33B), thereby firmly clamping the mount body and instrument 10,100 to the rail 202.

Figure 34A:
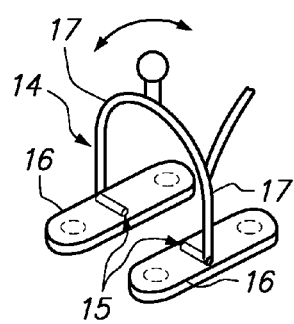
FIGS. 34A-34B illustrate alternative features that may be provided with a working end of a stabilizer instrument according to various embodiments of the present invention.
Figure 34B:
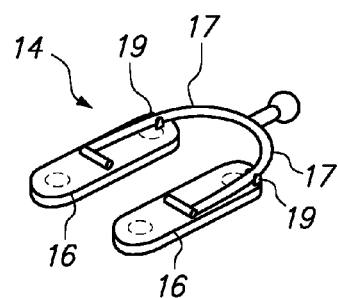

FIGS. 34A-34B illustrate alternative features that may be provided with a working end 14 of a stabilizer instrument according to various embodiments of the present invention. The contact members 16 and supports thereof may be configured to provide a blower/mister device 15 integrated into the contact members as shown, so that nozzles or openings of the blower/mister device are directed inwardly, between the contact members 16 that they are mounted in, so that they direct mist toward the surgical target located between the contact members 16. Alternatively, the stabilizer instrument may be configured for a blower/mister device to be attached thereto. The working end may be configured for a blower/mister device to be attached thereto.

Additionally or alternatively, the supports 17 may be configured to pivot relative to contact members 16, as indicated by the arrows in FIG. 34A. Contact members 16 may also be provided with clips 19 at their distal ends configured to form a snap fit with the support members 17, so as to maintain the working end in a very low profile where both contact members and supports extend aligned substantially in the same plane.

Figure 35:
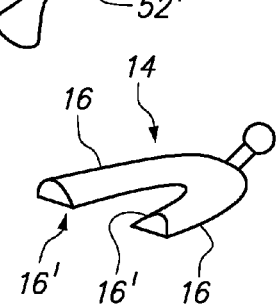
FIG. 35 illustrates a modification whereby contact members are tapered from a thicker dimension at the outside edges thereof, to a thinnest dimension at the inside edges 16' thereof according to an embodiment of the present invention.

FIG. 35 illustrates a modification whereby contact members 16 are tapered from a thicker dimension at the outside edges thereof, to a thinnest dimension at the inside edges 16' thereof. Other modifications that may be performed include, but are not limited to: mounting one or more cameras on contact members 16 which are linkable to a monitor for viewing, and/or providing an arm 12, 112 that is flexible in a first configuration and, upon application of vacuum thereto, is made rigid in a second configuration.

Figure 36:
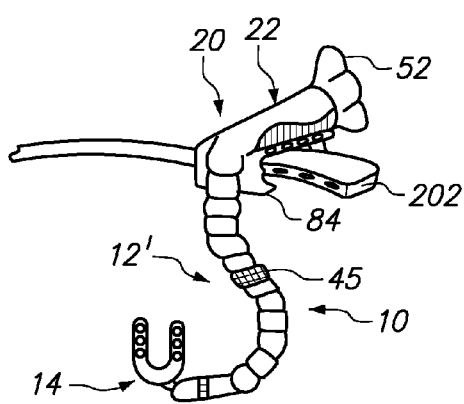
FIG. 36 illustrates an embodiment of a device having an alternative arm in which an intermediate link is provided that is adjustable by a user to adjust the tension in the cable distally thereof according to an embodiment of the present invention.

FIG. 36 illustrates an embodiment of device 10 having an alternative arm 12' in which an intermediate link 45 is provided that is adjustable by a user to adjust the tension in the cable distally thereof. This feature can accordingly be used to tighten/lock the working end 14 and links distal of link 45, while still allowing the links proximal of link 45 to remain flexible. In this way, the user could fix an initial "rough" or coarse positioning of working end 14 by tightening the distal links using link 45 as described, and then fine positioning can be performed by making further fine adjustments to the positioning by manipulating the links proximal of link 45. Upon achieving satisfactory fine adjustments to the positioning, the remainder of the links can then be locked down using actuator 52. Further, alternatively, link 45 can be configured to tighten the links proximal thereof while allowing links distal thereof to remain loose/flexible. In an alternative embodiment, a second cable alongside cable 46 is provided that connects to link 45 distally, passes through the links proximal of link 45 and connects to mount body 22. It is noted that although the modifications described with regard to FIG. 36 are shown with regard to a stabilizer instrument 10, that any and all of such modifications can also be applied to a positioner instrument 100.

Figure 37:
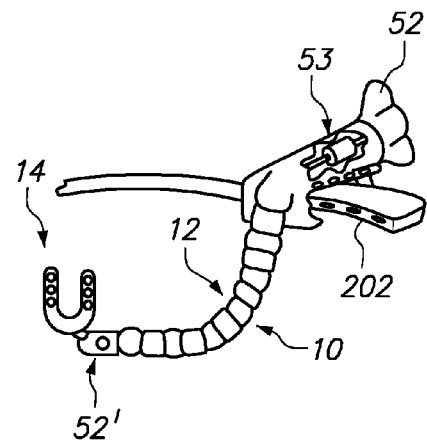
FIG. 37 illustrates an embodiment of a device having an alternative actuation mechanism according to an embodiment of the present invention.

FIG. 37 illustrates an embodiment of device 10 having an alternative actuation mechanism 52, 52', 53. In this embodiments actuator 52 can be operated the same way as described above with regard to FIGS. 3-4. Alternatively, a motor 53 is provided that can be actuated by actuator 52', for example, a push button or other switch electrically connected through arm 12 and mount body 22 to motor 53, to drive actuator 52 to increase or decrease tension in cable 46. Thus, actuator 52' allows a user to tighten/lock the working end 14 and arm 12 from the distal end portion of the instrument, for example, while the users hand(s) are in the vicinity of the distal end portion of the instrument 10 to position the working end 14 as desired. It is noted that although the modifications described with regard to FIG. 37 are shown with regard to a stabilizer instrument 10, that the actuator 52' and motor 53 can likewise be implemented in a positioner instrument 100 in the same manner to control actuator 152.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A surgical instrument comprising:
a mount body, an arm, a joint, and a tool;
the mount body configured to mount to a retractor, a bottom surface of the mount body facing the retractor when mounted, a front edge of the mount body running at an angle to the bottom surface;
the arm pivotally connected on a proximal end of the arm via the joint to or along the front edge of the mount body; the tool connected to a distal end of the arm;
the arm configured to be movable between a plurality of positions relative to the mount body and to be temporarily lockable in these positions; and
the joint configured such that a proximal portion of the arm extending from and adjacent the mount body is pivotable to and temporarily lockable in a position substantially perpendicular to the mount body along portions of the front edge.

2. The surgical instrument of claim 1, wherein the surgical instrument further comprises a universal connector configured to connect the mount body to any one of a plurality of retractors of different size.

3. The surgical instrument of claim 1, wherein, the joint includes a disk member.

4. The surgical instrument of claim 3, wherein the joint includes a slotted ball.

5. The surgical instrument of claim 4, wherein the instrument includes an actuator rotatably mounted to the mount body at the proximal end of the mount body and a cable extending from the actuator through the mount body, disk member, slotted ball and arm, and the actuator and the cable are configured to change a state of the arm from a flexible state to a rigid state by rotation of the actuator in a first rotational direction, and from the rigid state to the flexible state by rotation of the actuator in a counter-rotational direction.

6. The surgical instrument of claim 5, wherein a tube is provided in fluid communication with the tool, and the actuator includes a clip configured to receive and temporarily hold the tube to maintain the tube in a low profile arrangement with the instrument.

7. The surgical instrument of claim 4, wherein an actuator is rotatably mounted to the mount body at the proximal end of the mount body and a cable extends from the actuator through the mount body, disk member, slotted ball and arm.

8. The surgical instrument of claim 7, wherein the actuator and the cable are configured to change a state of the arm from a flexible state to a rigid state by rotation of the actuator in a first rotational direction, and from the rigid state to the flexible state by rotation of the actuator in a counter-rotational direction.

9. The surgical instrument of claim 3, wherein the instrument includes a cable extending through the disk member, at least a portion of the arm and at least a portion of the mount body, wherein the disk member comprises a slot formed therein, the slot being curved to facilitate bending and tightening of the cable thereagainst when the disk member has been pivoted, thereby helping to eliminate or reduce variations in at least one of cable length and cable tension at different angular positions of the disk member relative to the mount body.

10. The surgical instrument of claim 1, wherein a tube is provided in fluid communication with the tool.

11. The surgical instrument of claim 10, wherein the mount body includes a recess sized to receive and removably retain the tube.

12. The surgical instrument of claim 10, wherein a canister is provided in fluid communication with the tube, the canister having an opening for connecting the canister in fluid communication with a vacuum source, the canister configured to trap fluid therein.

13. The surgical instrument of claim 12, wherein a filter is in fluid communication with the opening of the canister, and the filter is configured to be connected to the vacuum source and to filter particulates from effluent from the canister.

14. The surgical instrument of claim 12, wherein a strap is connected to the canister and adapted to hang the canister in an upright orientation wherein the opening for connecting the canister with a vacuum source is higher than a connection forming the fluid communication of the canister with the vacuum tube.

15. The surgical instrument of claim 1, wherein the instrument is a stabilizer and the tool comprises at least one contact member configured to be exerted against a tissue surface to stabilize the tissue surface.

16. The surgical instrument of claim 1, wherein the instrument is a positioner and the tool comprises a suction member defining a vacuum space therein, wherein the suction member is configured to exert sufficient suction force on an organ to move the organ when the suction member is placed against the organ, a negative pressure is applied within the vacuum space to engage the suction member with the organ, and the suction member is moved.

17. The surgical instrument of claim 1, wherein the arm comprises a most proximal link that is immediately adjacent the joint member, and the most proximal link is positionable and temporarily lockable in the position substantially perpendicular to the mount body in which the most proximal link is positioned at an angle of about 80 degrees to about 90 degrees to the mount body.

18. A surgical instrument comprising:
a mount body, an arm, a tool, and a tube;
the mount body configured to mount to a retractor or a surgical table; the arm pivotally connected on a proximal end to the mount body; the tool connected to a distal end of the arm; the arm configured to be movable between a plurality of positions relative to the mount body and to be temporarily lockable in these positions;
a distal end of the tube connected at or adjacent a distal end of the arm; and
the mount body comprising a recess configured to removably retain the tube.

19. The surgical instrument of claim 18, further comprising an actuator associated with the arm, wherein the actuator comprises a plurality of fins, each fin provided with a clip formed therein that is configured to receive and reversibly hold the tube.

20. A surgical instrument comprising:
a mount body having a top portion, a distal end, a proximal end and a bottom portion;
a plurality of mount body jaws formed by or connected to the bottom portion, wherein the plurality of mount body jaws include a moveable jaw;
a joint member engaged to an arm, the arm extending distally from the joint member and terminating with a working end mounted to a distal end portion of the arm, the joint member pivotally mounted at a distal end portion of the mount body; wherein the arm through positioning of the joint member is capable of being positioned towards the left or right distal regions of the mount body; and
a mounting mechanism comprising a camming mechanism and an actuator for the camming mechanism, wherein the camming mechanism is disposed within the moveable jaw.

21. The surgical instrument of claim 20, wherein the joint member is capable of being positioned with constrained movement of at least a portion of the joint member with respect to a plane horizontally aligned with respect to the top portion of the mount body.

22. The surgical instrument of claim 20, wherein the working end is configured for attachment to the surface of a heart, the working end further including a stabilizer member to engage one or both sides of a coronary artery, or a positioner member capable of receiving the apex of the heart.

23. The surgical instrument of claim 20, wherein the arm through positioning of the joint member is positionable towards the left or right distal regions of the mount body without interfering with a space located above the mount body jaws and immediately dorsal to the top portion of the mount body.

24. The surgical instrument of claim 20, wherein the actuator is slidably mounted to the mount body and the actuator is disposed above an upper surface of the moveable jaw.

* * * * *